(12) United States Patent
Schnider

(10) Patent No.: US 8,461,152 B2
(45) Date of Patent: Jun. 11, 2013

(54) ARYLCYCLOHEXYLETHERS OF DIHYDROTETRAAZABENZOAZULENES

(75) Inventor: Patrick Schnider, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/471,491

(22) Filed: May 15, 2012

(65) Prior Publication Data

US 2012/0225865 A1    Sep. 6, 2012

Related U.S. Application Data

(62) Division of application No. 12/621,547, filed on Nov. 19, 2009, now Pat. No. 8,227,458.

(30) Foreign Application Priority Data

Nov. 28, 2008 (EP) .................................. 08170188

(51) Int. Cl.
*A61P 5/24* (2006.01)
*A61K 31/5517* (2006.01)
*C07D 487/04* (2006.01)

(52) U.S. Cl.
USPC ........................................ 514/220; 540/563

(58) Field of Classification Search
USPC .......................................... 514/220; 540/563
See application file for complete search history.

(56) References Cited

U.S. PATENT DOCUMENTS

| 7,265,104 | B2 | 9/2007 | Elliott et al. |
| 2002/0103373 | A1 | 8/2002 | Hoekstra et al. |
| 2007/0249585 | A1 | 10/2007 | Johnson |
| 2011/0245237 | A1 | 10/2011 | Dolente et al. |
| 2011/0251183 | A1 | 10/2011 | Dolente et al. |
| 2011/0263573 | A1 | 10/2011 | Dolente et al. |
| 2011/0263578 | A1 | 10/2011 | Dolente et al. |
| 2011/0275801 | A1 | 11/2011 | Dolente et al. |

FOREIGN PATENT DOCUMENTS

| EP | 2292621 | 3/2011 |
| KR | 2007/0020462 | 2/2007 |
| WO | 96/22292 | 7/1996 |
| WO | 02/083681 | 10/2002 |
| WO | 2004/074291 | 9/2004 |
| WO | 2005/068466 | 7/2005 |
| WO | 2006/021882 | 3/2006 |
| WO | 2006/114706 | 11/2006 |
| WO | 2006/123242 | 11/2006 |
| WO | 2008/084005 | 7/2008 |
| WO | 2010/054961 | 5/2010 |
| WO | 2010/057795 | 5/2010 |

OTHER PUBLICATIONS

"International Search Report for PCT/EP2009/064804—Jan. 14, 2010".
Altemus et al., Arch. Gen. Psychiatry 49:9-20 ( 1992).
"International Search Report PCT/EP2011/056071—May 12, 2011".
Regier et al., Br. J. Psychiatry Suppl.:24-28 ( 1998).
Aughton et al., Br. J. Pharmacol.:253 ( 2008).
Robben et al., Am. J. Physiol. Renal. Physiol. 291:F257-270 ( 2006).
Vankerckhoven et al., Eur. J. Pharmacol. 449(1-2):135-141 ( 2002).
"International Search Report PCT/EP2011/055516—May 23, 2011".
"International Search Report for PCT/EP2011/054582—Mar. 25, 2011".
Gupta et al., Br. J. Pharmacol. 155:118-126 ( 2008).
"International Search Report PCT/EP2011/056391—Jun. 27, 2011".
Raskind et al., Biol. Psychiatry 22:453-462 ( 1987).
Neumann, J. Neuroendocrinol. 20:858-865 ( 2008).
Bielsky et al., Neuropsychopharmacology 29:483-493 ( 2004).
Brouard et al., Bjog. 107:614-619 ( 2000).
Michelini et al., Ann. NY Academy Science 897:198-211 ( 1999).
Ebner et al., "Eur. J. Neurosci." 15(2):384-388 ( 2002).
Liebsch et al., Regulatory Peptides 59(2):229-239 ( 1995).
"International Search Report for PCT/EP2011/057368—Jul. 14, 2011".
Yirmiya et al., 11:488-494 ( 2006).
Gal et al., "Progress in Brain Research" Elsevier (XP001205440), 139:197-210 ( 2002).
Kendler et al., Arch. Gen. Psychiatry 60:789-796 ( 2003).

(Continued)

*Primary Examiner* — Brenda Coleman

(57) ABSTRACT

The present invention is concerned with arylcyclohexylethers of dihydro-tetraazabenzoazulenes, i.e. arylcyclohexylethers of 5,6-dihydro-4H-2,3,5,10b-tetraaza-benzo[e]azulenes of formula I

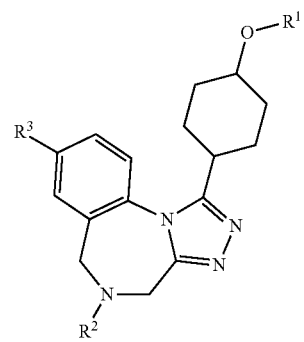

wherein $R^1$, $R^2$ and $R^3$ are as described herein, their manufacture, and pharmaceutical compositions containing them. The compounds according to the invention act as V1a receptor modulators, and in particular as V1a receptor antagonists. The active compounds of the present invention are useful as therapeutics acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

22 Claims, No Drawings

OTHER PUBLICATIONS

Thompson et al., Psychoneuroendocrinology 29:35-48 (2004).
"Opposition in Costa Rican Appl. No. 2011-0220 Sep. 20, 2011".
(International Search Report PCT/EP2009/065354 Feb. 8, 2010).
Landgraf et al., Regul. Pept. 59:229-239 (1995).
(Translation of Taiwanese Off Act in Corres Appl ROC 098140192 Apr. 25, 2012).
(Chilean Office Action Nov. 14, 2012).

ARYLCYCLOHEXYLETHERS OF DIHYDROTETRAAZABENZOAZULENES

PRIORITY TO RELATED APPLICATION(S)

This application is a division of U.S. application Ser. No. 12/621,547, filed Nov. 19, 2009, now pending; which claims the benefit of European Patent Application No. 08170188.0, filed Nov. 28, 2008. The entire contents of the above-identified applications are hereby incorporated by reference.

BACKGROUND OF THE INVENTION

Vasopressin is a 9 amino acid peptide mainly produced by the paraventricular nucleus of the hypothalamus. In the periphery vasopressin acts as a neurohormone and stimulates vasoconstriction, glycogenolysis and antidiuresis.

Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water reabsorption and mediates the antidiuretic effects of vasopressin (Robben, et al. (2006). Am J Physiol Renal Physiol. 291, F257-70, "Cell biological aspects of the vasopressin type-2 receptor and aquaporin 2 water channel in nephrogenic diabetes insipidus"). Compounds with activity at the V2 receptor may therefore cause side-effects on blood homeostasis.

The oxytocin receptor is related to the Vasopressin receptor family and mediates the effects of the neurohormone oxytocin in the brain and the periphery. Oxytocin is believed to have central anxiolytic effects (Neumann (2008). J Neuroendocrinol. 20, 858-65, "Brain oxytocin: a key regulator of emotional and social behaviours in both females and males"). Central oxytocin receptor antagonism might therefore lead to anxiogenic effects, which are regarded as undesired side-effects.

In the brain vasopressin acts as a neuromodulator and is elevated in the amygdala during stress (Ebner, et al. (2002). Eur J Neurosci. 15, 384-8., "Forced swimming triggers vasopressin release within the amygdala to modulate stress-coping strategies in rats"). It is known that stressful life events can trigger major depression and anxiety (Kendler, et al. (2003). Arch Gen Psychiatry. 60, 789-96, "Life Event Dimensions of Loss, Humiliation, Entrapment, and Danger in the Prediction of Onsets of Major Depression and Generalized Anxiety") and that both have very high comorbidity, with anxiety often preceding major depression (Regier, et al. (1998). Br J Psychiatry Suppl. 24-8, "Prevalence of anxiety disorders and their comorbidity with mood and addictive disorders"). The V1a receptor is extensively expressed in the brain and particularly in limbic areas like the amygdala, lateral septum and hippocampus which are playing an important role in the regulation of anxiety. Indeed V1a knock-out mice show a reduction in anxious behavior in the plus-maze, open field and light-dark box (Bielsky, et al. (2004). Neuropsychopharmacology. 29, 483-93, "Profound impairment in social recognition and reduction in anxiety-like behavior in vasopressin V1a receptor knockout mice"). The downregulation of the V1a receptor using antisense oligonucleotide injection in the septum also causes a reduction in anxious behavior (Landgraf, et al. (1995). Regul Pept. 59, 229-39., "V1 vasopressin receptor antisense oligodeoxynucleotide into septum reduces vasopressin binding, social discrimination abilities, and anxiety-related behavior in rats"). Vasopressin or the V1a receptor are also implicated in other neuropsychological disorders: genetic studies recently linked sequence polymorphism in the promoter of the human V1a receptor to autistic spectrum disorders (Yirmiya, et al. (2006). 11, 488-94, "Association between the arginine vasopressin 1a receptor (AVPR1a) gene and autism in a family-based study: mediation by socialization skills"), intranasal administration of vasopressin was shown to influence aggression in human males (Thompson, et al. (2004). Psychoneuroendocrinology. 29, 35-48, "The effects of vasopressin on human facial responses related to social communication") and vasopressin levels were found to be elevated in schizophrenic patients (Raskind, et al. (1987). Biol Psychiatry. 22, 453-62, "Antipsychotic drugs and plasma vasopressin in normals and acute schizophrenic patients") and patients with obsessive-compulsive disorder (Altemus, et al. (1992). Arch Gen Psychiatry. 49, 9-20, "Abnormalities in the regulation of vasopressin and corticotropin releasing factor secretion in obsessive-compulsive disorder").

The V1a receptor is also mediating the cardiovascular effects of vasopressin in the brain by centrally regulating blood pressure and heart rate in the solitary tract nucleus (Michelini and Morris (1999). Ann N Y Acad Sci. 897, 198-211, "Endogenous vasopressin modulates the cardiovascular responses to exercise"). In the periphery it induces the contraction of vascular smooth muscles and chronic inhibition of the V1a receptor improves hemodynamic parameters in myocardial infarcted rats (Van Kerckhoven, et al. (2002). Eur J Pharmacol. 449, 135-41, "Chronic vasopressin V(1A) but not V(2) receptor antagonism prevents heart failure in chronically infarcted rats"). Hence, V1a antagonists with improved penetration through the blood-brain barrier are expected to be of advantage.

A vasopressin V1a receptor antagonist was shown to be effective in reducing dysmenorrhea in the clinic (Brouard, et al. (2000). Bjog. 107, 614-9, "Effect of SR49059, an orally active V1a vasopressin receptor antagonist, in the prevention of dysmenorrhoea"). V1a receptor antagonism has also been implicated in the treatment of female sexual dysfunction (Aughton, et al. (2008). Br J Pharmacol. doi:10.1038/bjp.2008.253, "Pharmacological profiling of neuropeptides on rabbit vaginal wall and vaginal artery smooth muscle in vitro"). In a recent study V1a receptor antagonists were suggested to have a therapeutic role in both erectile dysfunction and premature ejaculation (Gupta, et al. (2008). Br J Pharmacol. 155, 118-26, "Oxytocin-induced contractions within rat and rabbit ejaculatory tissues are mediated by vasopressin V(1A) receptors and not oxytocin receptors").

SUMMARY OF THE INVENTION

The present invention provides arylcyclohexylethers of dihydro-tetraazabenzoazulenes, i.e. arylcyclohexylethers of 5,6-dihydro-4H-2,3,5,10b-tetraaza-benzo[e]azulenes, which act as V1a receptor modulators, and in particular as V1a receptor antagonists, their manufacture, pharmaceutical compositions containing them and methods for the treatment of conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

In particular, the present invention is concerned with arylcyclohexylethers of dihydro-tetraazabenzoazulenes of formula I

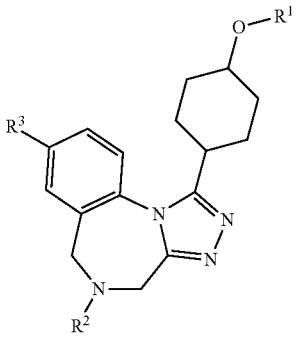

wherein
R$^1$ is aryl or heteroaryl, each of which is unsubstituted or substituted with one or more substituents independently selected from A;
R$^2$ is H,
C$_{1-12}$-alkyl, unsubstituted or substituted with one or more OH, halo, cyano or C$_{1-12}$-alkoxy, —(CH$_2$)$_q$—R$^a$, wherein R$^a$ is phenyl or 5- or 6-membered heteroaryl, each of which is unsubstituted or substituted with one or more substituents independently selected from A,
—(CH$_2$)$_q$NR$^i$R$^{ii}$,
—C(O)—C$_{1-12}$-alkyl, wherein C$_{1-12}$-alkyl is unsubstituted or substituted with one or more OH, halo, cyano or C$_{1-12}$-alkoxy,
—C(O)(CH$_2$)$_q$OC(O)—C$_{1-12}$-alkyl,
—C(O)(CH$_2$)$_q$NR$^i$R$^{ii}$,
—C(O)O—C$_{1-12}$-alkyl, wherein alkyl is unsubstituted or substituted with one or more OH, halo, cyano or C$_{1-12}$-alkoxy,
—S(O)$_2$—C$_{1-12}$-alkyl,
—S(O)$_2$NR$^i$R$^{ii}$, R$^i$ and R$^{ii}$ are each independently H, C$_{1-12}$-alkyl, or together with the nitrogen atom to which they are bound form a 3- to 7-membered heterocycloalkyl containing one or two heteroatoms selected from N, O and S, which heterocycloalkyl is unsubstituted or substituted by one or more substituents independently selected from B,
q is 1, 2, 3 or 4,
r is 2, 3 or 4,
A is halo, cyano, OH, C$_{1-7}$-alkyl, halo-C$_{1-7}$-alkyl, C$_{1-7}$-alkoxy, halo-C$_{1-7}$-alkoxy, or hydroxy-C$_{1-7}$-alkyl,
B is oxo, halo, OH, C$_{1-7}$-alkyl or C$_{1-7}$-alkoxy, and
R$^3$ is Cl or F,
or a pharmaceutically acceptable salt thereof.

DETAILED DESCRIPTION OF THE INVENTION

The present invention provides compounds that act as V1a receptor modulators, and, in particular, as V1a receptor antagonists. The invention further provides selective inhibitors of the V1a receptor since it is expected that selectivity affords a low potential to cause unwanted off-target related side effects such as discussed above.

Such V1a antagonists are useful as therapeutics acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior. The preferred indications with regard to the present invention are the treatment of anxiety, depressive disorders, obsessive compulsive disorder, autistic spectrum disorders, schizophrenia, and aggressive behavior.

The V1a activity can be detected as described in the experimental section.

The following definitions of the general terms used in the present description apply irrespective of whether the terms in question appear alone or in combination.

As used herein, the term "alkyl", alone or in combination with other groups, denotes a saturated, i.e. aliphatic, hydrocarbon group including a straight or branched carbon chain. If not further specified, "alkyl" groups denote groups with 1 to 12 carbon atoms, like "C$_{1-12}$-alkyl". "C$_{1-4}$-alkyl" denotes alkyl groups with 1 to 4 carbon atoms and "C$_{1-7}$-alkyl" denotes alkyl groups with 1 to 7 carbon atoms. Examples for "alkyl" are methyl, ethyl, propyl, isopropyl, n-butyl, iso-butyl, sec-butyl, tert-butyl and the like. Preferred are methyl and tert-butyl.

The term "alkoxy", alone or in combination with other groups, denotes a group —O—R' wherein R' is alkyl as defined above. "C$_{1-12}$-alkoxy" denotes alkoxy groups with 1 to 12 carbon atoms, "C$_{1-4}$-alkoxy" denotes alkoxy groups with 1 to 4 carbon atoms and "C$_{1-7}$-alkoxy" denotes alkoxy groups with 1 to 7 carbon atoms. Examples for "alkoxy" are methoxy, ethoxy, propoxy, tert-butoxy and the like. Preferred is methoxy.

The term "aromatic" means the presence of an electron sextet in a ring, according to Hückel's rule.

The term "aryl", alone or in combination with other groups, denotes a monovalent cyclic aromatic hydrocarbon moiety consisting of a mono- or bicyclic aromatic ring system. Preferred aryl are phenyl or naphthyl. Aryl can be unsubstituted or substituted as described herein.

The term "cyano" denotes the group —CN.
The term "hydroxy" denotes the group —OH.
The term "halo" or "halogen" denotes chloro, iodo, fluoro and bromo.

The term "halo-C$_{1-n}$-alkyl" or "C$_{1-n}$-haloalkyl", alone or in combination with other groups, denotes a C$_{1-n}$-alkyl group as defined above, with 1 to n carbon atoms as defined in the specification, wherein at least one of the hydrogen atoms of the alkyl group is replaced by a halogen atom, preferably fluoro or chloro, most preferably fluoro. Examples of halo-C$_{1-n}$-alkyl include but are not limited to methyl, ethyl, propyl, isopropyl, isobutyl, sec-butyl, tert-butyl, pentyl or n-hexyl substituted by one or more Cl, F, Br or I atom(s), in particular one, two or three fluoro or chloro, as well as those groups specifically illustrated by the examples herein below. Among the preferred halo-C$_{1-n}$-alkyl groups are difluoro- or trifluoro-methyl or -ethyl.

The term "hydroxy-C$_{1-n}$-alkyl" or "C$_{1-n}$-hydroxyalkyl", alone or in combination with other groups, denotes a C$_{1-n}$-alkyl group as defined above, with 1 to n carbon atoms, wherein at least one of the hydrogen atoms of the alkyl group is replaced by a hydroxy, i.e. by an OH group. An example for hydroxyalkyl is hydroxyethyl.

The terms "heteroaryl" and "5- or 6-membered heteroaryl", alone or in combination with other groups, refers to a monovalent 5- or 6-membered aromatic monocyclic or 9- or 10-membered aromatic bicyclic ring system containing from one to four ring heteroatoms selected from N, O, and S, the remaining ring atoms being C. Preferably, the monocyclic heteroaryl bears one or two heteroatoms and the bicyclic heteroaryl bears from one to four heteroatoms. 6-Membered heteroaryl are preferred. Examples for heteroaryl moieties include but are not limited to pyridinyl, pyrimidinyl, pyridazinyl or pyrazinyl. Heteroaryl can be unsubstituted or substituted as described herein.

The term "heterocycloalkyl", alone or in combination with other groups, as defined herein refers to a monovalent 3 to 7 membered or 4 to 7 membered saturated ring containing one or two heteroatoms selected from N, O and S. The term "3- to 7-membered heterocycloalkyl" refers to a monovalent 3 to 7 membered ring containing one or two heteroatoms selected from N, O and S. Examples for heterocycloclakyl moieties are oxetanyl, tetrahydrofuranyl, tetrahydropyranyl, pyrrolidinyl, morpholinyl, thiomorpholinyl, piperidinyl, or piperazinyl. Preferred heterocycloalkyl are oxetanyl and tetrahydrofuranyl. Heterocycloalkyl is optionally substituted as described herein.

The term "oxo" when referring to substituents on heterocycloalkyl means that an oxygen atom is attached to the heterocycloalkyl ring. Thereby, the "oxo" can either replace two hydrogen atoms on a carbon atom, or it can simply be attached to sulfur, so that the sulfur exists in oxidized form, i.e. bearing one or two oxygens like a group —$SO_2$.

When indicating the number of substituents, the term "one or more" means from one substituent to the highest possible number of substitution, i.e. replacement of one hydrogen up to replacement of all hydrogens by substituents. Thereby, one, two or three substituents are preferred. Even more preferred are one or two substituents or one substituent.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like. Preferred is the hydrochloric acid salt.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Preferably it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

"Therapeutically effective amount" means an amount that is effective to prevent, alleviate or ameliorate symptoms of disease or prolong the survival of the subject being treated.

The following table lists abbreviations used within the present document.

TABLE 1

| abbreviations | |
|---|---|
| $(BOC)_2O$ | di-tert-butyl dicarbonate |
| $CH_2Cl_2$ | dichloromethane |

TABLE 1-continued

| abbreviations | |
|---|---|
| $CS_2CO_3$ | caesium carbonate |
| CuI | copper(I) iodide |
| DEAD | diethyl acetylene dicarboxylate |
| DMAP | 4-(dimethylamino)-pyridine |
| DMF | N,N-dimethylformamide |
| EDTA | ethylendiamin-tetraacetate |
| EI | electron ionization |
| $Et_3N$ | triethylamine |
| HEPES | 4-(2-hydroxyethyl)-1-piperazineethanesulfonic acid |
| HPLC | high performance liquid chromatography |
| $K_2CO_3$ | potassium carbonate |
| Lawesson's reagent | 2,4-bis(4-methoxyphenyl)-1,3,2,4-dithiadiphosphetane-2,4-disulfide |
| MeOH | methanol |
| MS | mass spectroscopy |
| NaOH | sodium hydroxide |
| n-BuOH | n-butanol |
| NMR | nuclear magnetic resonance |
| $PPh_3$ | triphenylphosphine |
| RNA | ribonucleic acid |
| RT | room temperature |
| RT-PCR | reverse-transcriptase polymerase chain reaction |
| $SOCl_2$ | thionyl chloride |
| T-BuOK | potassium tert butanolat |
| THF | tetrahydrofurane |
| Tris | aluminium-tris(8-hydroxychinolin |
| $ZnBr_2$ | zinc bromide |

The invention also provides pharmaceutical compositions, methods of using them, and methods of preparing the aforementioned compounds.

The compounds of formula I can contain asymmetric carbon atoms. Accordingly, the present invention includes all stereoisomeric forms of the compounds of formula I, including each of the individual stereoisomer and mixtures thereof, i.e. their individual optical isomers and mixtures thereof. Additional asymmetric centers can be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to comprehend all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

This applies in particular to the arylcyclohexylether-head group (HG) of the compounds of formula I, namely

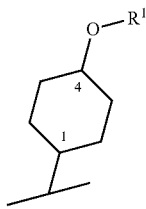

wherein at least the carbon atoms 1 and 4 are asymmetric carbon atoms and $R^1$ could further comprise asymmetric carbon atoms. It is to be understood that present invention includes all individual stereoisomers of head groups and mixtures thereof.

In detail, the present invention provides compounds of formula I

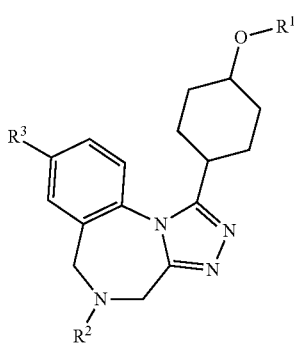

I wherein
$R^1$ is aryl or heteroaryl, each of which is unsubstituted or substituted with one or more substituents independently selected from A;
$R^2$ is H,
  $C_{1-12}$-alkyl, unsubstituted or substituted with one or more OH, halo, cyano or $C_{1-12}$-alkoxy, —$(CH_2)_q$—$R^a$, wherein $R^a$ is phenyl or 5- or 6-membered heteroaryl, each of which is unsubstituted or substituted with one or more substituents independently selected from A,
  —$(CH_2)_r NR^i R^{ii}$,
  —C(O)—$C_{1-12}$-alkyl, wherein $C_{1-12}$-alkyl is unsubstituted or substituted with one or more OH, halo, cyano or $C_{1-12}$-alkoxy,
  —$C(O)(CH_2)_q OC(O)$—$C_{1-12}$-alkyl,
  —$C(O)(CH_2)_q NR^i R^{ii}$,
  —C(O)O—$C_{1-12}$-alkyl, wherein alkyl is unsubstituted or substituted with one or more OH, halo, cyano or $C_{1-12}$-alkoxy,
  —$S(O)_2$—$C_{1-12}$-alkyl, or
  —$S(O)_2 NR^i R^{ii}$, $R^i$ and $R^{ii}$ are each independently H, $C_{1-12}$-alkyl, or together with the nitrogen to which they are bound form a 3- to 7-membered heterocycloalkyl containing one or two heteroatoms selected from N, O and S, which heterocycloalkyl is unsubstituted or substituted by one or more substituents independently selected from B,
q is 1, 2, 3 or 4,
r is 2, 3 or 4,
A is halo, cyano, OH, $C_{1-7}$-alkyl, halo-$C_{1-7}$-alkyl, $C_{1-7}$-alkoxy, halo-$C_{1-7}$-alkoxy, or hydroxy-$C_{1-7}$-alkyl,
B is oxo, halo, OH, $C_{1-7}$-alkyl or $C_{1-7}$-alkoxy, and
$R^3$ is Cl or F,
or a pharmaceutically acceptable salt thereof.

In particular, these head groups HG are

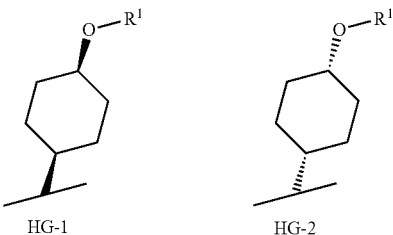

HG-1                    HG-2 trans

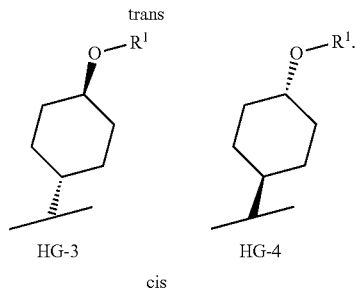

HG-3                    HG-4 cis

It is further understood that all embodiments of the invention as described herein can be combined with each other.

In certain embodiments, A is halo, cyano, OH, $C_{1-7}$-alkyl, halo-$C_{1-7}$-alkyl, $C_{1-7}$-alkoxy, halo-$C_{1-7}$-alkoxy, or hydroxy-$C_{1-7}$-alkyl.

In certain embodiments, A is halo, cyano, $C_{1-7}$-alkyl, halo-$C_{1-7}$-alkyl, or $C_{1-7}$-alkoxy.

In certain embodiments, $R^1$ is aryl or heteroaryl, each of which is unsubstituted or substituted with one or more substituents independently selected from A; and A is as defined above.

In certain embodiments, $R^1$ is a monovalent cyclic aromatic hydrocarbon moiety consisting of a mono- or bicyclic aromatic ring system, a monovalent 5- or 6-membered aromatic monocyclic or 9- or 10-membered aromatic bicyclic ring system containing from one to four ring heteroatoms selected from N, O, and S, the remaining ring atoms being C, each unsubstituted or substituted with one or more substituents independently selected from A; and A is as defined above.

In certain embodiments, $R^1$ is phenyl, naphthyl, pyridinyl, pyrimidinyl, pyridazinyl or pyrazinyl, each unsubstituted or substituted with one or more substituents independently selected from A; and A is as defined above.

In certain embodiments, $R^1$ is phenyl, naphthyl, pyridinyl, pyrimidinyl, pyridazinyl or pyrazinyl, each unsubstituted or substituted with one or more substituents independently selected from methyl, t-butyl, Cl, F, trifluoromethyl, methoxy or cyano.

In certain embodiments, $R^1$ is a monovalent cyclic aromatic hydrocarbon moiety consisting of a mono-aromatic ring.

In certain embodiments, $R^1$ is naphthyl, phenyl, pyrazinyl, pyridazinyl, pyridinyl or pyrimidinyl.

In certain embodiments, $R^1$ is phenyl or pyridinyl.

In certain embodiments, $R^1$ is phenyl, 4-fluoro-phenyl, 4-cyanophenyl, 4-trifluoromethyl-phenyl, 3-chloro-phenyl, 3-methoxy-phenyl, 3-cyano-phenyl, 3-methyl-phenyl, 3-t-butyl-phenyl, 3-trifluoromethyl-phenyl, 2-fluoro-phenyl, 2-cyano-phenyl, 2-methyl-phenyl, 3,5-di-fluoro-phenyl, naphth-2-yl, naphth-1-yl, pyridin-3-yl, 5-chloro-pyridin-3-yl, pyridin-2-yl, 6-chloro-pyridin-2-yl, 3-fluoro-pyridin-2-yl, 5-fluoro-pyridin-2-yl, 6-methyl-pyridin-2-yl, 2,6-di-methyl-pyrimidin-4-yl, pyrimidin-2-yl, pyrazin-2-yl, pyridin-4-yl or pyridazin-3-yl.

In certain embodiments, $R^1$ is phenyl, 4-fluoro-phenyl, 4-cyanophenyl, 4-trifluoromethyl-phenyl, 3-chloro-phenyl, 3-methoxy-phenyl, 3-cyano-phenyl, 3-methyl-phenyl, 3-t-butyl-phenyl, 3-trifluoromethyl-phenyl, 2-fluoro-phenyl, 2-cyano-phenyl, 2-methyl-phenyl, 3,5-di-fluoro-phenyl, naphth-2-yl, naphth-1-yl, pyridin-3-yl, 5-chloro-pyridin-3-yl, pyridin-2-yl, 6-chloro-pyridin-2-yl, 2,6-di-methyl-pyrimidin-4-yl, pyrimidin-2-yl, pyrazin-2-yl, pyridin-4-yl or pyridazin-3-yl.

In certain embodiments, $R^2$ is as described above.

In certain embodiments, $R^2$ is H, forming either the free base or a pharmaceutically acceptable acid addition salt with an inorganic or organic acid such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

In certain embodiments, $R^2$ is $C_{1-12}$-alkyl, unsubstituted or substituted with one or more OH, halo, cyano or $C_{1-12}$-alkoxy. In certain embodiments, $R^2$ is $C_{1-12}$-alkyl, unsubstituted or substituted with one or more OH.

In certain embodiments, $R^2$ is —$(CH_2)_q$—$R^a$, wherein $R^a$ is phenyl or 5- or 6-membered heteroaryl, each of which is unsubstituted or substituted with one or more substituents independently selected from A, and A is as defined above and q is 1, 2, 3 or 4, preferably 1. In certain embodiments, $R^2$ is —$(CH_2)_q$—$R^a$, wherein $R^a$ is phenyl or 5- or 6-membered heteroaryl, each of which is unsubstituted or substituted with one or more substituents independently selected from A, and A is halo, cyano, OH, $C_{1-7}$-alkyl, halo-$C_{1-7}$-alkyl, or $C_{1-7}$-alkoxy; and q is 1, 2, 3 or 4, preferably 1. In certain embodiments, $R^2$ is —$(CH_2)_q$—$R^a$, wherein $R^a$ is phenyl or 5- or 6-membered heteroaryl and q is 1, 2, 3 or 4, preferably 1. In certain embodiments, $R^2$ is —$CH_2$-pyridinyl or benzyl, preferably —$CH_2$-pyridin-2-yl.

In certain embodiments, $R^2$ is —C(O)—$C_{1-12}$-alkyl, wherein alkyl is unsubstituted or substituted with one or more OH, halo, cyano or $C_{1-12}$-alkoxy. In certain embodiments, $R^2$ is —C(O)—$C_{1-12}$-alkyl.

In certain embodiments, $R^2$ is —$C(O)(CH_2)_qNR^iR^{ii}$, wherein q is 1, 2, 3 or 4, preferably 1, and wherein $R^i$ and $R^{ii}$ are each independently H, $C_{1-12}$-alkyl, or together with the nitrogen to which they are bound form a 3- to 7-membered heterocycloalkyl containing one or two heteroatoms selected from N, O and S, which heterocycloalkyl is unsubstituted or substituted by one or more substituents independently selected from B, and B is oxo, halo, OH, $C_{1-7}$-alkyl or $C_{1-7}$-alkoxy. In certain embodiments, $R^2$ is $C(O)(CH_2)_qNR^iR^{ii}$, wherein q is 1, 2, 3 or 4, preferably 1, and wherein $R^i$ and $R^{ii}$ are each independently H or $C_{1-12}$-alkyl, preferably $C_{1-12}$-alkyl.

In certain embodiments, $R^2$ is —C(O)O—$C_{1-12}$-alkyl, wherein alkyl is unsubstituted or substituted with one or more OH, halo, cyano or $C_{1-12}$-alkoxy. In certain embodiments, $R^2$ is —C(O)O—$C_{1-12}$-alkyl.

In certain embodiments, $R^2$ is —$S(O)_2$—$C_{1-12}$-alkyl.

In certain embodiments, $R^2$ is —$S(O)_2NR^iR^{ii}$, wherein $R^i$ and $R^{ii}$ are each independently H, $C_{1-12}$-alkyl, or together with the nitrogen to which they are bound form a 3- to 7-membered heterocycloalkyl containing one or two heteroatoms selected from N, O and S, which heterocycloalkyl is unsubstituted or substituted by one or more substituents independently selected from B, and B is oxo, halo, OH, $C_{1-7}$-alkyl or $C_{1-7}$-alkoxy. In certain embodiments, $R^2$ is —$S(O)_2NR^iR^{ii}$, wherein $R^i$ and $R^{ii}$ are each independently H or $C_{1-12}$-alkyl, preferably $C_{1-12}$-alkyl.

In certain embodiments, $R^2$ is
H,
$C_{1-12}$-alkyl, unsubstituted or substituted with one or more OH or F,
—$(CH_2)_q$—$R^a$, wherein $R^a$ is phenyl or 5- or 6-membered heteroaryl and q is 1, 2, 3 or 4, preferably 1,
—C(O)—$C_{1-12}$-alkyl,
—$C(O)(CH_2)_qNR^iR^{ii}$, wherein $R^i$ and $R^{ii}$ are each independently H or $C_{1-12}$-alkyl, preferably $C_{1-12}$-alkyl, and q is 1, 2, 3 or 4, preferably 1,
—C(O)O—$C_{1-12}$-alkyl,
—$S(O)_2$—$C_{1-12}$-alkyl, or
—$S(O)_2NR^iR^{ii}$, wherein $R^i$ and $R^{ii}$ are each independently H or $C_{1-12}$-alkyl, preferably $C_{1-12}$-alkyl.

In certain embodiments, $R^2$ is
H,
$C_{1-12}$-alkyl, unsubstituted or substituted with one or more OH,
—$(CH_2)_q$—$R^a$, wherein $R^a$ is phenyl or 5- or 6-membered heteroaryl and q is 1, 2, 3 or 4, preferably 1,
—$C(O)(CH_2)_qNR^iR^{ii}$, wherein $R^i$ and $R^{ii}$ are each independently H or $C_{1-12}$-alkyl, preferably $C_{1-12}$-alkyl, and q is 1, 2, 3 or 4, preferably 1,
—$S(O)_2$—$C_{1-12}$-alkyl, or
—$S(O)_2NR^iR^{ii}$, wherein $R^i$ and $R^{ii}$ are each independently H or $C_{1-12}$-alkyl, preferably $C_{1-12}$-alkyl.

In certain embodiments, $R^2$ is 2-hydroxy-ethyl, 2-fluoro-ethyl, 2,2-difluoro-ethyl, —$C(O)CH_2N(Me)_2$, —C(O)methyl, —$CH_2$-pyridin-2-yl, —COO-t-butyl, H, i-propyl, methyl, —$S(O)_2$-methyl or —$S(O)_2N(methyl)_2$.

In certain embodiments, $R^2$ is 2-hydroxy-ethyl, —$C(O)CH_2N(Me)_2$, —C(O)methyl, —$CH_2$-pyridin-2-yl, —COO-t-butyl, H, i-propyl, methyl, —$S(O)_2$-methyl or —$S(O)_2N(methyl)_2$.

In a certain embodiment, $R^3$ is Cl or F. In a certain embodiment, $R^3$ is Cl.

In a certain embodiment of the invention, the compound of formula I is provided

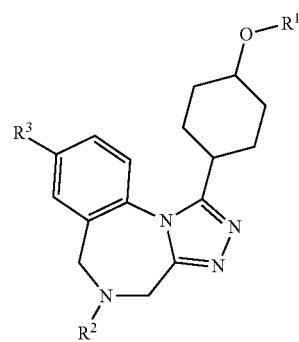

wherein
$R^1$ is a monovalent cyclic aromatic hydrocarbon moiety consisting of a mono- or bicyclic aromatic ring system, a monovalent 5- or 6-membered aromatic monocyclic or 9- or 10-membered aromatic bicyclic ring system containing from one to four ring heteroatoms selected from N, O, and S, the remaining ring atoms being C, each unsubstituted or substituted with one or more substituents independently selected from A;

$R^2$ is H, $C_{1-12}$-alkyl, unsubstituted or substituted with one or more OH,

—$(CH_2)_q$—$R^a$, wherein $R^a$ is phenyl or 5- or 6-membered heteroaryl and q is 1, 2, 3 or 4, preferably 1, —C(O)—$C_{1-12}$-alkyl, —C(O)$(CH_2)_q$$NR^iR^{ii}$, wherein $R^i$ and $R^{ii}$ are each independently H or $C_{1-12}$-alkyl, preferably $C_{1-12}$-alkyl, and q is 1, 2, 3 or 4, preferably 1, —C(O)O—$C_{1-12}$-alkyl, —$S(O)_2$—$C_{1-12}$-alkyl, or —$S(O)_2NR^iR^{ii}$, wherein $R^i$ and $R^{ii}$ are each independently H or $C_{1-12}$-alkyl, preferably $C_{1-12}$-alkyl, $R^3$ is Cl or F, and A is halo, cyano, OH, $C_{1-7}$-alkyl, halo-$C_{1-7}$-alkyl, or $C_{1-7}$-alkoxy, or a pharmaceutically acceptable salt thereof.

In a certain embodiment of the invention, the compound of formula I is provided as a subset of formula I'

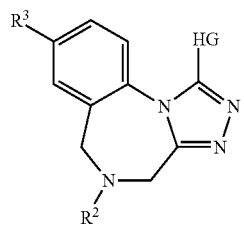

wherein HG is selected from

HG-1

HG-2

HG-3

HG-4

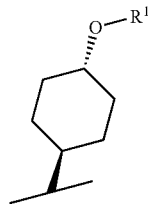

and $R^1$, $R^2$ and $R^3$ are as described above, including all combinations thereof.

Examples for the compound according to the invention are shown in the experimental part and the table below.

TABLE 2

| structures of selected samples | |
|---|---|
| Ex | Structure |
| 1 | |
| 2 | |
| 3 | |

TABLE 2-continued structures of selected samples

| Ex | Structure |
|---|---|
| 4 | (phenoxy-cyclohexyl triazolo-benzodiazepine with Cl and N-acetyl) |
| 5 | (phenoxy-cyclohexyl triazolo-benzodiazepine with Cl and N-methylsulfonyl) |
| 6 | (phenoxy-cyclohexyl triazolo-benzodiazepine with Cl and N-(2-hydroxyethyl)) |
| 7 | (phenoxy-cyclohexyl triazolo-benzodiazepine with Cl and N-isopropyl) |
| 8 | (phenoxy-cyclohexyl triazolo-benzodiazepine with Cl and N,N-dimethylsulfamoyl) |
| 9 | (phenoxy-cyclohexyl triazolo-benzodiazepine with Cl and N-(pyridin-2-ylmethyl)) |
| 10 | (phenoxy-cyclohexyl triazolo-benzodiazepine with Cl and N-(2-(dimethylamino)acetyl)) |

TABLE 2-continued structures of selected samples

| Ex | Structure |
|----|-----------|
| 11 | 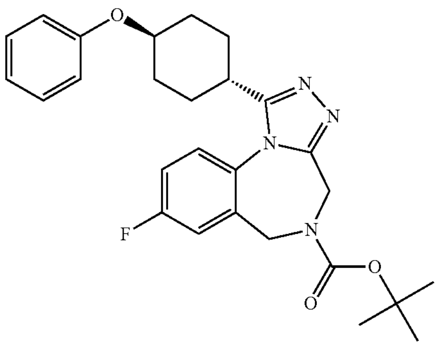 [SMILES: CC(C)(C)OC(=O)N1Cc2cc(F)ccc2-n2c(nnc2[C@H]2CC[C@H](Oc3ccccc3)CC2)C1] |
| 12 | 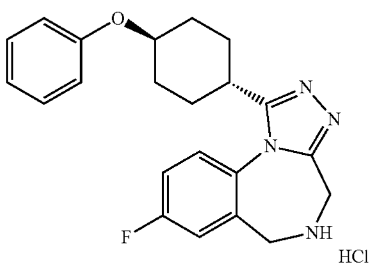 [SMILES: Fc1ccc2c(c1)CNCc1nnc([C@H]3CC[C@H](Oc4ccccc4)CC3)n1-2 ; Cl] |
| 13 | 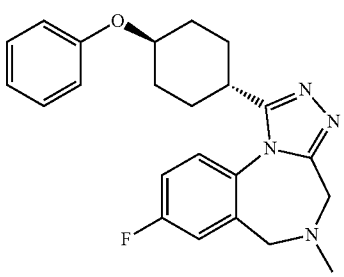 [SMILES: CN1Cc2cc(F)ccc2-n2c(nnc2[C@H]2CC[C@H](Oc3ccccc3)CC2)C1] |
| 14 | 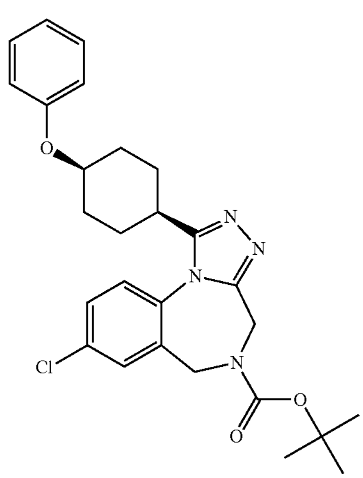 [SMILES: CC(C)(C)OC(=O)N1Cc2cc(Cl)ccc2-n2c(nnc2[C@H]2CC[C@@H](Oc3ccccc3)CC2)C1] |
| 15 | |
| 16 | |
| 17 | |

TABLE 2-continued structures of selected samples

| Ex | Structure |
|---|---|
| 18 | 4-fluorophenoxy-cyclohexyl-triazolo-benzodiazepine with Cl, NH, HCl |
| 19 | 4-fluorophenoxy-cyclohexyl-triazolo-benzodiazepine with Cl, N-methyl |
| 20 | 4-cyanophenoxy-cyclohexyl-triazolo-benzodiazepine with Cl, N-Boc |
| 21 | 4-cyanophenoxy-cyclohexyl-triazolo-benzodiazepine with Cl, NH, HCl |
| 22 | 4-cyanophenoxy-cyclohexyl-triazolo-benzodiazepine with Cl, N-methyl |
| 23 | 4-trifluoromethylphenoxy-cyclohexyl-triazolo-benzodiazepine with Cl, N-Boc |
| 24 | 4-trifluoromethylphenoxy-cyclohexyl-triazolo-benzodiazepine with Cl, NH, HCl |
| 25 | 4-trifluoromethylphenoxy-cyclohexyl-triazolo-benzodiazepine with Cl, N-methyl |
| 26 | 3-chlorophenoxy-cyclohexyl-triazolo-benzodiazepine with Cl, N-Boc |

TABLE 2-continued structures of selected samples

| Ex | Structure |
|---|---|
| 27 | (3-chlorophenoxy cyclohexyl triazolo benzodiazepine with Cl on benzene, NH, HCl) |
| 28 | (3-chlorophenoxy cyclohexyl triazolo benzodiazepine with Cl, N-methyl) |
| 29 | (3-methoxyphenoxy cyclohexyl triazolo benzodiazepine with Cl, N-Boc) |
| 30 | (3-methoxyphenoxy cyclohexyl triazolo benzodiazepine with Cl, NH, HCl) |
| 31 | (3-methoxyphenoxy cyclohexyl triazolo benzodiazepine with Cl, N-methyl) |
| 32 | (3-cyanophenoxy cyclohexyl triazolo benzodiazepine with Cl, N-Boc) |
| 33 | (3-cyanophenoxy cyclohexyl triazolo benzodiazepine with Cl, NH, HCl) |
| 34 | (3-cyanophenoxy cyclohexyl triazolo benzodiazepine with Cl, N-methyl) |
| 35 | (3-methylphenoxy cyclohexyl triazolo benzodiazepine with Cl, N-Boc) |
| 36 | (3-methylphenoxy cyclohexyl triazolo benzodiazepine with Cl, NH, HCl) |

TABLE 2-continued structures of selected samples

| Ex | Structure |
|---|---|
| 37 | 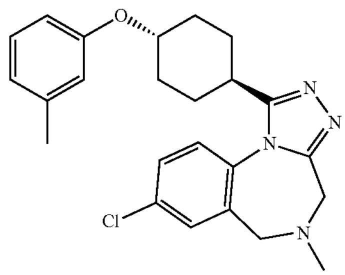 [SMILES: Cc1cccc(O[C@H]2CC[C@H](c3nnc4n3-c3ccc(Cl)cc3CN(C)C4)CC2)c1] |
| 38 | 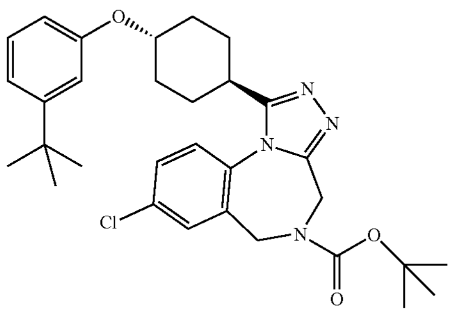 [SMILES: CC(C)(C)OC(=O)N1Cc2cc(Cl)ccc2-n2c(nnc2[C@H]2CC[C@H](Oc3cccc(C(C)(C)C)c3)CC2)C1] |
| 39 | 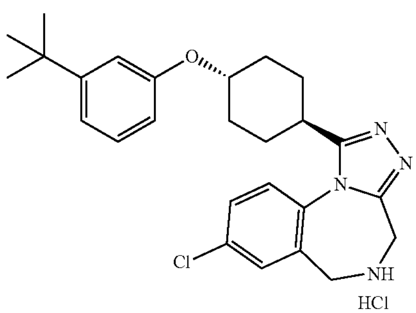 [SMILES: CC(C)(C)c1cccc(O[C@H]2CC[C@H](c3nnc4n3-c3ccc(Cl)cc3CNC4)CC2)c1 ; Cl] |
| 40 | 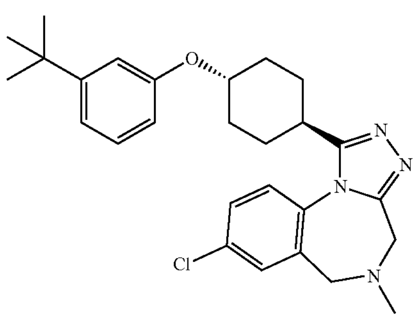 [SMILES: CN1Cc2cc(Cl)ccc2-n2c(nnc2[C@H]2CC[C@H](Oc3cccc(C(C)(C)C)c3)CC2)C1] |
| 41 | 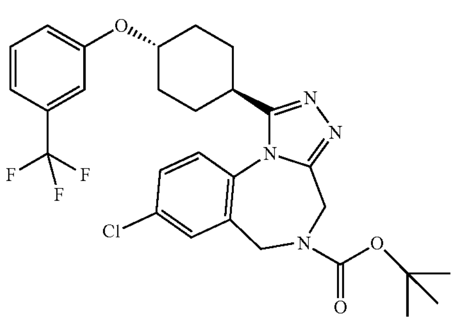 [SMILES: CC(C)(C)OC(=O)N1Cc2cc(Cl)ccc2-n2c(nnc2[C@H]2CC[C@H](Oc3cccc(C(F)(F)F)c3)CC2)C1] |
| 42 | |
| 43 | |
| 44 | |
| 45 | |

TABLE 2-continued structures of selected samples

| Ex | Structure |
|---|---|
| 46 | (structure) |
| 47 | (structure) |
| 48 | (structure) |
| 49 | (structure) |
| 50 | (structure) |
| 51 | (structure) |
| 52 | (structure) |
| 53 | (structure) |
| 54 | (structure) |

TABLE 2-continued structures of selected samples

| Ex | Structure |
|---|---|
| 55 | (2-naphthyloxy-cyclohexyl-triazolo-chlorobenzodiazepine, N-Boc) |
| 56 | (2-naphthyloxy-cyclohexyl-triazolo-chlorobenzodiazepine, NH·HCl) |
| 57 | (2-naphthyloxy-cyclohexyl-triazolo-chlorobenzodiazepine, N-Me) |
| 58 | (1-naphthyloxy-cyclohexyl-triazolo-chlorobenzodiazepine, N-Boc) |
| 59 | (1-naphthyloxy-cyclohexyl-triazolo-chlorobenzodiazepine, NH·HCl) |
| 60 | (1-naphthyloxy-cyclohexyl-triazolo-chlorobenzodiazepine, N-Me) |
| 61 | (pyridin-3-yloxy-cyclohexyl-triazolo-chlorobenzodiazepine, N-Boc) |
| 62 | (pyridin-3-yloxy-cyclohexyl-triazolo-chlorobenzodiazepine, NH·HCl) |
| 63 | (pyridin-3-yloxy-cyclohexyl-triazolo-chlorobenzodiazepine, N-Me) |

TABLE 2-continued structures of selected samples

| Ex | Structure |
|---|---|
| 64 | 5-chloro-pyridin-3-yloxy cyclohexyl triazolo benzodiazepine with Cl and N-Boc |
| 65 | 5-chloro-pyridin-3-yloxy cyclohexyl triazolo benzodiazepine with Cl and NH·HCl |
| 66 | 5-chloro-pyridin-3-yloxy cyclohexyl triazolo benzodiazepine with Cl and N-Me |
| 67 | pyridin-2-yloxy cyclohexyl triazolo benzodiazepine with Cl and N-Boc |
| 68 | pyridin-2-yloxy cyclohexyl triazolo benzodiazepine with Cl and NH·HCl |
| 69 | pyridin-2-yloxy cyclohexyl triazolo benzodiazepine with Cl and N-Me |
| 70 | 6-chloro-pyridin-2-yloxy cyclohexyl triazolo benzodiazepine with Cl and N-Boc |
| 71 | 6-chloro-pyridin-2-yloxy cyclohexyl triazolo benzodiazepine with Cl and NH·HCl |
| 72 | 6-chloro-pyridin-2-yloxy cyclohexyl triazolo benzodiazepine with Cl and N-Me |
| 73 | 5-chloro-pyridin-2-yloxy cyclohexyl triazolo benzodiazepine with Cl and N-Boc |

TABLE 2-continued structures of selected samples

| Ex | Structure |
|---|---|
| 74 | (5-chloropyridin-2-yl)oxy-cyclohexyl triazolo benzodiazepine, Cl on benzo ring, NH, HCl |
| 75 | (5-chloropyridin-2-yl)oxy-cyclohexyl triazolo benzodiazepine, Cl on benzo ring, N-methyl |
| 76 | (2,6-dimethylpyrimidin-4-yl)oxy-cyclohexyl triazolo benzodiazepine, Cl on benzo ring, N-Boc |
| 77 | (2,6-dimethylpyrimidin-4-yl)oxy-cyclohexyl triazolo benzodiazepine, Cl on benzo ring, NH, HCl |
| 78 | (2,6-dimethylpyrimidin-4-yl)oxy-cyclohexyl triazolo benzodiazepine, Cl on benzo ring, N-methyl |
| 79 | (pyrimidin-2-yl)oxy-cyclohexyl triazolo benzodiazepine, Cl on benzo ring, N-Boc |
| 80 | (pyrimidin-2-yl)oxy-cyclohexyl triazolo benzodiazepine, Cl on benzo ring, N-Boc |
| 81 | (pyrimidin-2-yl)oxy-cyclohexyl triazolo benzodiazepine, Cl on benzo ring, NH |
| 82 | (pyrimidin-2-yl)oxy-cyclohexyl triazolo benzodiazepine, Cl on benzo ring, N-methyl |
| 83 | (pyrazin-2-yl)oxy-cyclohexyl triazolo benzodiazepine, Cl on benzo ring, N-Boc |

TABLE 2-continued structures of selected samples

| Ex | Structure |
|----|-----------|
| 84 | 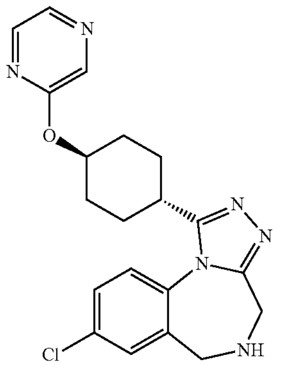 [SMILES: Clc1ccc2c(c1)CNCc1nnc([C@H]3CC[C@H](Oc4cnccn4)CC3)n1-2] |
| 85 | 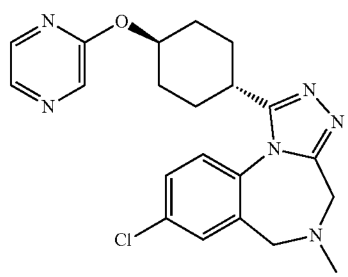 [SMILES: CN1Cc2cc(Cl)ccc2-n2c(nnc2[C@H]2CC[C@H](Oc3cnccn3)CC2)C1] |
| 86 | 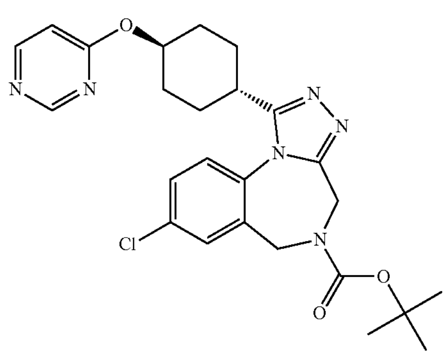 [SMILES: CC(C)(C)OC(=O)N1Cc2cc(Cl)ccc2-n2c(nnc2[C@H]2CC[C@H](Oc3ccncn3)CC2)C1] |
| 87 | 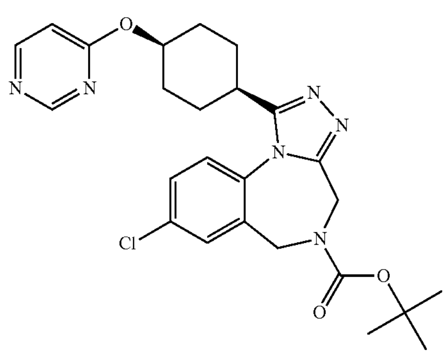 [SMILES: CC(C)(C)OC(=O)N1Cc2cc(Cl)ccc2-n2c(nnc2[C@H]2CC[C@@H](Oc3ccncn3)CC2)C1] |
| 88 | 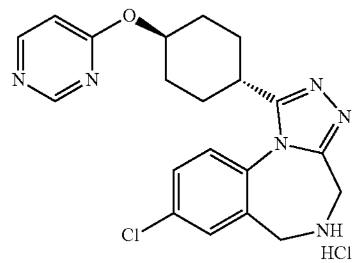 [SMILES: Clc1ccc2c(c1)CNCc1nnc([C@H]3CC[C@H](Oc4ccncn4)CC3)n1-2 ; Cl] |
| 89 | 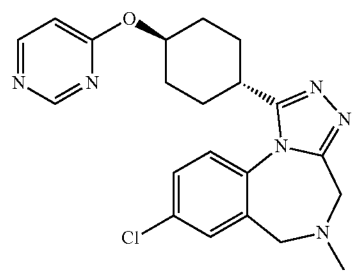 [SMILES: CN1Cc2cc(Cl)ccc2-n2c(nnc2[C@H]2CC[C@H](Oc3ccncn3)CC2)C1] |
| 90 | 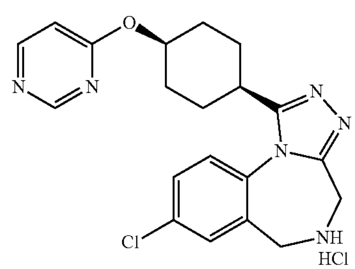 [SMILES: Clc1ccc2c(c1)CNCc1nnc([C@H]3CC[C@@H](Oc4ccncn4)CC3)n1-2 ; Cl] |
| 91 | 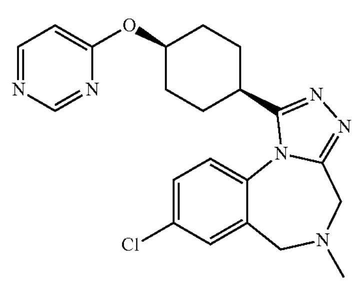 [SMILES: CN1Cc2cc(Cl)ccc2-n2c(nnc2[C@H]2CC[C@@H](Oc3ccncn3)CC2)C1] |
| 92 | 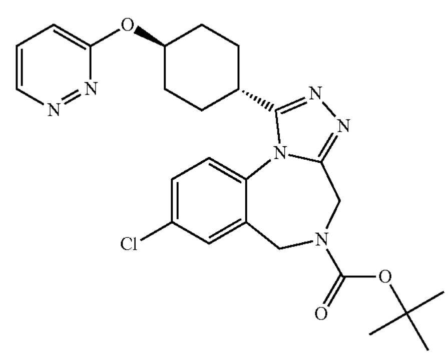 [SMILES: CC(C)(C)OC(=O)N1Cc2cc(Cl)ccc2-n2c(nnc2[C@H]2CC[C@H](Oc3cccnn3)CC2)C1] |

TABLE 2-continued structures of selected samples

| Ex | Structure |
|---|---|
| 93 | 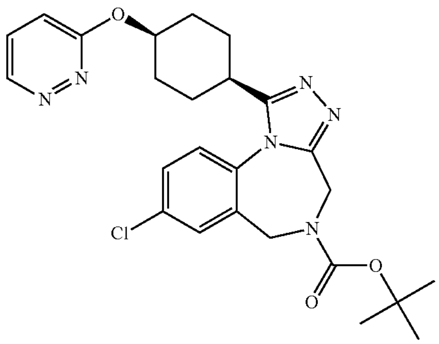 [SMILES: CC(C)(C)OC(=O)N1Cc2cc(Cl)ccc2-n2c(nnc2[C@H]2CC[C@@H](Oc3cccnn3)CC2)C1] |
| 94 | 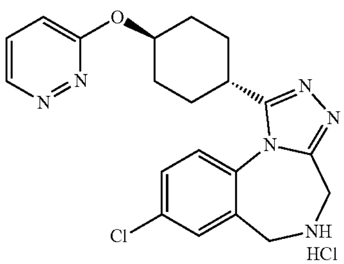 [SMILES: Clc1ccc2c(c1)CNCc1nnc([C@H]3CC[C@H](Oc4cccnn4)CC3)n1-2 ; Cl] |
| 95 | 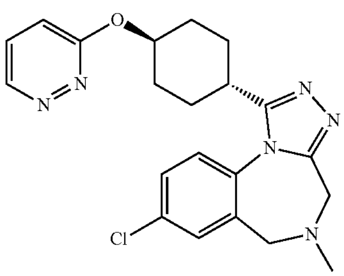 [SMILES: CN1Cc2cc(Cl)ccc2-n2c(nnc2[C@H]2CC[C@H](Oc3cccnn3)CC2)C1] |
| 96 | 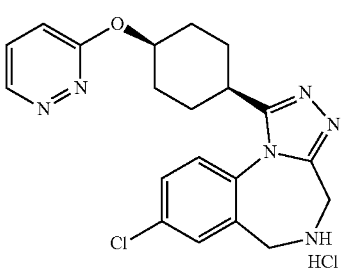 [SMILES: Clc1ccc2c(c1)CNCc1nnc([C@H]3CC[C@@H](Oc4cccnn4)CC3)n1-2 ; Cl] |
| 97 | 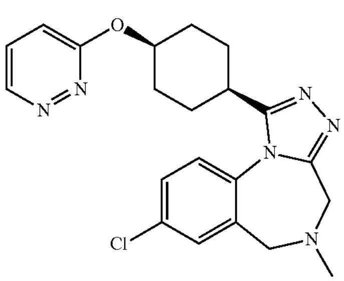 [SMILES: CN1Cc2cc(Cl)ccc2-n2c(nnc2[C@H]2CC[C@@H](Oc3cccnn3)CC2)C1] |
| 98 | |
| 99 | |
| 100 | |
| 101 | |
| 102 | |

TABLE 2-continued structures of selected samples

| Ex | Structure |
|---|---|
| 103 | 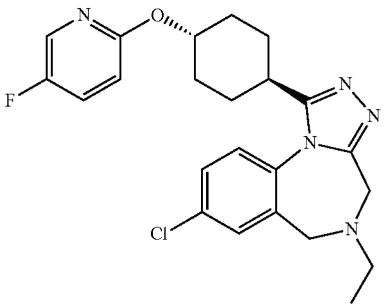 [SMILES: CCN1Cc2cc(Cl)ccc2-n2c(nnc2[C@H]2CC[C@H](Oc3ccc(F)cn3)CC2)C1] |
| 104 | 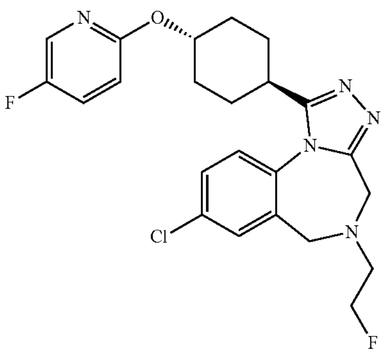 [SMILES: FCCN1Cc2cc(Cl)ccc2-n2c(nnc2[C@H]2CC[C@H](Oc3ccc(F)cn3)CC2)C1] |
| 105 | 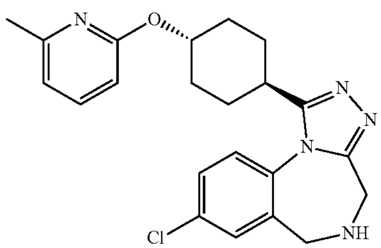 [SMILES: Cc1cccc(O[C@H]2CC[C@H](c3nnc4n3-c3ccc(Cl)cc3CNC4)CC2)n1] |
| 106 | 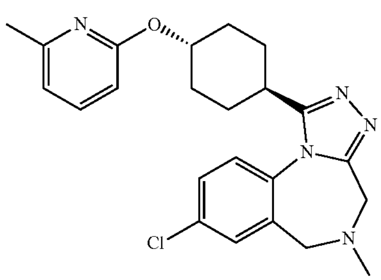 [SMILES: Cc1cccc(O[C@H]2CC[C@H](c3nnc4n3-c3ccc(Cl)cc3CN(C)C4)CC2)n1] |
| 107 | 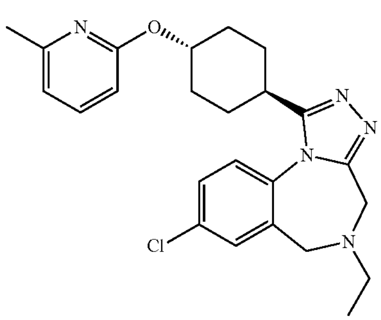 [SMILES: CCN1Cc2cc(Cl)ccc2-n2c(nnc2[C@H]2CC[C@H](Oc3cccc(C)n3)CC2)C1] |
| 108 | 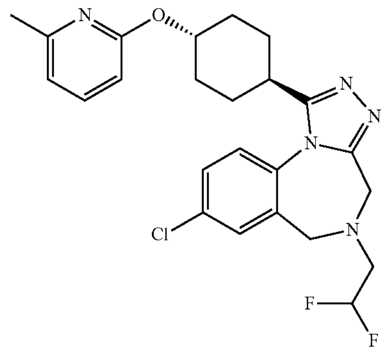 [SMILES: Cc1cccc(O[C@H]2CC[C@H](c3nnc4n3-c3ccc(Cl)cc3CN(CC(F)F)C4)CC2)n1] |
| 109 | 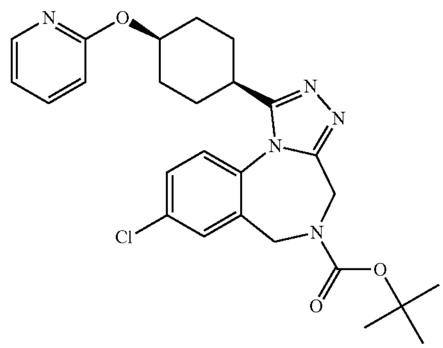 [SMILES: CC(C)(C)OC(=O)N1Cc2cc(Cl)ccc2-n2c(nnc2[C@H]2CC[C@@H](Oc3ccccn3)CC2)C1] |
| 110 | 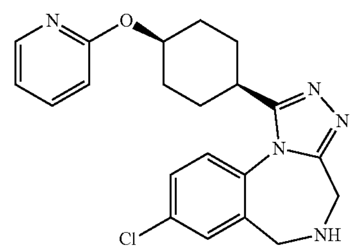 [SMILES: Clc1ccc2c(c1)CNCc1nnc([C@H]3CC[C@@H](Oc4ccccn4)CC3)n1-2] |
| 111 | 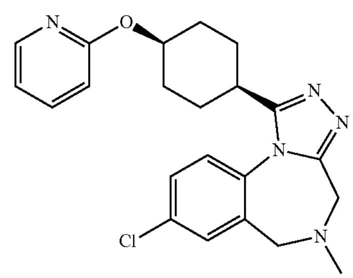 [SMILES: CN1Cc2cc(Cl)ccc2-n2c(nnc2[C@H]2CC[C@@H](Oc3ccccn3)CC2)C1] |

Preferred compounds of the invention are shown in the examples. Particularly preferred are
trans-8-Chloro-1-(4-phenoxy-cyclohexyl)-4H,6H-2,3,5,10b-tetraaza-benzoazulene-5-carboxylic acid tert-butyl ester,
trans-8-Chloro-1-(4-phenoxy-cyclohexyl)-5,6-dihydro-4H-2,3,5,10b-tetraaza-benzoazulene hydrochloride,
trans-8-Chloro-5-methyl-1-(4-phenoxy-cyclohexyl)-5,6-dihydro-4H-2,3,5,10b-tetraaza-benzo[e]azulene,
trans-1-[8-Chloro-1-(4-phenoxy-cyclohexyl)-4H,6H-2,3,5,10b-tetraaza-benzoazulen-5-yl]-ethanone,
trans-8-Chloro-5-methanesulfonyl-1-(4-phenoxy-cyclohexyl)-5,6-dihydro-4H-2,3,5,10b-tetraaza-benzoazulene, trans-2-[8-Chloro-1-(4-phenoxy-cyclohexyl)-4H,6H-2,3,5,10b-tetraaza-benzoazulen-5-yl]-ethanol, trans-8-Chloro-5-isopropyl-1-(4-phenoxy-cyclohexyl)-5,6-dihydro-4H-2,3,5,10b-tetraaza-benzoazulene, trans-8-Chloro-1-(4-phenoxy-cyclohexyl)-4H,6H-2,3,5,10b-tetraaza-benzoazulene-5-sulfonic acid dimethylamide, trans-8-Chloro-1-(4-phenoxy-cyclohexyl)-5-pyridin-2-ylmethyl-5,6-dihydro-4H-2,3,5,10b-tetraaza-benzo azulene, trans-1-[8-Chloro-1-(4-phenoxy-cyclohexyl)-4H,6H-2,3,5,10b-tetraaza-benzoazulen-5-yl]-2-dimethylamino-ethanone, trans-8-Fluoro-1-(4-phenoxy-cyclohexyl)-4H,6H-2,3,5,10b-tetraaza-benzo[e]azulene-5-carboxylic acid tert-butyl ester, trans-8-Fluoro-5-methyl-1-(4-phenoxy-cyclohexyl)-5,6-dihydro-4H-2,3,5,10b-tetraaza-benzoazulene, cis-8-Chloro-1-(4-phenoxy-cyclohexyl)-4H,6H-2,3,5,10b-tetraaza-benzo azulene-5-carboxylic acid tert-butyl ester, cis-8-Chloro-5-methyl-1-(4-phenoxy-cyclohexyl)-5,6-dihydro-4H-2,3,5,10b-tetraaza-benzoazulene, trans-8-Chloro-1-[4-(4-fluoro-phenoxy)-cyclohexyl]-4H,6H-2,3,5,10b-tetraaza-benzo azulene-5-carboxylic acid tert-butyl ester, trans-8-Chloro-1-[4-(4-fluoro-phenoxy)-cyclohexyl]-5,6-dihydro-4H-2,3,5,10b-tetraaza-benzo[e]azulene hydrochloride, trans-8-Chloro-1-[4-(4-fluoro-phenoxy)-cyclohexyl]-5-methyl-5,6-dihydro-4H-2,3,5,10b-tetraaza-benzo azulene, trans-8-Chloro-1-[4-(4-cyano-phenoxy)-cyclohexyl]-4H,6H-2,3,5,10b-tetraaza-benzo[e]azulene-5-carboxylic acid tert-butyl ester, trans-4-[4-(8-Chloro-5-methyl-5,6-dihydro-4H-2,3,5,10b-tetraaza-benzo[e]azulen-1-yl)-cyclohexyloxy]-benzonitrile, trans-8-Chloro-1-[4-(4-trifluoromethyl-phenoxy)-cyclohexyl]-4H,6H-2,3,5,10b-tetraaza-benzo[e]azulene-5-carboxylic acid tert-butyl ester, trans-8-Chloro-1-[4-(3-chloro-phenoxy)-cyclohexyl]-4H,6H-2,3,5,10b-tetraaza-benzoazulene-5-carboxylic acid tert-butyl ester, trans-8-Chloro-1-[4-(3-chloro-phenoxy)-cyclohexyl]-5-methyl-5,6-dihydro-4H-2,3,5,10b-tetraaza-benzoazulene, trans-8-Chloro-1-[4-(3-methoxy-phenoxy)-cyclohexyl]-4H,6H-2,3,5,10b-tetraaza-benzoazulene-5-carboxylic acid tert-butyl ester, trans-8-Chloro-1-[4-(3-methoxy-phenoxy)-cyclohexyl]-5,6-dihydro-4H-2,3,5,10b-tetraaza-benzo[e]azulene hydrochloride, trans-8-Chloro-1-[4-(3-methoxy-phenoxy)-cyclohexyl]-5-methyl-5,6-dihydro-4H-2,3,5,10b-tetraaza-benzoazulene, trans-3-[4-(8-Chloro-5-methyl-5,6-dihydro-4H-2,3,5,10b-tetraaza-benzoazulen-1-yl)-cyclohexyloxy]-benzonitrile, trans-8-Chloro-1-(4-m-tolyloxy-cyclohexyl)-4H,6H-2,3,5,10b-tetraaza-benzo[e]azulene-5-carboxylic acid tert-butyl ester, trans-8-Chloro-1-(4-m-tolyloxy-cyclohexyl)-5,6-dihydro-4H-2,3,5,10b-tetraaza-benzo[e]azulene hydrochloride, trans-8-Chloro-5-methyl-1-(4-m-tolyloxy-cyclohexyl)-5,6-dihydro-4H-2,3,5,10b-tetraaza-benzo[e]azulene, trans-1-[4-(3-tert-Butyl-phenoxy)-cyclohexyl]-8-chloro-4H,6H-2,3,5,10b-tetraaza-benzo[e]azulene-5-carboxylic acid tert-butyl ester, trans-8-Chloro-1-[4-(2-fluoro-phenoxy)-cyclohexyl]-4H,6H-2,3,5,10b-tetraaza-benzo[e]azulene-5-carboxylic acid tert-butyl ester, trans-8-Chloro-1-[4-(2-fluoro-phenoxy)-cyclohexyl]-5,6-dihydro-4H-2,3,5,10b-tetraaza-benzo[e]azulene hydrochloride, trans-8-Chloro-1-[4-(2-fluoro-phenoxy)-cyclohexyl]-5-methyl-5,6-dihydro-4H-2,3,5,10b-tetraaza-benzo[e]azulene, trans-8-Chloro-1-[4-(2-cyano-phenoxy)-cyclohexyl]-4H,6H-2,3,5,10b-tetraaza-benzoazulene-5-carboxylic acid tert-butyl ester, trans-2-[4-(8-Chloro-5,6-dihydro-4H-2,3,5,10b-tetraaza-benzo[e]azulen-1-yl)-cyclohexyloxy]-benzonitrile hydrochloride, trans-2-[4-(8-Chloro-5-methyl-5,6-dihydro-4H-2,3,5,10b-tetraaza-benzoazulen-1-yl)-cyclohexyloxy]-benzonitrile, trans-8-Chloro-1-(4-o-tolyloxy-cyclohexyl)-4H,6H-2,3,5,10b-tetraaza-benzoazulene-5-carboxylic acid tert-butyl ester, trans-8-Chloro-5-methyl-1-(4-o-tolyloxy-cyclohexyl)-5,6-dihydro-4H-2,3,5,10b-tetraaza-benzoazulene, trans-8-Chloro-1-[4-(3,5-difluoro-phenoxy)-cyclohexyl]-4H,6H-2,3,5,10b-tetraaza-benzoazulene-5-carboxylic acid tert-butyl ester, trans-8-Chloro-1-[4-(3,5-difluoro-phenoxy)-cyclohexyl]-5-methyl-5,6-dihydro-4H-2,3,5,10b-tetraaza-benzoazulene, trans-8-Chloro-1-[4-(naphthalen-2-yloxy)-cyclohexyl]-4H,6H-2,3,5,10b-tetraaza-benzoazulene-5-carboxylic acid tert-butyl ester, trans-8-Chloro-5-methyl-1-[4-(naphthalen-2-yloxy)-cyclohexyl]-5,6-dihydro-4H-2,3,5,10b-tetraaza-benzoazulene, trans-8-Chloro-1-[4-(pyridin-3-yloxy)-cyclohexyl]-4H,6H-2,3,5,10b-tetraaza-benzoazulene-5-carboxylic acid tert-butyl ester, trans-8-Chloro-5-methyl-1-[4-(pyridin-3-yloxy)-cyclohexyl]-5,6-dihydro-4H-2,3,5,10b-tetraaza-benzoazulene, trans-8-Chloro-1-[4-(5-chloro-pyridin-3-yloxy)-cyclohexyl]-4H,6H-2,3,5,10b-tetraaza-benzoazulene-5-carboxylic acid tert-butyl ester, trans-8-Chloro-1-[4-(5-chloro-pyridin-3-yloxy)-cyclohexyl]-5-methyl-5,6-dihydro-4H-2,3,5,10b-tetraaza-benzoazulene, trans-8-Chloro-1-[4-(pyridin-2-yloxy)-cyclohexyl]-4H,6H-2,3,5,10b-tetraaza-benzoazulene-5-carboxylic acid tert-butyl ester, trans-8-Chloro-1-[4-(pyridin-2-yloxy)-cyclohexyl]-5,6-dihydro-4H-2,3,5,10b-tetraaza-benzoazulene hydrochloride, trans-8-Chloro-5-methyl-1-[4-(pyridin-2-yloxy)-cyclohexyl]-5,6-dihydro-4H-2,3,5,10b-tetraaza-benzoazulene, trans-8-Chloro-1-[4-(6-chloro-pyridin-2-yloxy)-cyclohexyl]-4H,6H-2,3,5,10b-tetraaza-benzo[e]azulene-5-carboxylic acid tert-butyl ester, trans-8-Chloro-1-[4-(6-chloro-pyridin-2-yloxy)-cyclohexyl]-5-methyl-5,6-dihydro-4H-2,3,5,10b-tetraaza-benzo[e]azulene, trans-8-Chloro-1-[4-(5-chloro-pyridin-2-yloxy)-cyclohexyl]-5,6-dihydro-4H-2,3,5,10b-tetraaza-benzo[e]azulene hydrochloride, trans-8-Chloro-1-[4-(5-chloro-pyridin-2-yloxy)-cyclohexyl]-5-methyl-5,6-dihydro-4H-2,3,5,10b-tetraaza-benzo[e]azulene, trans-8-Chloro-1-[4-(pyrimidin-2-yloxy)-cyclohexyl]-4H,6H-2,3,5,10b-tetraaza-benzo[e]azulene-5-carboxylic acid tert-butyl ester, cis-8-Chloro-1-[4-(pyrimidin-2-yloxy)-cyclohexyl]-4H,6H-2,3,5,10b-tetraaza-benzo[e]azulene-5-carboxylic acid tert-butyl ester, trans-8-Chloro-5-methyl-1-[4-(pyrimidin-2-yloxy)-cyclohexyl]-5,6-dihydro-4H-2,3,5,10b-tetraaza-benzo[e]azulene,
trans-8-Chloro-1-[4-(pyrazin-2-yloxy)-cyclohexyl]-4H,6H-2,3,5,10b-tetraaza-benzo[e]azulene-5-carboxylic acid tert-butyl ester,
trans-8-Chloro-5-methyl-1-[4-(pyrazin-2-yloxy)-cyclohexyl]-5,6-dihydro-4H-2,3,5,10b-tetraaza-benzo[e]azulene,
trans-8-Chloro-1-[4-(pyrimidin-4-yloxy)-cyclohexyl]-4H,6H-2,3,5,10b-tetraaza-benzo[e]azulene-5-carboxylic acid tert-butyl ester,
trans-8-Chloro-5-methyl-1-[4-(pyrimidin-4-yloxy)-cyclohexyl]-5,6-dihydro-4H-2,3,5,10b-tetraaza-benzo[e]azulene,
trans-8-Chloro-1-[4-(pyridazin-3-yloxy)-cyclohexyl]-4H,6H-2,3,5,10b-tetraaza-benzo[e]azulene-5-carboxylic acid tert-butyl ester,
cis-8-Chloro-1-[4-(pyridazin-3-yloxy)-cyclohexyl]-4H,6H-2,3,5,10b-tetraaza-benzo[e]azulene-5-carboxylic acid tert-butyl ester,
trans-8-Chloro-5-methyl-1-[4-(pyridazin-3-yloxy)-cyclohexyl]-5,6-dihydro-4H-2,3,5,10b-tetraaza-benzo[e]azulene,
cis-8-Chloro-1-[4-(pyridin-2-yloxy)-cyclohexyl]-4H,6H-2,3,5,10b-tetraaza-benzo[e]azulene-5-carboxylic acid tert-butyl ester,
cis-8-Chloro-1-[4-(pyridin-2-yloxy)-cyclohexyl]-5,6-dihydro-4H-2,3,5,10b-tetraaza-benzo[e]azulene,
cis-8-Chloro-5-methyl-1-[4-(pyridin-2-yloxy)-cyclohexyl]-5,6-dihydro-4H-2,3,5,10b-tetraaza-benzo[e]azulene,
trans-8-Chloro-1-[4-(3-fluoro-pyridin-2-yloxy)-cyclohexyl]-5,6-dihydro-4H-2,3,5,10b-tetraaza-benzo[e]azulene,
trans-8-Chloro-1-[4-(3-fluoro-pyridin-2-yloxy)-cyclohexyl]-5-methyl-5,6-dihydro-4H-2,3,5,10b-tetraaza-benzo[e]azulene,
trans-8-Chloro-1-[4-(5-fluoro-pyridin-2-yloxy)-cyclohexyl]-5,6-dihydro-4H-2,3,5,10b-tetraaza-benzo[e]azulene,
trans-8-Chloro-1-[4-(5-fluoro-pyridin-2-yloxy)-cyclohexyl]-5-methyl-5,6-dihydro-4H-2,3,5,10b-tetraaza-benzo[e]azulene,
trans-8-Chloro-1-[4-(6-methyl-pyridin-2-yloxy)-cyclohexyl]-5,6-dihydro-4H-2,3,5,10b-tetraaza-benzo[e]azulene,
trans-8-Chloro-5-(2,2-difluoro-ethyl)-1-[4-(6-methyl-pyridin-2-yloxy)-cyclohexyl]-5,6-dihydro-4H-2,3,5,10b-tetraaza-benzo[e]azulene,
trans-8-Chloro-5-(2-fluoro-ethyl)-1-[4-(5-fluoro-pyridin-2-yloxy)-cyclohexyl]-5,6-dihydro-4H-2,3,5,10b-tetraaza-benzo[e]azulene,
trans-8-Chloro-5-ethyl-1-[4-(3-fluoro-pyridin-2-yloxy)-cyclohexyl]-5,6-dihydro-4H-2,3,5,10b-tetraaza-benzo[e]azulene,
trans-8-Chloro-5-ethyl-1-[4-(5-fluoro-pyridin-2-yloxy)-cyclohexyl]-5,6-dihydro-4H-2,3,5,10b-tetraaza-benzo[e]azulene,
trans-8-Chloro-5-ethyl-1-[4-(6-methyl-pyridin-2-yloxy)-cyclohexyl]-5,6-dihydro-4H-2,3,5,10b-tetraaza-benzo[e]azulene, and
trans-8-Chloro-5-methyl-1-[4-(6-methyl-pyridin-2-yloxy)-cyclohexyl]-5,6-dihydro-4H-2,3,5,10b-tetraaza-benzo[e]azulene.

More preferred compounds are
trans-8-Chloro-1-(4-phenoxy-cyclohexyl)-4H,6H-2,3,5,10b-tetraaza-benzoazulene-5-carboxylic acid tert-butyl ester,
trans-8-Chloro-1-(4-phenoxy-cyclohexyl)-5,6-dihydro-4H-2,3,5,10b-tetraaza-benzo azulene hydrochloride,
trans-8-Chloro-5-methyl-1-(4-phenoxy-cyclohexyl)-5,6-dihydro-4H-2,3,5,10b-tetraaza-benzo[e]azulene,
trans-1-[8-Chloro-1-(4-phenoxy-cyclohexyl)-4H,6H-2,3,5,10b-tetraaza-benzoazulen-5-yl]-ethanone,
trans-8-Chloro-5-methanesulfonyl-1-(4-phenoxy-cyclohexyl)-5,6-dihydro-4H-2,3,5,10b-tetraaza-benzoazulene,
trans-2-[8-Chloro-1-(4-phenoxy-cyclohexyl)-4H,6H-2,3,5,10b-tetraaza-benzoazulen-5-yl]-ethanol,
trans-8-Chloro-5-isopropyl-1-(4-phenoxy-cyclohexyl)-5,6-dihydro-4H-2,3,5,10b-tetraaza-benzoazulene,
trans-8-Chloro-1-(4-phenoxy-cyclohexyl)-4H,6H-2,3,5,10b-tetraaza-benzoazulene-5-sulfonic acid dimethylamide,
trans-8-Chloro-1-(4-phenoxy-cyclohexyl)-5-pyridin-2-ylmethyl-5,6-dihydro-4H-2,3,5,10b-tetraaza-benzo azulene,
trans-1-[8-Chloro-1-(4-phenoxy-cyclohexyl)-4H,6H-2,3,5,10b-tetraaza-benzoazulen-5-yl]-2-dimethylamino-ethanone,
trans-8-Fluoro-1-(4-phenoxy-cyclohexyl)-4H,6H-2,3,5,10b-tetraaza-benzo[e]azulene-5-carboxylic acid tert-butyl ester,
trans-8-Fluoro-5-methyl-1-(4-phenoxy-cyclohexyl)-5,6-dihydro-4H-2,3,5,10b-tetraaza-benzoazulene,
cis-8-Chloro-1-(4-phenoxy-cyclohexyl)-4H,6H-2,3,5,10b-tetraaza-benzo azulene-5-carboxylic acid tert-butyl ester,
cis-8-Chloro-5-methyl-1-(4-phenoxy-cyclohexyl)-5,6-dihydro-4H-2,3,5,10b-tetraaza-benzoazulene,
trans-8-Chloro-1-[4-(4-fluoro-phenoxy)-cyclohexyl]-4H,6H-2,3,5,10b-tetraaza-benzo azulene-5-carboxylic acid tert-butyl ester,
trans-8-Chloro-1-[4-(4-fluoro-phenoxy)-cyclohexyl]-5,6-dihydro-4H-2,3,5,10b-tetraaza-benzo[e]azulene hydrochloride,
trans-8-Chloro-1-[4-(4-fluoro-phenoxy)-cyclohexyl]-5-methyl-5,6-dihydro-4H-2,3,5,10b-tetraaza-benzoazulene,
trans-8-Chloro-1-[4-(4-cyano-phenoxy)-cyclohexyl]-4H,6H-2,3,5,10b-tetraaza-benzo[e]azulene-5-carboxylic acid tert-butyl ester,
trans-4-[4-(8-Chloro-5-methyl-5,6-dihydro-4H-2,3,5,10b-tetraaza-benzo[e]azulen-1-yl)-cyclohexyloxy]-benzonitrile,
trans-8-Chloro-1-[4-(4-trifluoromethyl-phenoxy)-cyclohexyl]-4H,6H-2,3,5,10b-tetraaza-benzo[e]azulene-5-carboxylic acid tert-butyl ester,
trans-8-Chloro-1-[4-(3-chloro-phenoxy)-cyclohexyl]-4H,6H-2,3,5,10b-tetraaza-benzoazulene-5-carboxylic acid tert-butyl ester,
trans-8-Chloro-1-[4-(3-chloro-phenoxy)-cyclohexyl]-5-methyl-5,6-dihydro-4H-2,3,5,10b-tetraaza-benzoazulene,
trans-8-Chloro-1-[4-(3-methoxy-phenoxy)-cyclohexyl]-4H,6H-2,3,5,10b-tetraaza-benzoazulene-5-carboxylic acid tert-butyl ester,
trans-8-Chloro-1-[4-(3-methoxy-phenoxy)-cyclohexyl]-5,6-dihydro-4H-2,3,5,10b-tetraaza-benzo[e]azulene hydrochloride,
trans-8-Chloro-1-[4-(3-methoxy-phenoxy)-cyclohexyl]-5-methyl-5,6-dihydro-4H-2,3,5,10b-tetraaza-benzoazulene,
trans-3-[4-(8-Chloro-5-methyl-5,6-dihydro-4H-2,3,5,10b-tetraaza-benzoazulen-1-yl)-cyclohexyloxy]-benzonitrile,
trans-8-Chloro-1-(4-m-tolyloxy-cyclohexyl)-4H,6H-2,3,5,10b-tetraaza-benzo[e]azulene-5-carboxylic acid tert-butyl ester, trans-8-Chloro-1-(4-m-tolyloxy-cyclohexyl)-5,6-dihydro-4H-2,3,5,10b-tetraaza-benzo[e]azulene hydrochloride,
trans-8-Chloro-5-methyl-1-(4-m-tolyloxy-cyclohexyl)-5,6-dihydro-4H-2,3,5,10b-tetraaza-benzo[e]azulene,
trans-1-[4-(3-tert-Butyl-phenoxy)-cyclohexyl]-8-chloro-4H,6H-2,3,5,10b-tetraaza-benzo[e]azulene-5-carboxylic acid tert-butyl ester,
trans-8-Chloro-1-[4-(2-fluoro-phenoxy)-cyclohexyl]-4H,6H-2,3,5,10b-tetraaza-benzo[e]azulene-5-carboxylic acid tert-butyl ester,
trans-8-Chloro-1-[4-(2-fluoro-phenoxy)-cyclohexyl]-5,6-dihydro-4H-2,3,5,10b-tetraaza-benzo[e]azulene hydrochloride,
trans-8-Chloro-1-[4-(2-fluoro-phenoxy)-cyclohexyl]-5-methyl-5,6-dihydro-4H-2,3,5,10b-tetraaza-benzo[e]azulene,
trans-8-Chloro-1-[4-(2-cyano-phenoxy)-cyclohexyl]-4H,6H-2,3,5,10b-tetraaza-benzoazulene-5-carboxylic acid tert-butyl ester,
trans-2-[4-(8-Chloro-5,6-dihydro-4H-2,3,5,10b-tetraaza-benzo[e]azulen-1-yl)-cyclohexyloxy]-benzonitrile hydrochloride,
trans-2-[4-(8-Chloro-5-methyl-5,6-dihydro-4H-2,3,5,10b-tetraaza-benzoazulen-1-yl)-cyclohexyloxy]-benzonitrile,
trans-8-Chloro-1-(4-o-tolyloxy-cyclohexyl)-4H,6H-2,3,5,10b-tetraaza-benzoazulene-5-carboxylic acid tert-butyl ester,
trans-8-Chloro-5-methyl-1-(4-o-tolyloxy-cyclohexyl)-5,6-dihydro-4H-2,3,5,10b-tetraaza-benzoazulene,
trans-8-Chloro-1-[4-(3,5-difluoro-phenoxy)-cyclohexyl]-4H,6H-2,3,5,10b-tetraaza-benzoazulene-5-carboxylic acid tert-butyl ester,
trans-8-Chloro-1-[4-(3,5-difluoro-phenoxy)-cyclohexyl]-5-methyl-5,6-dihydro-4H-2,3,5,10b-tetraaza-benzoazulene,
trans-8-Chloro-1-[4-(naphthalen-2-yloxy)-cyclohexyl]-4H,6H-2,3,5,10b-tetraaza-benzoazulene-5-carboxylic acid tert-butyl ester,
trans-8-Chloro-5-methyl-1-[4-(naphthalen-2-yloxy)-cyclohexyl]-5,6-dihydro-4H-2,3,5,10b-tetraaza-benzoazulene,
trans-8-Chloro-1-[4-(pyridin-3-yloxy)-cyclohexyl]-4H,6H-2,3,5,10b-tetraaza-benzoazulene-5-carboxylic acid tert-butyl ester,
trans-8-Chloro-5-methyl-1-[4-(pyridin-3-yloxy)-cyclohexyl]-5,6-dihydro-4H-2,3,5,10b-tetraaza-benzoazulene,
trans-8-Chloro-1-[4-(5-chloro-pyridin-3-yloxy)-cyclohexyl]-4H,6H-2,3,5,10b-tetraaza-benzoazulene-5-carboxylic acid tert-butyl ester,
trans-8-Chloro-1-[4-(5-chloro-pyridin-3-yloxy)-cyclohexyl]-5-methyl-5,6-dihydro-4H-2,3,5,10b-tetraaza-benzo azulene,
trans-8-Chloro-1-[4-(pyridin-2-yloxy)-cyclohexyl]-4H,6H-2,3,5,10b-tetraaza-benzoazulene-5-carboxylic acid tert-butyl ester,
trans-8-Chloro-1-[4-(pyridin-2-yloxy)-cyclohexyl]-5,6-dihydro-4H-2,3,5,10b-tetraaza-benzoazulene hydrochloride,
trans-8-Chloro-5-methyl-1-[4-(pyridin-2-yloxy)-cyclohexyl]-5,6-dihydro-4H-2,3,5,10b-tetraaza-benzoazulene,
trans-8-Chloro-1-[4-(6-chloro-pyridin-2-yloxy)-cyclohexyl]-4H,6H-2,3,5,10b-tetraaza-benzo[e]azulene-5-carboxylic acid tert-butyl ester,
trans-8-Chloro-1-[4-(6-chloro-pyridin-2-yloxy)-cyclohexyl]-5-methyl-5,6-dihydro-4H-2,3,5,10b-tetraaza-benzo[e]azulene,
trans-8-Chloro-1-[4-(5-chloro-pyridin-2-yloxy)-cyclohexyl]-5,6-dihydro-4H-2,3,5,10b-tetraaza-benzo[e]azulene hydrochloride,
trans-8-Chloro-1-[4-(5-chloro-pyridin-2-yloxy)-cyclohexyl]-5-methyl-5,6-dihydro-4H-2,3,5,10b-tetraaza-benzo[e]azulene,
trans-8-Chloro-1-[4-(pyrimidin-2-yloxy)-cyclohexyl]-4H,6H-2,3,5,10b-tetraaza-benzo[e]azulene-5-carboxylic acid tert-butyl ester,
cis-8-Chloro-1-[4-(pyrimidin-2-yloxy)-cyclohexyl]-4H,6H-2,3,5,10b-tetraaza-benzo[e]azulene-5-carboxylic acid tert-butyl ester,
trans-8-Chloro-5-methyl-1-[4-(pyrimidin-2-yloxy)-cyclohexyl]-5,6-dihydro-4H-2,3,5,10b-tetraaza-benzo[e]azulene,
trans-8-Chloro-1-[4-(pyrazin-2-yloxy)-cyclohexyl]-4H,6H-2,3,5,10b-tetraaza-benzo[e]azulene-5-carboxylic acid tert-butyl ester,
trans-8-Chloro-5-methyl-1-[4-(pyrazin-2-yloxy)-cyclohexyl]-5,6-dihydro-4H-2,3,5,10b-tetraaza-benzo[e]azulene,
trans-8-Chloro-1-[4-(pyrimidin-4-yloxy)-cyclohexyl]-4H,6H-2,3,5,10b-tetraaza-benzo[e]azulene-5-carboxylic acid tert-butyl ester,
trans-8-Chloro-5-methyl-1-[4-(pyrimidin-4-yloxy)-cyclohexyl]-5,6-dihydro-4H-2,3,5,10b-tetraaza-benzo[e]azulene,
trans-8-Chloro-1-[4-(pyridazin-3-yloxy)-cyclohexyl]-4H,6H-2,3,5,10b-tetraaza-benzo[e]azulene-5-carboxylic acid tert-butyl ester,
cis-8-Chloro-1-[4-(pyridazin-3-yloxy)-cyclohexyl]-4H,6H-2,3,5,10b-tetraaza-benzo[e]azulene-5-carboxylic acid tert-butyl ester, and
trans-8-Chloro-5-methyl-1-[4-(pyridazin-3-yloxy)-cyclohexyl]-5,6-dihydro-4H-2,3,5,10b-tetraaza-benzo[e]azulene.

Particularly preferred are trans-8-Chloro-5-methyl-1-(4-phenoxy-cyclohexyl)-5,6-dihydro-4H-2,3,5,10b-tetraaza-benzo[e]azulene and trans-8-Chloro-5-methyl-1-[4-(pyridin-2-yloxy)-cyclohexyl]-5,6-dihydro-4H-2,3,5,10b-tetraaza-benzoazulene.

Most preferred is trans-8-Chloro-5-methyl-1-[4-(pyridin-2-yloxy)-cyclohexyl]-5,6-dihydro-4H-2,3,5,10b-tetraaza-benzo azulene.

A certain embodiment of the invention is a compound as described in any of the embodiments obtainable by a process according as described herewithin.

A certain embodiment of the invention is a compound as described in any of the embodiments, whenever obtained by a process according as described herewithin.

A certain embodiment of the invention is a compound as described in any of the embodiments for the use as therapeutically active substance.

A certain embodiment of the invention is a compound as described in any of the embodiments for a use in the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

A certain embodiment of the invention is a pharmaceutical composition comprising a compound as described in any of the embodiments.

A certain embodiment of the invention is a pharmaceutical composition comprising a compound as described in any of the embodiments, wherein it is useful for the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

A certain embodiment of the invention is a method for the therapeutic and/or prophylactic treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior, which method comprises administering a compound as defined in any if the embodiments to a human being or animal.

In a certain embodiment, the compounds of formula (I) of the invention can be manufactured according to a process comprising the step of reacting a compound of formula (II)

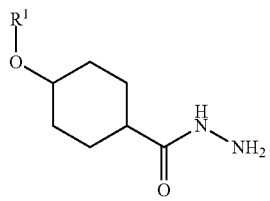

II with a compound of formula (III)

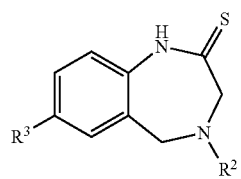

III to obtain a compound of formula (I) wherein $R^1$, $R^2$ and $R^3$ are as defined hereinabove for formula (I).

The processes are described in more detail with the following general schemes and procedures A to G.

Scheme 1: General Scheme A

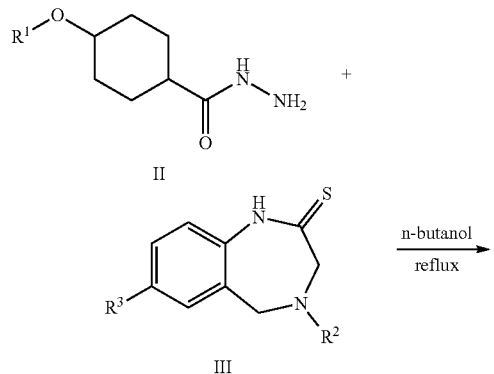

Compounds of formula (I) can be prepared by thermal condensation of a hydrazide derivative of formula (II) and a thiolactam derivative of formula (III). The synthesis of compounds of formula (II) is outlined in general schemes D-G hereinafter. Compounds of formula (III) can be prepared following the general scheme C as described hereinafter. General scheme A is hereinafter further illustrated with general procedure V.

Scheme 2: General Scheme B

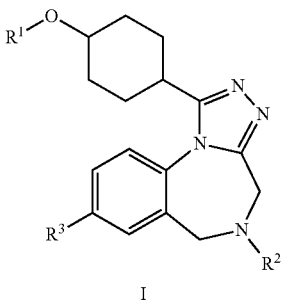

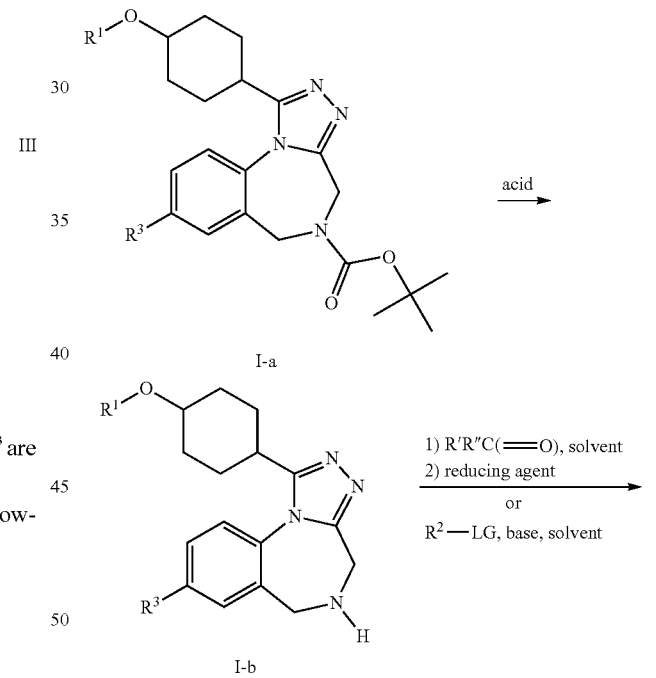

Compounds of formula (I) with $R^2$ different from H can be prepared from compounds of formula (I-b) (compounds of formula (I) wherein $R^2$ is H) according to methods known in the art, e.g. by treating a compound of formula (I-b) with an inorganic base such as a carbonate salt or an organic base such as a tertiary amine and an electrophilic reactant $R^2$-LG (wherein LG is a leaving group, e.g. halogen or sulfonyl) which is either commercially available or easily prepared according to methods and starting materials well known in the art. Alternatively, compounds of formula (I) can be obtained via reductive alkylation by consecutively treating a compound of formula (I-b) with a ketone or aldehyde and a suitable reducing agent, e.g. a borohydride derivative such as sodium borohydride, sodium cyanoborohydride or sodium triacetoxyborohydride. Compounds of formula (I-b) can be obtained by cleavage of the substituent $R^2$ of compound of formula I using methods known in the art. Compounds of formula (I-b) are conveniently obtained as the salt or the free base after basic aqueous work-up by treatment of compounds of formula (I-a) (compounds of formula (I) in which $R^2$ is tert-butoxycarbonyl) with an acid in a suitable solvent, e.g. methanesulfonic acid in dichloromethane or tetrahydrofuran or hydrochloric acid in methanol. General scheme C is hereinafter further illustrated with general procedures VI and VII.

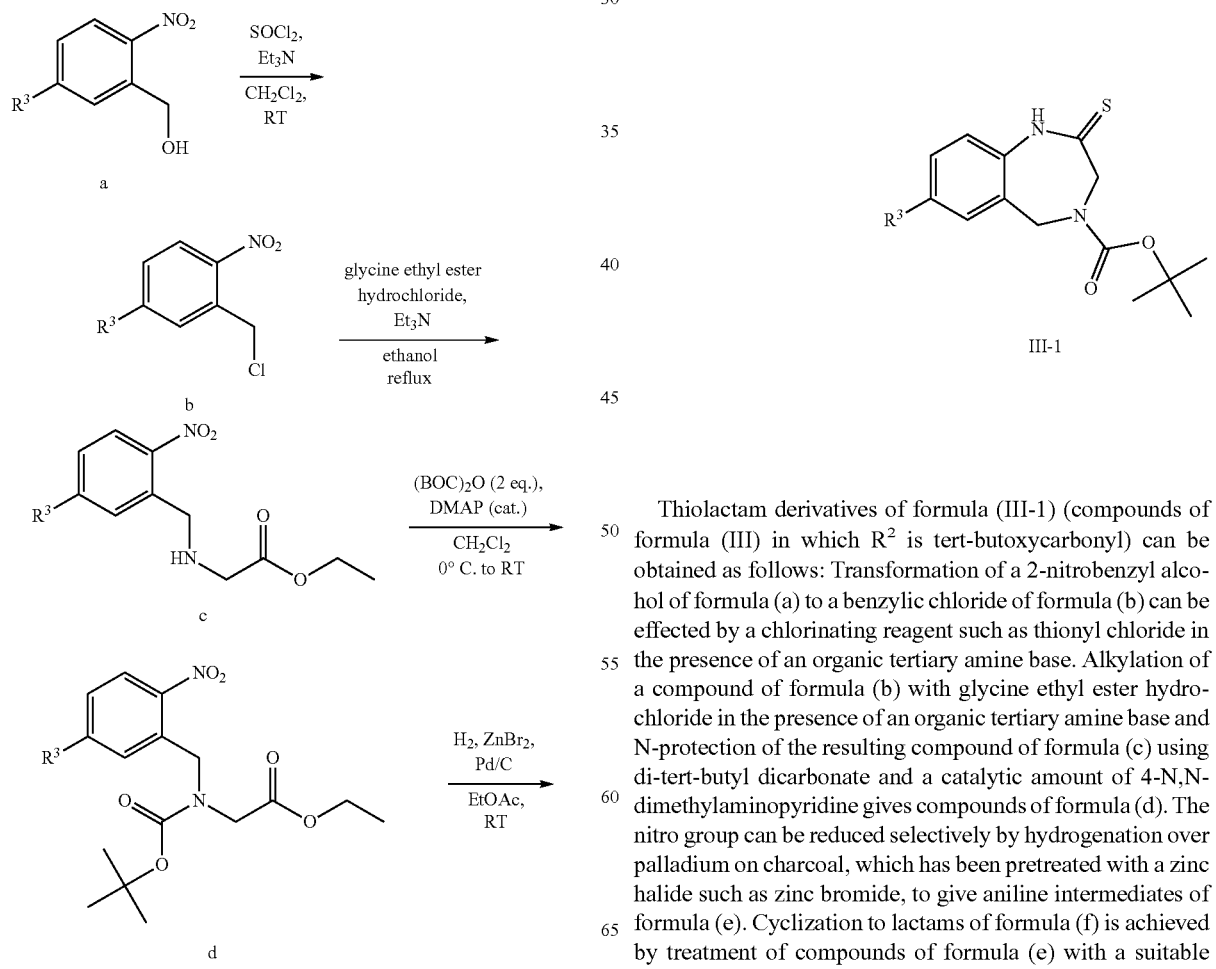

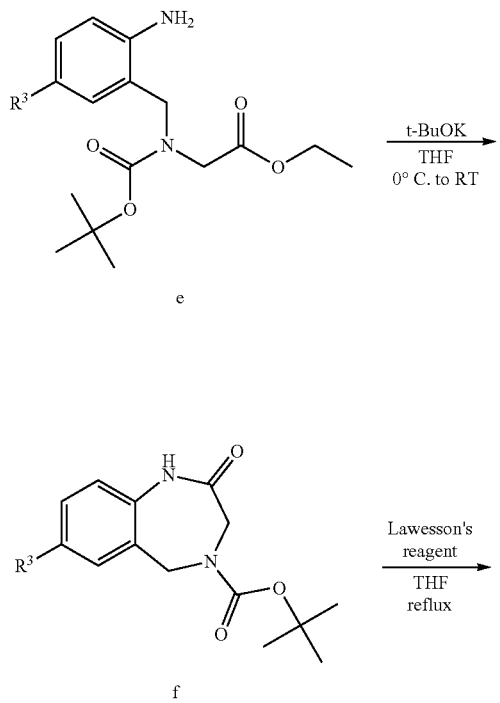

Thiolactam derivatives of formula (III-1) (compounds of formula (III) in which $R^2$ is tert-butoxycarbonyl) can be obtained as follows: Transformation of a 2-nitrobenzyl alcohol of formula (a) to a benzylic chloride of formula (b) can be effected by a chlorinating reagent such as thionyl chloride in the presence of an organic tertiary amine base. Alkylation of a compound of formula (b) with glycine ethyl ester hydrochloride in the presence of an organic tertiary amine base and N-protection of the resulting compound of formula (c) using di-tert-butyl dicarbonate and a catalytic amount of 4-N,N-dimethylaminopyridine gives compounds of formula (d). The nitro group can be reduced selectively by hydrogenation over palladium on charcoal, which has been pretreated with a zinc halide such as zinc bromide, to give aniline intermediates of formula (e). Cyclization to lactams of formula (f) is achieved by treatment of compounds of formula (e) with a suitable base, e.g. potassium tert-butoxide, in tetrahydrofuran. A thiolactam derivative of formula (III-1) is obtained by treatment of a compound of formula (f) with Lawesson's reagent (2,4-bis-(4-methoxyphenyl)-1,3,2,4-dithiadiphosphetane-2,4-disulfide) or phosphorous pentasulfide at elevated temperature.

Scheme 4: General Scheme D

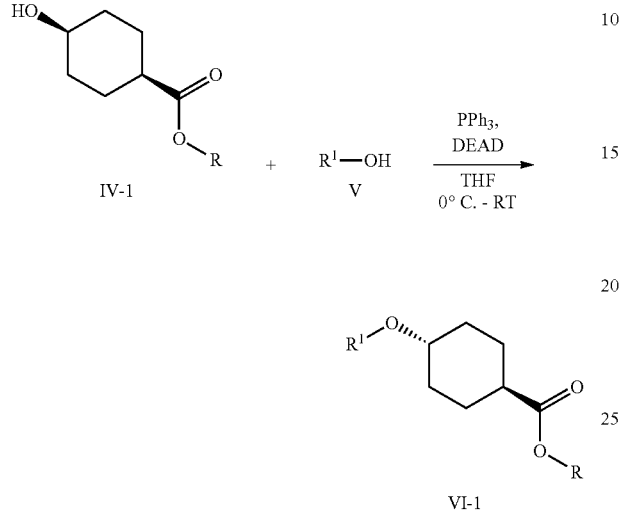

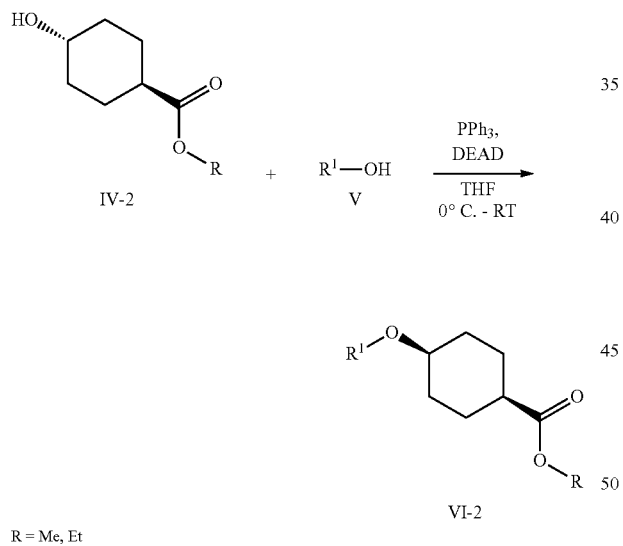

R = Me, Et

Etherification of a 4-hydroxy-cyclohexanecarboxylic acid ester of formula (IV) with a phenol derivative of formula (V) under Mitsunobu conditions leads to a 4-aryloxy-cyclohexanecarboxylic acid ester of formula (VI) under inversion of configuration. Thus trans-4-aryloxy-cyclohexanecarboxylic acid esters of formula (VI-1) are obtained from a cis-4-hydroxy-cyclohexanecarboxylic acid ester of formula (IV-1), while cis-4-aryloxy-cyclohexanecarboxylic acid esters of formula (VI-2) are obtained from a trans-4-hydroxy-cyclohexanecarboxylic acid ester of formula (IV-2).

Scheme 5: General Scheme E

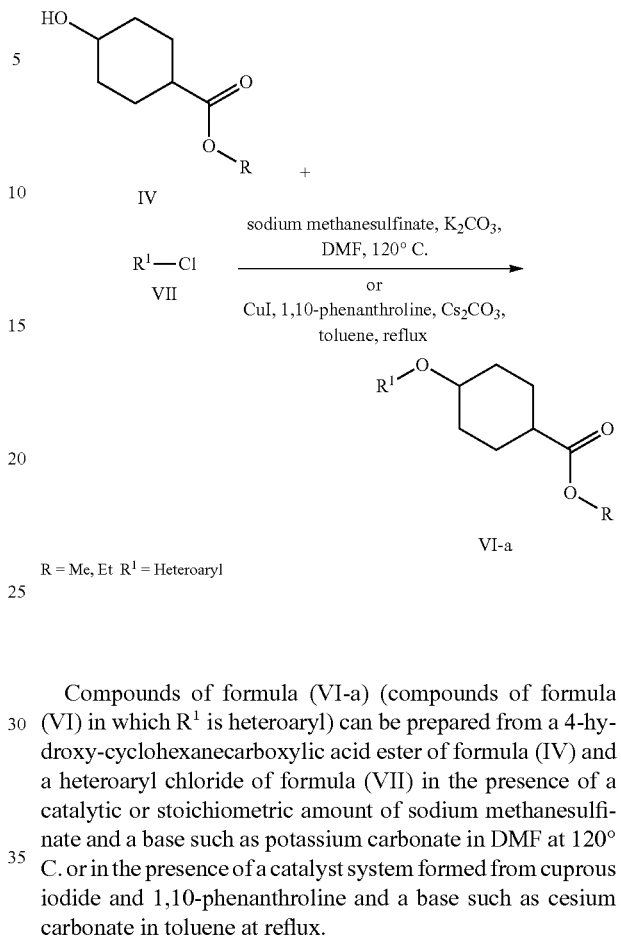

R = Me, Et  $R^1$ = Heteroaryl

Compounds of formula (VI-a) (compounds of formula (VI) in which $R^1$ is heteroaryl) can be prepared from a 4-hydroxy-cyclohexanecarboxylic acid ester of formula (IV) and a heteroaryl chloride of formula (VII) in the presence of a catalytic or stoichiometric amount of sodium methanesulfinate and a base such as potassium carbonate in DMF at 120° C. or in the presence of a catalyst system formed from cuprous iodide and 1,10-phenanthroline and a base such as cesium carbonate in toluene at reflux.

Scheme 6: General Scheme F

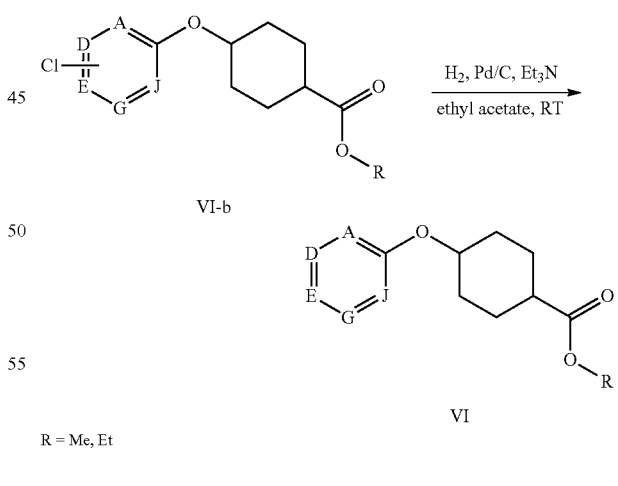

R = Me, Et

Compounds of formula (VI-b) (compounds of formula (VI) in which $R^1$ is substituted with Cl) can be dechlorinated under hydrogenolytic conditions in the presence of palladium on charcoal and triethylamine in ethyl acetate at room temperature.

Scheme 7: General Scheme G

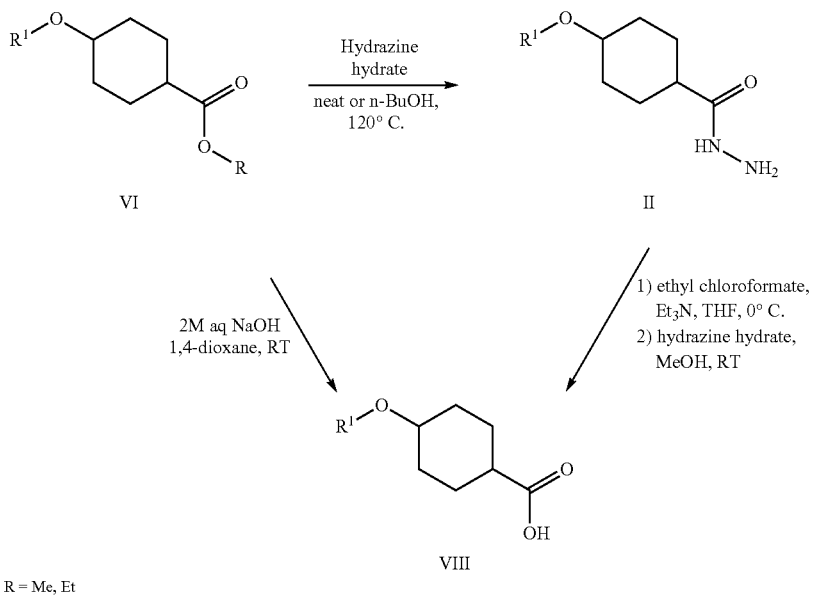

R = Me, Et

A 4-aryloxy-cyclohexanecarboxylic acid ester of formula (VI) can be converted to a hydrazide derivative of formula (II) by heating with hydrazine hydrate. Alternatively, an ester derivative of formula (VI) can be hydrolyzed to a carboxylic acid derivative of formula (VIII) using a biphasic mixture of aqueous sodium or potassium hydroxide solution and an etheral solvent such as dioxan. A hydrazide derivative of formula (II) can be obtained by activating an acid intermediate of formula (VIII), e.g. with ethyl chloroformate, thionyl chloride, oxalylchloride or a peptide coupling reagent, and subsequent coupling with hydrazine.

The corresponding pharmaceutically acceptable salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. M(OH)$_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

Insofar as their preparation is not described in the examples, the compounds of formula I as well as all intermediate products can be prepared according to analogous methods or according to the methods set forth herewithin. Starting materials are commercially available, known in the art or can be prepared by methods known in the art or in analogy thereto.

It will be appreciated that the compounds of general formula I in this invention can be derivatized at functional groups to provide derivatives which are capable of conversion back to the parent compound in vivo.

Pharmacological Tests

The compounds of the present invention exhibit V1a activity. They are selective inhibitors of the V1a receptor and are therefore likely to have a low potential to cause unwanted off-target related side-effects. The Via activity can be detected as described below.

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g of cells are resuspended in 30 ml freshly prepared ice cold Lysis buffer (50 mM HEPES, 1 mM EDTA, 10 mM magnesium dichloride adjusted to pH=7.4+complete cocktail of protease inhibitor (Roche Diagnostics)). Homogenized with Polytron for 1 min and sonicated on ice for 2×2 minutes at 80% intensity (Vibracell sonicator). The preparation is centrifuged 20 min at 500 g at 4° C., the pellet is discarded and the supernatant centrifuged 1 hour at 43'000 g at 4° C. (19'000 rpm). The pellet is resuspended in 12.5 ml Lysis buffer+12.5 ml Sucrose 20% and homogenized using a Polytron for 1-2 min. The protein concentration is determined by the Bradford method and aliquots are stored at −80° C. until use. For binding studies 60 mg Yttrium silicate SPA beads (Amersham) are mixed with an aliquot of membrane in binding buffer (50 mM Tris, 120 mM sodium chloride, 5 mM potassium chloride, 2 mM Calcium dichloride, 10 mM magnesium dichloride) for 15 minutes with mixing. 50 µl of bead/membrane mixture is then added to each well of a 96 well plate, followed by 50 µl of 4 nM 3H-Vasopressin (American Radiolabeled Chemicals). For total binding measurement 100 µl of binding buffer are added to the respective wells, for non-specific binding 100 µl of 8.4 mM cold vasopressin and for compound testing 100 µl of a serial dilution of each compound in 2% dimethyl sulfoxide. The plate is incubated 1 h at room temperature, centrifuged 1 mM at 1000 g and counted on a Packard Top-Count. Non-specific binding counts are subtracted from each well and data is normalized to the maximum specific binding set at 100%. To calculate an IC 50 the curve is fitted using a non-linear regression model (XLfit) and the Ki is calculated using the Cheng-Prussoff equation.

The following representative data show the antagonistic activity against human V1a receptor of compounds according to present invention.

TABLE 3

| Ex# | pKi (hV1a) |
|---|---|
| 1 | 8.49 |
| 2 | 8.36 |
| 3 | 8.80 |
| 4 | 8.85 |
| 5 | 8.77 |
| 6 | 8.80 |
| 7 | 8.77 |
| 8 | 8.70 |
| 9 | 8.74 |
| 10 | 8.68 |
| 11 | 8.26 |
| 13 | 8.27 |
| 14 | 8.03 |
| 16 | 8.54 |
| 17 | 8.43 |
| 18 | 8.02 |
| 19 | 8.51 |
| 20 | 8.11 |
| 22 | 8.05 |
| 23 | 8.04 |
| 26 | 8.38 |
| 28 | 8.51 |
| 29 | 8.33 |
| 30 | 8.48 |
| 31 | 8.68 |
| 34 | 8.57 |
| 35 | 8.31 |
| 36 | 8.12 |
| 37 | 8.77 |
| 38 | 7.74 |
| 43 | 8.21 |
| 44 | 8.47 |
| 45 | 8.44 |
| 46 | 8.54 |
| 47 | 8.92 |
| 48 | 9.10 |
| 49 | 8.15 |
| 51 | 8.43 |
| 52 | 8.46 |
| 54 | 8.41 |
| 55 | 8.03 |
| 57 | 8.24 |
| 61 | 8.82 |
| 63 | 8.34 |
| 64 | 8.02 |
| 66 | 8.04 |
| 67 | 8.48 |
| 68 | 8.21 |
| 69 | 8.96 |
| 70 | 8.04 |
| 72 | 8.62 |
| 74 | 7.95 |
| 75 | 8.55 |
| 79 | 8.59 |
| 80 | 7.90 |
| 82 | 8.26 |
| 83 | 8.39 |
| 85 | 8.12 |
| 86 | 8.46 |
| 89 | 7.91 |
| 92 | 8.62 |
| 93 | 8.10 |
| 95 | 8.04 |
| 98 | 8.52 |
| 101 | 8.04 |
| 105 | 8.24 |
| 110 | 7.29 |
| 111 | 8.48 |

Pharmaceutical Compositions

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatine capsules. Suitable excipients for soft gelatine capsules are e.g. vegetable oils, waxes, fats, semisolid and liquid polyols etc.

Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following examples illustrate the present invention without limiting it. All temperatures are given in degrees Celsius.

Examples of compositions according to the invention are, but are not limited to:

Example A

Tablets of the Following Composition are Manufactured in the Usual Manner:

TABLE 4 possible tablet composition

| ingredient | mg/tablet | | | |
|---|---|---|---|---|
| | 5 | 25 | 100 | 500 |
| 1. Compound of formula I | 5 | 25 | 100 | 500 |
| 2. Lactose | 45 | 105 | 30 | 150 |
| 3. Corn Starch | 15 | 6 | 6 | 60 |
| 4. Microcrystalline Cellulose | 34 | 30 | 30 | 450 |
| 5. Magnesium Stearate | 1 | 1 | 1 | 1 |
| Total | 100 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the Following Composition are Manufactured:

TABLE 5 possible capsule ingredient composition

| ingredient | mg/capsule | | | | |
|---|---|---|---|---|---|
| | 5 | 10 | 25 | 100 | 500 |
| 1. Compound of formula I | 5 | 10 | 25 | 100 | 500 |
| 2. Lactose | 159 | 155 | 123 | 148 | — |
| 3. Corn Starch | 25 | 30 | 35 | 40 | 70 |
| 4. Talc | 10 | 5 | 15 | 10 | 25 |
| 5. Magnesium Stearate | 1 | — | 2 | 2 | 5 |
| Total | 200 | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer, the talc (and magnesium stearate) is added thereto and mixed thoroughly. The mixture is filled by machine into suitable capsules, e.g. hard gelatine capsules.

Example B-2

Soft Gelatine Capsules of the Following Composition are Manufactured:

TABLE 6 possible soft gelatine capsule ingredient composition

| ingredient | mg/capsule |
|---|---|
| Compound of formula I | 5 |
| Yellow wax | 8 |
| Hydrogenated Soya bean oil | 8 |

TABLE 6-continued possible soft gelatine capsule ingredient composition

| ingredient | mg/capsule |
|---|---|
| Partially hydrogenated plant oils | 34 |
| Soya bean oil | 110 |
| Total | 165 |

TABLE 7 possible soft gelatine capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the Following Composition are Manufactured:

TABLE 8 possible suppository composition

| ingredient | mg/supp. |
|---|---|
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool, the suppositories are then removed from the moulds and packed individually in wax paper or metal foil.

Example D

Injection Solutions of the Following Composition are Manufactured:

TABLE 9 possible injection solution composition

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the Following Composition are Manufactured:

TABLE 10

| possible sachet composition | |
| --- | --- |
| ingredient | mg/sachet |
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesiumstearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesiumstearate and the flavoring additives and filled into sachets.

Examples

The following examples 1-97 are provided for illustration of the invention. They should not be considered as limiting the scope of the invention, but merely as being representative thereof.

4-Hydroxy-cyclohexanecarboxylic Acid Ester Intermediates of Formula (IV)

4-Hydroxy-cyclohexanecarboxylic acid ester 1 cis-4-Hydroxy-cyclohexanecarboxylic acid methyl ester

A solution of cis-4-hydroxy-cyclohexanecarboxylic acid (10.0 g, 69.4 mmol) and a catalytic amount of concentrated sulfuric acid in methanol (700 ml) was heated at reflux over night. After cooling to room temperature the reaction mixture was neutralized by the addition of solid sodium carbonate. The mixture was stirred for 30 min, filtered and concentrated in vacuo. The residue was triturated in ethyl acetate (150 ml). The solids were removed by filtration. The filtrate was concentrated in vacuo to give the crude product (10.3 g, 94%) as colorless oil, which was used in the following steps without further purification. MS m/e: 159 (M+H$^+$).

4-Hydroxy-cyclohexanecarboxylic acid ester 2 trans-4-Hydroxy-cyclohexanecarboxylic acid methyl ester

The title compound was obtained as a colorless oil in 63% yield according to the procedure described for the preparation of cis-4-hydroxy-cyclohexanecarboxylic acid methyl ester using trans-4-hydroxy-cyclohexanecarboxylic acid instead of cis-4-hydroxy-cyclohexanecarboxylic acid. MS (EI) m/e: 159 (M$^+$, 1%), 140 (M$^+$-H$_2$0, 45%)

4-Aryloxy-cyclohexanecarboxylic Acid Ester Intermediates of Formula (VI)

General Procedure I: Etherification Under Mitsunobu Conditions

To a solution of triphenylphosphine (1.2 eq) in dry tetrahydrofuran (0.1 M) is added diethyl azodicarboxylate (1.2 eq) at 0° C. After 20 min a phenol derivative of formula (V) (1.2 eq) and a solution of a 4-hydroxy-cyclohexanecarboxylic acid ester of formula (IV) in tetrahydrofuran (1-3 M) are added consecutively at 5° C. After completed addition the cooling bath is removed and the reaction mixture is allowed to warm to room temperature and stirred for 3-18 h. The solvent is evaporated and the residue is dissolved in ethyl acetate. The ethyl acetate solution is washed with one to two portions of 1 M aqueous sodium hydroxide solution. The aqueous layer is extracted with one to two portions of ethyl acetate. The combined organic layers are dried over anhydrous sodium sulfate and concentrated in vacuo. Purification by flash-chromatography gives a 4-aryloxy-cyclohexanecarboxylic acid ester of formula (VI).

General Procedure II: Sodium Methanesulfinate Mediated Arylation

To a solution of a 4-hydroxy-cyclohexanecarboxylic acid ester of formula (IV) (1 eq) and a heteroaryl chloride derivative (1 eq) in dry N,N-dimethylformamide (1 M) are added consecutively sodium methanesulfinate (85%, 0.25-1 eq) and potassium carbonate (1.5 eq). After completed addition the reaction mixture is stirred at 120° C. for 3-18 h. After cooling to room temperature the reaction mixture is partitioned between tert-butyl methyl ether and water. The layers are separated and the aqueous layer is extracted with one to two portions of tert-butyl methyl ether. The combined organic layers are washed with one to two portions of water, dried over anhydrous sodium sulfate and concentrated in vacuo. Purification by flash-chromatography gives a 4-heteroaryloxy-cyclohexanecarboxylic acid ester of formula (VI-a).

General Procedure III: Copper Catalyzed Arylation

To a mixture of cuprous iodide (0.1 eq), 1,10-phenanthroline (0.2 eq) and a heteroaryl chloride derivative (1 eq) in toluene (2 M) are added a 4-hydroxy-cyclohexanecarboxylic acid ester of formula (IV) (1 eq) and cesium carbonate (2 eq). The reaction mixture is heated at reflux for 20 h. After cooling to room temperature the reaction mixture is partitioned between ethyl acetate and water. The layers are separated and the aqueous layer is extracted with one to two portions of ethyl acetate. The combined organic layers are washed with one to two portions of 0.5 aqueous hydrogen chloride solution, dried over anhydrous sodium sulfate and concentrated in vacuo. Purification by flash-chromatography gives a 4-heteroaryloxy-cyclohexanecarboxylic acid ester of formula (VI-a).

4-Aryloxy-cyclohexanecarboxylic acid ester 1 trans-4-Phenoxy-cyclohexanecarboxylic acid methyl ester

The title compound was obtained as colorless oil in 23% yield according to general procedure I.
Phenol: Phenol 4-Hydroxy-cyclohexanecarboxylic acid ester: cis-4-Hydroxy-cyclohexanecarboxylic acid methyl ester
MS m/e: 234 (M$^+$)

4-Aryloxy-cyclohexanecarboxylic acid ester 2 cis-4-Phenoxy-cyclohexanecarboxylic acid methyl ester

The title compound was obtained as colorless oil in 54% yield according to general procedure I.
Phenol: Phenol
4-Hydroxy-cyclohexanecarboxylic acid ester: trans-4-Hydroxy-cyclohexanecarboxylic acid methyl ester
MS m/e: 234 (M$^+$)

4-Aryloxy-cyclohexanecarboxylic acid ester 3 trans-4-(4-Fluoro-phenoxy)-cyclohexanecarboxylic acid methyl ester

The title compound was obtained as pink oil in 29% yield according to general procedure I.
Phenol: 4-Fluorophenol
4-Hydroxy-cyclohexanecarboxylic acid ester: cis-4-Hydroxy-cyclohexanecarboxylic acid methyl ester
MS m/e: 252 (M$^+$)

4-Aryloxy-cyclohexanecarboxylic acid ester 4 trans-4-(4-Cyano-phenoxy)-cyclohexanecarboxylic acid methyl ester

The title compound was obtained according to general procedure I.
Phenol: 4-Hydroxybenzonitrile
4-Hydroxy-cyclohexanecarboxylic acid ester: cis-4-Hydroxy-cyclohexanecarboxylic acid methyl ester
MS m/e: 260 (M+H$^+$)

4-Aryloxy-cyclohexanecarboxylic acid ester 5 trans-4-(4-Trifluoromethyl-phenoxy)-cyclohexanecarboxylic acid methyl ester

The title compound was obtained according to general procedure I.
Phenol: 4-Trifluoromethyl-phenol
4-Hydroxy-cyclohexanecarboxylic acid ester: cis-4-Hydroxy-cyclohexanecarboxylic acid methyl ester
MS m/e: 303 (M+H$^+$)

4-Aryloxy-cyclohexanecarboxylic acid ester 6 trans-4-(3-Chloro-phenoxy)-cyclohexanecarboxylic acid methyl ester

The title compound was obtained as colorless oil in 38% yield according to general procedure I
Phenol: 3-Chlorophenol
4-Hydroxy-cyclohexanecarboxylic acid ester: cis-4-Hydroxy-cyclohexanecarboxylic acid methyl ester
MS m/e: 268 (M$^+$)

4-Aryloxy-cyclohexanecarboxylic acid ester 7 trans-4-(3-Methoxy-phenoxy)-cyclohexanecarboxylic acid methyl ester

The title compound was obtained as pink oil in 33% yield according to general procedure I.
Phenol: 3-Methoxyphenol
4-Hydroxy-cyclohexanecarboxylic acid ester: cis-4-Hydroxy-cyclohexanecarboxylic acid methyl ester
MS m/e: 265 (M+H$^+$)

4-Aryloxy-cyclohexanecarboxylic acid ester 8 trans-4-(3-Cyano-phenoxy)-cyclohexanecarboxylic acid methyl ester

The title compound was obtained as white solid in 29% yield according to general procedure I.
Phenol: 3-Hydroxypyridine
4-Hydroxy-cyclohexanecarboxylic acid ester: cis-4-Hydroxy-cyclohexanecarboxylic acid methyl ester
MS m/e: 259 (M+H$^+$)

4-Aryloxy-cyclohexanecarboxylic acid ester 9 trans-4-m-Tolyloxy-cyclohexanecarboxylic acid methyl ester

The title compound was obtained according to general procedure I.
Phenol: 3-Methylphenol
4-Hydroxy-cyclohexanecarboxylic acid ester: cis-4-Hydroxy-cyclohexanecarboxylic acid methyl ester
MS m/e: 248 (M$^+$)

4-Aryloxy-cyclohexanecarboxylic acid ester 10 trans-4-(3-tert-Butyl-phenoxy)-cyclohexanecarboxylic acid methyl ester

The title compound was obtained according to general procedure I.
Phenol: 3-tert-Butylphenol
4-Hydroxy-cyclohexanecarboxylic acid ester: cis-4-Hydroxy-cyclohexanecarboxylic acid methyl ester
MS m/e: 291 (M+H$^+$)

4-Aryloxy-cyclohexanecarboxylic acid ester 11 trans-4-(3-Trifluoromethyl-phenoxy)-cyclohexanecarboxylic acid methyl ester

The title compound was obtained according to general procedure I.
Phenol: 3-Trifluoromethylphenol
4-Hydroxy-cyclohexanecarboxylic acid ester: cis-4-Hydroxy-cyclohexanecarboxylic acid methyl ester
MS m/e: 302 (M+H$^+$)

4-Aryloxy-cyclohexanecarboxylic acid ester 12 trans-4-(2-Fluoro-phenoxy)-cyclohexanecarboxylic acid methyl ester

The title compound can be obtained according to general procedure I.

Phenol: 4-Fluorophenol
4-Hydroxy-cyclohexanecarboxylic acid ester: cis-4-Hydroxy-cyclohexanecarboxylic acid methyl ester 4-Aryloxy-cyclohexanecarboxylic acid ester 13 trans-4-(2-Cyano-phenoxy)-cyclohexanecarboxylic acid methyl ester

The title compound was obtained as pink solid in 34% yield according to general procedure I.
Phenol: 2-Hydroxybenzonitrile
4-Hydroxy-cyclohexanecarboxylic acid ester: cis-4-Hydroxy-cyclohexanecarboxylic acid methyl ester
MS m/e: 260 (M+H$^+$)

4-Aryloxy-cyclohexanecarboxylic acid ester 14 trans-4-o-Tolyloxy-cyclohexanecarboxylic acid methyl ester

The title compound was obtained as colorless oil in 15% yield according to general procedure I.
Phenol: 2-Methylphenol
4-Hydroxy-cyclohexanecarboxylic acid ester: cis-4-Hydroxy-cyclohexanecarboxylic acid methyl ester
MS m/e: 248 (M$^+$)

4-Aryloxy-cyclohexanecarboxylic acid ester 15 trans-4-(3,5-Difluoro-phenoxy)-cyclohexanecarboxylic acid methyl ester

The title compound was obtained as off-white solid in 22% yield according to general procedure I.
Phenol: 3,5-Difluorophenol
4-Hydroxy-cyclohexanecarboxylic acid ester: cis-4-Hydroxy-cyclohexanecarboxylic acid methyl ester 4-Aryloxy-cyclohexanecarboxylic acid ester 16 trans-4-(Naphthalen-2-yloxy)-cyclohexanecarboxylic acid methyl ester

The title compound was obtained as yellow solid in 20% yield according to general procedure I.
Phenol: 2-Naphthol
4-Hydroxy-cyclohexanecarboxylic acid ester: cis-4-Hydroxy-cyclohexanecarboxylic acid methyl ester
MS m/e: 284 (M$^+$)

4-Aryloxy-cyclohexanecarboxylic acid ester 17 trans-4-(Naphthalen-1-yloxy)-cyclohexanecarboxylic acid methyl ester

The title compound was obtained as yellow solid in 20% yield according to general procedure I.
Phenol: 1-Naphthol
4-Hydroxy-cyclohexanecarboxylic acid ester: cis-4-Hydroxy-cyclohexanecarboxylic acid methyl ester
MS m/e: 284 (M$^+$)

4-Aryloxy-cyclohexanecarboxylic acid ester 18 trans-4-(Pyridin-3-yloxy)-cyclohexanecarboxylic acid methyl ester

The title compound was obtained as white solid in 25% yield according to general procedure I.
Phenol: 3-Hydroxypyridine
4-Hydroxy-cyclohexanecarboxylic acid ester: cis-4-Hydroxy-cyclohexanecarboxylic acid methyl ester
MS m/e: 236 (M+H$^+$)

4-Aryloxy-cyclohexanecarboxylic acid ester 19 trans-4-(5-Chloro-pyridin-3-yloxy)-cyclohexanecarboxylic acid methyl ester

The title compound was obtained as off-white solid in 29% yield according to general procedure I.
Phenol: 3-Chloro-5-hydroxypyridine
4-Hydroxy-cyclohexanecarboxylic acid ester: cis-4-Hydroxy-cyclohexanecarboxylic acid methyl ester
MS m/e: 270 (M+H$^+$)

4-Aryloxy-cyclohexanecarboxylic acid ester 20 trans-4-(Pyridin-2-yloxy)-cyclohexanecarboxylic acid methyl ester

The title compound was obtained as light red solid in 36% yield according to general procedure I.
Phenol: 2-Hydroxypyridine
4-Hydroxy-cyclohexanecarboxylic acid ester: cis-4-Hydroxy-cyclohexanecarboxylic acid methyl ester
MS m/e: 236 (M+H$^+$)

4-Aryloxy-cyclohexanecarboxylic acid ester 21 trans-4-(6-Chloro-pyridin-2-yloxy)-cyclohexanecarboxylic acid methyl ester

The title compound was obtained according to general procedure I.
Phenol: 6-Chloro-pyridin-2-ol
4-Hydroxy-cyclohexanecarboxylic acid ester: cis-4-Hydroxy-cyclohexanecarboxylic acid methyl ester
MS m/e: 270 (M+H$^+$)

4-Aryloxy-cyclohexanecarboxylic acid ester 22 trans-4-(5-Chloro-pyridin-2-yloxy)-cyclohexanecarboxylic acid methyl ester

The title compound was obtained according to general procedure I.
Phenol: 5-Chloro-pyridin-2-ol
4-Hydroxy-cyclohexanecarboxylic acid ester: cis-4-Hydroxy-cyclohexanecarboxylic acid methyl ester
MS m/e: 270 (M+H$^+$)

4-Aryloxy-cyclohexanecarboxylic acid ester 23 trans-4-(2,6-Dimethyl-pyrimidin-4-yloxy)-cyclohexanecarboxylic acid methyl ester The title compound was obtained as light yellow oil in 32% yield according to general procedure I.
Phenol: 2,4-Dimethyl-6-hydroxypyrimidine
4-Hydroxy-cyclohexanecarboxylic acid ester: cis-4-Hydroxy-cyclohexanecarboxylic acid methyl ester
MS m/e: 265 (M+H$^+$)

4-Aryloxy-cyclohexanecarboxylic acid ester 24 cis/trans-4-(Pyrimidin-2-yloxy)-cyclohexanecarboxylic acid ethyl ester (1:2)

The title compound was obtained as yellow amorphous solid in 24% yield according to general procedure III.
Heteroaryl chloride: 2-Chloropyrimidine
4-Hydroxy-cyclohexanecarboxylic acid ester: cis/trans-4-Hydroxy-cyclohexanecarboxylic acid ethyl ester (2:1)
MS m/e: 251 (M+H$^+$)

4-Aryloxy-cyclohexanecarboxylic acid ester 25 cis/trans-4-(Pyrazin-2-yloxy)-cyclohexanecarboxylic acid ethyl ester (1:1)

The title compound was obtained as white solid in 15% yield according to general procedure II.
Heteroaryl chloride: 2-Chloropyrazine
4-Hydroxy-cyclohexanecarboxylic acid ester: cis/trans-4-Hydroxy-cyclohexanecarboxylic acid ethyl ester ester (2:1)
MS m/e: 251 (M+H$^+$)

4-Aryloxy-cyclohexanecarboxylic acid ester 26 cis/trans-4-(6-Chloro-pyrimidin-4-yloxy)-cyclohexanecarboxylic acid ethyl ester (1:1)

The title compound was obtained as colorless oil in 38% yield according to general procedure III.
Heteroaryl chloride: 4,6-Dichloropyrimidine
4-Hydroxy-cyclohexanecarboxylic acid ester: cis/trans-4-Hydroxy-cyclohexanecarboxylic acid ethyl ester ester (2:1)
MS m/e: 284 (M$^+$)

4-Aryloxy-cyclohexanecarboxylic acid ester 27 cis/trans-4-(Pyrimidin-4-yloxy)-cyclohexanecarboxylic acid ethyl ester (1:1)

To an argon purged solution of cis/trans-4-(6-chloro-pyrimidin-4-yloxy)-cyclohexanecarboxylic acid ethyl ester (1:1) (1.05 g, 3.69 mmol) and triethylamine (0.52 ml, 3.69 mmol) in ethyl acetate (37 ml) was added palladium on charcoal 10% (0.078 g). The reaction mixture was purged with hydrogen gas and stirred under an atmosphere of hydrogen gas for 16 h at room temperature. The catalyst and the ammonium salts were removed by filtration over Decalite. The filtrate was concentrated in vacuo to give the title compound (0.92 g) as light yellow oil in quantitative yield. MS m/e: 251 (M+H$^+$).

4-Aryloxy-cyclohexanecarboxylic acid ester 28 cis/trans-4-(6-Chloro-pyridazin-3-yloxy)-cyclohexanecarboxylic acid ethyl ester (1:1)

The title compound was obtained as white solid in 39% yield according to general procedure III.
Heteroaryl chloride: 3,6-Dichloropyridazine
4-Hydroxy-cyclohexanecarboxylic acid ester: cis/trans-4-Hydroxy-cyclohexanecarboxylic acid ethyl ester (2:1)
MS m/e: 285 (M+H$^+$)

4-Aryloxy-cyclohexanecarboxylic acid ester 29 cis/trans-4-(Pyridazin-3-yloxy)-cyclohexanecarboxylic acid ethyl ester (1:1)

To an argon purged solution of cis/trans-4-(6-chloro-pyridazin-3-yloxy)-cyclohexanecarboxylic acid ethyl ester (1:1) (1.30 g, 4.57 mmol) and triethylamine (0.64 ml, 4.57 mmol) in ethyl acetate (46 ml) was added palladium on charcoal 10% (0.097 g). The reaction mixture was purged with hydrogen gas and stirred under an atmosphere of hydrogen gas for 4 h at room temperature. The catalyst and the ammonium salts were removed by filtration over Decalite. The filtrate was concentrated in vacuo to give the title compound (1.09 g, 95%) as light yellow oil.
MS m/e: 251 (M+H$^+$)

4-Aryloxy-cyclohexanecarboxylic acid ester 30 trans-4-(3-Fluoro-pyridin-2-yloxy)-cyclohexanecarboxylic acid methyl ester

The title compound was obtained according to general procedure I.
Phenol: 3-Fluoro-2-hydroxypyridine
4-Hydroxy-cyclohexanecarboxylic acid ester: cis-4-Hydroxy-cyclohexanecarboxylic acid methyl ester
MS m/e: 253 (M$^+$)

4-Aryloxy-cyclohexanecarboxylic acid ester 31 trans-4-(3-Fluoro-pyridin-2-yloxy)-cyclohexanecarboxylic acid methyl ester

The title compound was obtained according to general procedure I.
Phenol: 5-Fluoro-2-hydroxypyridine
4-Hydroxy-cyclohexanecarboxylic acid ester: cis-4-Hydroxy-cyclohexanecarboxylic acid methyl ester
MS m/e: 254 (M+H$^+$)

4-Aryloxy-cyclohexanecarboxylic acid ester 32 trans-4-(3-Fluoro-pyridin-2-yloxy)-cyclohexanecarboxylic acid methyl ester

The title compound was obtained according to general procedure I.
Phenol: 2-Hydroxy-6-methylpyridine
4-Hydroxy-cyclohexanecarboxylic acid ester: cis-4-Hydroxy-cyclohexanecarboxylic acid methyl ester
MS m/e: 250 (M+H$^+$)

4-Aryloxy-cyclohexanecarboxylic acid ester 33 cis-4-(Pyridin-2-yloxy)-cyclohexanecarboxylic acid methyl ester

The title compound was obtained according to general procedure I.
Phenol: 2-Hydroxypyridine
4-Hydroxy-cyclohexanecarboxylic acid ester: trans-4-Hydroxy-cyclohexanecarboxylic acid methyl ester
MS m/e: 236 (M+H$^+$)

4-Aryloxy-cyclohexanecarboxylic Acid Intermediates of Formula (VIII)

4-Aryloxy-cyclohexanecarboxylic acid 1 cis/trans-4-(Pyrimidin-2-yloxy)-cyclohexanecarboxylic acid (1:2)

To a solution of cis/trans-4-(pyrimidin-2-yloxy)-cyclohexanecarboxylic acid ethyl ester (1:2) (0.35 g, 1.4 mmol) in 1,4-dioxan (7 ml) was added 2 M aqueous sodium hydroxide solution (7.0 ml, 14 mmol). Stirring at room temperature for 16 h was followed by acidification to pH 2-3 with 0.5 M aqueous hydrogen chloride solution (50 ml) and extraction with three 100-ml portions of ethyl acetate. The combined organic layers were dried over anhydrous sodium sulfate and concentrated in vacuo to give the title compound (0.26 g, 83%) as yellow oil.
MS m/e: 221 (M−H$^+$).

4-Aryloxy-cyclohexanecarboxylic acid 2 cis/trans-4-(Pyrimidin-4-yloxy)-cyclohexanecarboxylic acid (1:1)

To a solution of cis/trans-4-(pyrimidin-4-yloxy)-cyclohexanecarboxylic acid ethyl ester (1:1) (0.90 g, 3.6 mmol) in 1,4-dioxane (18 ml) was added 2 M aqueous sodium hydroxide solution (18 ml, 36 mmol). Stirring at room temperature for 3 h was followed by acidification to pH 2-3 with 1 M aqueous hydrogen chloride solution (42 ml) and extraction with four 100-ml portions of ethyl acetate. The combined organic layers were dried over anhydrous sodium sulfate and concentrated in vacuo to give the title compound (0.76 g, 95%) as white solid.
MS m/e: 221 (M−H$^+$).

4-Aryloxy-cyclohexanecarboxylic acid 3 cis/trans-4-(Pyridazin-3-yloxy)-cyclohexanecarboxylic acid (1:1)

To a solution of cis/trans-4-(pyridazin-3-yloxy)-cyclohexanecarboxylic acid ethyl ester (1:1) (1.05 g, 4.19 mmol) in 1,4-dioxane (21 ml) was added 2 M aqueous sodium hydroxide solution (21 ml, 42 mmol). Stirring at room temperature for 16 h was followed by acidification to pH 2-3 with 1 M aqueous hydrogen chloride solution (44 ml) and extraction with three 100-ml portions of ethyl acetate. The combined organic layers were dried over anhydrous sodium sulfate and concentrated in vacuo to give the title compound (0.80 g, 86%) as off-white solid.
MS m/e: 221 (M−H$^+$).

Hydrazide Intermediates of Formula (II)

General Procedure IV: Conversion of Ester to Hydrazide

A mixture of 4-(aryloxy)-cyclohexanecarboxylic acid ester of formula (VI) (1 eq) and hydrazine hydrate (5 eq) is heated at 120° C. for 5 h. After cooling to room temperature the reaction mixture is partitioned between dichloromethane and water. The layers are separated and the organic layer is washed with water and brine. The organic layer is dried over anhydrous sodium sulfate and concentrated in vacuo to give the crude title compound, which is used in the next step without further purification.

Hydrazide 1 trans-4-Phenoxy-cyclohexanecarboxylic acid hydrazide

A mixture of trans-4-phenoxy-cyclohexanecarboxylic acid methyl ester (1.07 g, 4.57 mmol) and hydrazine hydrate (0.22 g, 4.48 mmol) was heated at 120° C. for 4 h. After cooling to room temperature the reaction mixture was concentrated in vacuo to give the crude title compound as white solid in quantitative yield, which was used in the next step without further purification.
MS m/e: 235 (M+H$^+$).

Hydrazide 2 cis-4-Phenoxy-cyclohexanecarboxylic acid hydrazide

A mixture of cis-4-phenoxy-cyclohexanecarboxylic acid methyl ester (0.55 g, 2.3 mmol) and hydrazine hydrate (0.11 g, 2.3 mmol) was heated at 120° C. for 24 h. After cooling to room temperature the reaction mixture was suspended in toluene (70 ml). After evaporation of the solvent, the residue was suspended in toluene (70 ml) again. The solvent was evaporated and the residue was dried in high vacuo (1-2 mbar) to give the crude title compound (0.50 g, 92%) as light yellow foam, which was used in the next step without further purification.
MS m/e: 235 (M+H$^+$).

Hydrazide 3 trans-4-(4-Fluoro-phenoxy)-cyclohexanecarboxylic acid hydrazide

A mixture of trans-4-(4-fluoro-phenoxy)-cyclohexanecarboxylic acid methyl ester (0.23 g, 0.93 mmol) and hydrazine hydrate (0.046 g, 0.91 mmol) was heated at 120° C. for 3.5 h. After cooling to room temperature the reaction mixture was suspended in toluene (70 ml). After evaporation of the solvent, the residue was suspended in toluene (70 ml) again. The solvent was evaporated and the residue was dried in high vacuo (1-2 mbar) to give the crude title compound (0.22 g, 96%) as white solid, which was used in the next step without further purification. MS m/e: 253 (M+H$^+$).

Hydrazide 4 trans-4-(4-Cyano-phenoxy)-cyclohexanecarboxylic acid hydrazide

The title compound was obtained from trans-4-(4-cyano-phenoxy)-cyclohexanecarboxylic acid methyl ester according to general procedure IV. MS m/e: 260 (M+H$^+$).

Hydrazide 5 trans-4-(4-Trifluoromethyl-phenoxy)-cyclohexanecarboxylic acid hydrazide

The title compound was obtained from trans-4-(4-trifluoromethyl-phenoxy)-cyclohexanecarboxylic acid methyl ester according to general procedure IV.
MS m/e: 303 (M+H$^+$)

Hydrazide 6 trans-4-(3-Chloro-phenoxy)-cyclohexanecarboxylic acid hydrazide

A mixture of trans-4-(3-chloro-phenoxy)-cyclohexanecarboxylic acid methyl ester (0.25 g, 0.93 mmol) and hydrazine hydrate (0.044 ml, 0.91 mmol) was heated at 120° C. for 22 h. Addition of further hydrazine hydrate (0.020 ml, 0.42 mmol) was followed by stirring at 120° C. for 5 h. After cooling to room temperature the reaction mixture was partitioned between ethyl acetate (50 ml) and 1 M aqueous sodium hydroxide solution (50 ml). The layers were separated and the aqueous layer was extracted with a 50-ml portion of ethyl acetate. The combined organic layers were dried over anhydrous sodium sulfate and concentrated in vacuo to give the crude title compound (0.21 g, 86%) as white solid, which was used in the next step without further purification. MS m/e: 269 (M+H$^+$)

Hydrazide 7 trans-4-(3-Methoxy-phenoxy)-cyclohexanecarboxylic acid hydrazide

A mixture of trans-4-(3-methoxy-phenoxy)-cyclohexanecarboxylic acid methyl ester (0.20 g, 0.75 mmol) and hydrazine hydrate (0.035 ml, 0.73 mmol) was heated at 120° C. for 22 h. After cooling to room temperature the reaction mixture was partitioned between ethyl acetate (50 ml) and 1 M aqueous sodium hydroxide solution (50 ml). The organic layer was separated, dried over anhydrous sodium sulfate and concentrated in vacuo to give the crude title compound (0.18 g, 92%) as white solid, which was used in the next step without further purification.
MS m/e: 265 (M+H$^+$)

Hydrazide 8 trans-4-(3-Cyano-phenoxy)-cyclohexanecarboxylic acid hydrazide

A mixture of trans-4-(3-cyano-phenoxy)-cyclohexanecarboxylic acid methyl ester (0.277 g, 1.07 mmol) and hydrazine hydrate (0.104 ml, 2.14 mmol) in n-butanol (0.5 ml) was heated at 120° C. for 18 h. After cooling to room temperature the reaction mixture was partitioned between ethyl acetate (50 ml) and 1 M aqueous sodium hydroxide solution (50 ml). The layers were separated and the aqueous layer was extracted with a 50-ml portion of ethyl acetate. The combined organic layers were dried over anhydrous sodium sulfate and concentrated in vacuo. The residue was triturated in methanol (7 ml). The solids were removed by filtration and the filtrate was concentrated in vacuo to give the crude title compound (0.15 g, 55%) as light red solid, which was used in the next step without further purification. MS m/e: 260 (M+H$^+$)

Hydrazide 9 trans-4-m-Tolyloxy-cyclohexanecarboxylic acid hydrazide

The title compound was obtained from trans-4-m-tolyloxy-cyclohexanecarboxylic acid methyl ester according to general procedure IV. MS m/e: 249 (M+H$^+$)

Hydrazide 10 trans-4-(3-tert-Butyl-phenoxy)-cyclohexanecarboxylic acid hydrazide

The title compound was obtained from trans-4-(3-tert-butyl-phenoxy)-cyclohexanecarboxylic acid methyl ester according to general procedure IV.

Hydrazide 11 trans-4-(3-Trifluoromethyl-phenoxy)-cyclohexanecarboxylic acid hydrazide

The title compound was obtained from trans-4-(3-trifluoromethyl-phenoxy)-cyclohexanecarboxylic acid methyl ester according to general procedure IV.
MS m/e: 303 (M+H$^+$)

Hydrazide 12 trans-4-(2-Fluoro-phenoxy)-cyclohexanecarboxylic acid hydrazide

The title compound was obtained from trans-4-(2-fluoro-phenoxy)-cyclohexanecarboxylic acid methyl ester according to general procedure IV.

Hydrazide 13 trans-4-(2-Cyano-phenoxy)-cyclohexanecarboxylic acid hydrazide

A mixture of trans-4-(2-cyano-phenoxy)-cyclohexanecarboxylic acid methyl ester (0.20 g, 0.77 mmol) and hydrazine hydrate (0.037 ml, 0.76 mmol) in n-butanol (0.5 ml) was heated at 120° C. for 22 h. After cooling to room temperature the reaction mixture was partitioned between ethyl acetate (50 ml) and 1 M aqueous sodium hydroxide solution (50 ml). The organic layer was separated, dried over anhydrous sodium sulfate and concentrated in vacuo to give the crude title compound (0.18 g, 90%) as white solid, which was used in the next step without further purification. MS m/e: 260 (M+H$^+$)

Hydrazide 14 trans-4-o-Tolyloxy-cyclohexanecarboxylic acid hydrazide

A mixture of trans-4-o-tolyloxy-cyclohexanecarboxylic acid methyl ester (0.091 g, 0.36 mmol) and hydrazine hydrate (0.02 ml, 0.36 mmol) was heated at 120° C. for 22 h. After cooling to room temperature the reaction mixture was suspended in toluene. After evaporation of the solvent the residue was dried in high vacuo (1-2 mbar) to give the crude title compound (0.73 g, 81%) as white solid, which was used in the next step without further purification.
MS m/e: 249 (M+H$^+$)

Hydrazide 15 trans-4-(3,5-Difluoro-phenoxy)-cyclohexanecarboxylic acid hydrazide

A mixture of trans-4-(3,5-difluoro-phenoxy)-cyclohexanecarboxylic acid methyl ester (0.148 g, 0.548 mmol) and hydrazine hydrate (0.106 ml, 2.19 mmol) was heated at 120° C. for 18 h. After cooling to room temperature the reaction mixture was partitioned between ethyl acetate (50 ml) and 1 M aqueous sodium hydroxide solution (50 ml). The organic layer was separated.

The aqueous layer was extracted with one portion of ethyl acetate (50 ml). The combined organic layers were dried over anhydrous sodium sulfate and concentrated in vacuo to give the crude title compound (0.14 g, 96%) as light yellow solid, which was used in the next step without further purification. MS m/e: 271 (M+H$^+$)

Hydrazide 16 trans-4-(Naphthalen-2-yloxy)-cyclohexanecarboxylic acid hydrazide

A mixture of trans-4-(naphthalen-2-yloxy)-cyclohexanecarboxylic acid methyl ester (0.130 g, 0.457 mmol) and hydrazine hydrate (0.02 ml, 0.45 mmol) in methanol (0.5 ml) was heated at 80° C. for 16 h. After cooling to room temperature the reaction mixture was partitioned between ethyl acetate (50 ml) and 1 M aqueous sodium hydroxide solution (50 ml). The organic layer was separated, dried over anhydrous sodium sulfate and concentrated in vacuo to give the crude title compound (0.112 g, 86%) as yellow solid, which was used in the next step without further purification. MS m/e: 285 (M+H$^+$)

Hydrazide 17 trans-4-(Naphthalen-1-yloxy)-cyclohexanecarboxylic acid hydrazide

A mixture of trans-4-(naphthalen-1-yloxy)-cyclohexanecarboxylic acid methyl ester (0.130 g, 0.457 mmol) and hydrazine hydrate (0.022 ml, 0.45 mmol) in methanol (0.5 ml) was heated at 80° C. for 16 h. After cooling to room temperature the reaction mixture was partitioned between ethyl acetate (50 ml) and 1 M aqueous sodium hydroxide solution (50 ml). The organic layer was separated. The aqueous layer was extracted with two 50-ml portions of ethyl acetate. The combined organic layers were dried over anhydrous sodium sulfate and concentrated in vacuo to give a 3:1 mixture of the crude title compound and starting material. This mixture (0.12 g) and hydrazine hydrate (0.022 ml, 0.45 mmol) were dissolved in 1,4-dioxane (0.4 ml) and heated at reflux for 18 h. After cooling to room temperature the reaction mixture was partitioned between ethyl acetate (50 ml) and 1 M aqueous sodium hydroxide solution (50 ml). The organic layer was separated. The aqueous layer was extracted with two 50-ml portions of ethyl acetate. The combined organic layers were dried over anhydrous sodium sulfate and concentrated in vacuo to give the crude title compound (0.120 g, 83%) as yellow solid with a purity of 90%, which was used in the next step without further purification. MS m/e: 285 (M+H$^+$)

Hydrazide 18 trans-4-(Pyridin-3-yloxy)-cyclohexanecarboxylic acid hydrazide

A mixture of trans-4-(pyridin-3-yloxy)-cyclohexanecarboxylic acid methyl ester (0.141 g, 0.599 mmol) and hydrazine hydrate (0.029 ml, 0.59 mmol) in n-butanol (0.5 ml) was heated at 120° C. for 22 h. After cooling to room temperature the reaction mixture was partitioned between ethyl acetate (50 ml) and 1 M aqueous sodium hydroxide solution (50 ml). The organic layer was separated, dried over anhydrous sodium sulfate and concentrated in vacuo to give the crude title compound (0.061 g, 43%) as white solid, which was used in the next step without further purification. MS m/e: 236 (M+H$^+$)

Hydrazide 19 trans-4-(5-Chloro-pyridin-3-yloxy)-cyclohexanecarboxylic acid hydrazide

A mixture of trans-4-(5-chloro-pyridin-3-yloxy)-cyclohexanecarboxylic acid methyl ester (0.19 g, 0.70 mmol) and hydrazine hydrate (0.14 ml, 2.8 mmol) in n-butanol (0.5 ml) was heated at 120° C. for 18 h. After cooling to room temperature the reaction mixture was triturated in toluene (100 ml). The product was collected by filtration and dried in vacuo to give the crude title compound (0.15 g, 79%) as white solid, which was used in the next step without further purification. MS m/e: 270 (M+H$^+$)

Hydrazide 20 trans-4-(Pyridin-2-yloxy)-cyclohexanecarboxylic acid hydrazide

A mixture of trans-4-(pyridin-2-yloxy)-cyclohexanecarboxylic acid methyl ester (1.33 g, 5.66 mmol) and hydrazine hydrate (0.55 ml, 11 mmol) in n-butanol (1 ml) was heated at 120° C. for 68 h. After cooling to room temperature the reaction mixture was evaporated and dried in high vacuo (ca. 1-2 mbar) at 100° C. for 2 h to give the crude title compound (1.28 g, 96%) as white solid, which was used in the next step without further purification. MS m/e: 236 (M+H$^+$)

Hydrazide 21 trans-4-(6-Chloro-pyridin-2-yloxy)-cyclohexanecarboxylic acid hydrazide

The title compound was obtained from trans-4-(6-chloro-pyridin-2-yloxy)-cyclohexanecarboxylic acid methyl ester according to general procedure IV.
MS m/e: 270 (M+H$^+$)

Hydrazide 22 trans-4-(5-Chloro-pyridin-2-yloxy)-cyclohexanecarboxylic acid hydrazide

The title compound was obtained from trans-4-(5-chloro-pyridin-2-yloxy)-cyclohexanecarboxylic acid methyl ester according to general procedure IV.

Hydrazide 23 trans-4-(2,6-Dimethyl-pyrimidin-4-yloxy)-cyclohexanecarboxylic acid hydrazide

A mixture of trans-4-(2,6-dimethyl-pyrimidin-4-yloxy)-cyclohexanecarboxylic acid methyl ester (0.20 g, 0.76 mmol) and hydrazine hydrate (0.15 ml, 3.0 mmol) in n-butanol (0.5 ml) was heated at reflux over night. The reaction mixture was evaporated and dried in high vacuo (ca. 1-2 mbar) to give the crude title compound (0.19 g, 95%) as white solid, which was used in the next step without further purification. MS m/e: 265 (M+H$^+$)

Hydrazide 24 cis/trans-4-(Pyrimidin-2-yloxy)-cyclohexanecarboxylic acid hydrazide (1:2)

To a solution of cis/trans-4-(pyrimidin-2-yloxy)-cyclohexanecarboxylic acid (1:2) (0.258 g, 1.16 mmol) and triethylamine (0.162 ml, 1.16 mmol) in THF (6 ml) was added ethyl chloroformate (0.111 ml, 1.16 mmol) at 0° C. The reaction mixture was stirred for 1 h. The ammonium salts were removed by filtration. The filtrate was added to a cold solution of hydrazine hydrate (0.116 g, 2.32 mmol) in methanol (10 ml). The reaction mixture was stirred for 2 h at room temperature and then partitioned between ethyl acetate (50 ml) and a mixture of a 1:1 mixture of 1 M aqueous sodium hydroxide solution and brine (50 ml). The layers were separated. The aqueous layer was extracted with five 50-ml portions of ethyl acetate. The combined organic layers were dried over anhydrous sodium sulfate and concentrated in vacuo to give the crude title compound (0.177 g, 65%) as white solid, which was used in the next step without further purification. MS m/e: 237 (M+H$^+$)

Hydrazide 25 trans-4-(Pyrazin-2-yloxy)-cyclohexanecarboxylic acid hydrazide

A mixture of cis/trans-4-(pyrazin-2-yloxy)-cyclohexanecarboxylic acid ethyl ester (1.11 g, 4.41 mmol) and hydrazine hydrate (0442 g, 8.83 mmol) was heated at 120° C. for 72 h. After cooling to room temperature the reaction mixture was partitioned between ethyl acetate (50 ml) and water (30 ml). The organic layer was separated. The aqueous layer was extracted with two 50 ml portions of ethyl acetate. The combined organic layers were washed with brine (30 ml), dried over anhydrous sodium sulfate and concentrated in vacuo. The crude cis/trans-hydrazide was triturated in ethyl acetate (5 ml). The precipitate was collected by filtration and dried in vacuo to give the crude title compound (0.236 g, 23%) as white solid, which was used in the next step without further purification. MS m/e: 237 (M+H$^+$)

Hydrazide 26 cis/trans-4-(Pyrimidin-4-yloxy)-cyclohexanecarboxylic acid hydrazide (1:1)

To a solution of cis/trans-4-(pyrimidin-4-yloxy)-cyclohexanecarboxylic acid (1:1) (0.750 g, 3.37 mmol) and triethylamine (0.470 ml, 3.37 mmol) in THF (16 ml) was added ethyl chloroformate (0.322 ml, 3.37 mmol) at 0° C. The reaction mixture was stirred for 1 h. The ammonium salts were removed by filtration. The filtrate was added to a cold solution of hydrazine hydrate (0.338 g, 6.75 mmol) in methanol (20 ml). The reaction mixture was stirred for 2 h at room temperature. The solvent was evaporated under reduced pressure and the residue was partitioned between ethyl acetate (100 ml) and a 1:1 mixture of 1 M aqueous sodium hydroxide solution and brine (30 ml). The organic layer was separated. The aqueous layer was extracted with three 100-ml portions of ethyl acetate. The combined organic layers were dried over anhydrous sodium sulfate and concentrated in vacuo to give the crude title compound (0.588 g, 74%) as off-white solid, which was used in the next step without further purification. MS m/e: 237 (M+H$^+$)

Hydrazide 27 cis/trans-4-(Pyridazin-3-yloxy)-cyclohexanecarboxylic acid hydrazide (1:1)

To a solution of cis/trans-4-(pyridazin-3-yloxy)-cyclohexanecarboxylic acid (1:1) (0.780 g, 3.51 mmol) and triethylamine (0.489 ml, 3.37 mmol) in THF (17 ml) was added ethyl chloroformate (0.334 ml, 3.51 mmol) at 0° C. The reaction mixture was stirred for 1 h. The ammonium salts were removed by filtration. The filtrate was added to a cold solution of hydrazine hydrate (0.351 g, 7.02 mmol) in methanol (20 ml). The reaction mixture was stirred for 2 h at room temperature. The solvent was evaporated under reduced pressure and the residue was partitioned between ethyl acetate (100 ml) and a 1:1 mixture of 1 M aqueous sodium hydroxide solution and brine (30 ml). The organic layer was separated. The aqueous layer was extracted with five 75-ml portions of ethyl acetate. The combined organic layers were dried over anhydrous sodium sulfate and concentrated in vacuo to give the crude title compound (0.580 g, 70%) as off-white solid, which was used in the next step without further purification. MS m/e: 237 (M+H$^+$)

Hydrazide 28 trans-4-(3-Fluoro-pyridin-2-yloxy)-cyclohexanecarboxylic acid hydrazide

A mixture of trans-4-(3-fluoro-pyridin-2-yloxy)-cyclohexanecarboxylic acid methyl ester (0.60 g, 2.4 mmol) and hydrazine hydrate (0.53 ml, 11 mmol) in n-butanol (1 ml) was heated at 125° C. for 4 h. After cooling to room temperature the reaction mixture was partitioned between dichloromethane (75 ml) and water (75 ml). The aqueous layer was washed with dichloromethane/75 ml). The combined organic layers were washed with water (75 ml) and brine (75 ml), dried over anhydrous sodium sulfate and concentrated in vacuo to give the crude title compound (0.45 g, 83%) as white solid, which was used in the next step without further purification. MS m/e: 254 (M+H$^+$)

Hydrazide 29 trans-4-(5-Fluoro-pyridin-2-yloxy)-cyclohexanecarboxylic acid hydrazide

A mixture of trans-4-(5-fluoro-pyridin-2-yloxy)-cyclohexanecarboxylic acid methyl ester (0.92 g, 3.6 mmol) and hydrazine hydrate (0.80 ml, 16 mmol) in n-butanol (1 ml) was heated at 125° C. for 4 h. After cooling to room temperature the reaction mixture was partitioned between dichloromethane (75 ml) and water (75 ml). The aqueous layer was washed with dichloromethane/75 ml). The combined organic layers were washed with water (75 ml) and brine (75 ml), dried over anhydrous sodium sulfate and concentrated in vacuo to give the crude title compound (0.55 g, 67%) as white solid, which was used in the next step without further purification. MS m/e: 254 (M+H$^+$)

Hydrazide 30 trans-4-(6-Methyl-pyridin-2-yloxy)-cyclohexanecarboxylic acid hydrazide

A mixture of trans-4-(6-methyl-pyridin-2-yloxy)-cyclohexanecarboxylic acid methyl ester (0.62 g, 2.5 mmol) and hydrazine hydrate (0.55 ml, 11 mmol) in n-butanol (1 ml) was heated at 125° C. for 4 h. After cooling to room temperature the reaction mixture was partitioned between dichloromethane (75 ml) and water (75 ml). The aqueous layer was washed with dichloromethane/75 ml). The combined organic layers were washed with water (75 ml) and brine (75 ml), dried over anhydrous sodium sulfate and concentrated in vacuo to give the crude title compound (0.48 g, 86%) as white solid, which was used in the next step without further purification. MS m/e: 250 (M+H$^+$)

Hydrazide 31 cis-4-(Pyridin-2-yloxy)-cyclohexanecarboxylic acid hydrazide

A mixture of cis-4-(pyridin-2-yloxy)-cyclohexanecarboxylic acid methyl ester (0.39 g, 1.6 mmol) and hydrazine hydrate (0.40 ml, 8.2 mmol) in n-butanol (0.5 ml) was heated at 125° C. over night. After cooling to room temperature the reaction mixture was partitioned between dichloromethane (75 ml) and water (75 ml). The aqueous layer was washed with dichloromethane/75 ml). The combined organic layers were washed with water (75 ml) and brine (75 ml), dried over anhydrous sodium sulfate and concentrated in vacuo to give the crude title compound (0.35 g, 91%) as colorless oil, which was used in the next step without further purification. MS m/e: 236 (M+H$^+$)

Thiolactam Intermediates of Formula (III)

7-Chloro-2-thioxo-1,2,3,5-tetrahydro-benzo[e][1,4]diazepine-4-carboxylic acid tert-butyl ester a) 4-Chloro-2-chloromethyl-1-nitro-benzene

To a solution of 5-chloro-2-nitrobenzyl alcohol (80 g, 0.42 mol) and triethylamine (64 ml, 0.46 mol) in dichloromethane (840 ml) was added drop wise thionyl chloride (34 ml, 0.46 mol) during a period of 30 min while the internal temperature was kept below 32° C. by cooling with a water bath. The reaction mixture was stirred for 3 h. The solvent was evaporated and the residue was triturated in warm tert-butyl methyl ether (970 ml). The ammonium salts were removed by filtration and the filtrate was concentrated in vacuo to give the title compound (85 g, 99%) as brown oil which was used in the next step without purification. MS m/e: 205 (M$^+$).

b) (5-Chloro-2-nitro-benzylamino)-acetic acid ethyl ester

A mixture of 4-chloro-2-chloromethyl-1-nitro-benzene (85 g, 0.41 mol), glycine ethyl ester hydrochloride (70 g, 0.50 mol) and triethylamine (121.4 ml, 0.8665 mol) in ethanol (1000 ml) was heated at reflux for 8 h. The solvent was evaporated and the residue was triturated in warm tert-butyl methyl ether. The ammonium salts were removed by filtration and the filtrate was concentrated in vacuo to give the title compound (111 g, 99%) as an amorphous brown solid which was used in the next step without purification. MS m/e: 273 (M+H$^+$).

c) [tert-Butoxycarbonyl-(5-chloro-2-nitro-benzyl)-amino]acetic acid ethyl ester A solution of (5-chloro-2-nitro-benzylamino)-acetic acid ethyl ester (110 g, 0.403 mol), di-tert-butyl dicarbonate (180 g, 0.807 mol) and 4-N,N-dimethylaminopyridine (2.51 g, 0.0202 mol) in dichloromethane (1200 ml) was stirred for 2 h at 0° C. and further 16 h at room temperature. The solvent was evaporated and the crude product was purified by flash chromatography with a cyclohexane/ethyl acetate mixture as eluent to give the title compound (76.4 g, 51%) as light yellow viscous oil. MS m/e: 373 (M+H$^+$).

d) [(2-Amino-5-chloro-benzyl)-tert-butoxycarbonyl-amino]-acetic acid ethyl ester To a solution of [tert-butoxycarbonyl-(5-chloro-2-nitro-benzyl)-amino]-acetic acid ethyl ester (69.0 g, 0.186 mol) in ethyl acetate (1200 ml) was added zinc bromide (8.5 g, 0.037 mol). The reaction mixture was purged with argon after 15 min. After addition of the palladium catalyst (10% on activated charcoal, 7.9 g, 0.0074 mol) the mixture was hydrogenated at ambient pressure during a period of ca. 48 h until ca. 131 of hydrogen gas had been consumed. The catalyst was removed by filtration and the filtrate was washed with two portions of saturated aqueous sodium bicarbonate solution and brine, each. The organic layer was dried over anhydrous sodium sulfate and concentrated in vacuo to give the title compound (60.6 g, 95.5%) as yellow waxy solid. MS m/e: 343 (M+H$^+$).

e) 7-Chloro-2-oxo-1,2,3,5-tetrahydro-benzo[1,4]diazepine-4-carboxylic acid tert-butyl ester To a solution of [(2-amino-5-chloro-benzyl)-tert-butoxycarbonyl-amino]-acetic acid ethyl ester (60 g, 0.18 mol) in tetrahydrofuran (600 ml) was added potassium tert-butoxide (22 g, 0.19 mol) in small portions at 5° C. under cooling on an ice-water batch. After completed addition the cooling bath was removed and reaction mixture was stirred for 3 h at room temperature followed by addition of water (400 ml), saturated aqueous ammonium chloride solution (280 ml) and ethyl acetate (800 ml). After 10 min the precipitate was collected by filtration. The organic layer was separated from the filtrate, dried over anhydrous sodium sulfate and concentrated in vacuo. The residue was combined with the precipitate, which had previously been collected by filtration, and crystallized from hot ethyl acetate to give the title compound (46 g, 88%) as white solid.

MS m/e: 295 (M–H$^+$).

f) 7-Chloro-2-thioxo-1,2,3,5-tetrahydro-benzo[e][1,4]diazepine-4-carboxylic acid tert-butyl ester A mixture of 7-chloro-2-oxo-1,2,3,5-tetrahydro-benzo[1,4]diazepine-4-carboxylic acid tert-butyl ester (41.1 g, 0.139 mol) and 2,4-bis-(4-methoxyphenyl)-1,3,2,4-dithiadiphosphetane-2,4-disulfide (31.5 g, 0.0763 mol) in tetrahydrofuran (1100 ml) was heated at reflux for 3 h. The solvent was evaporated and the residue was triturated in tert-butyl methyl ether. The precipitate was removed by filtration and the filtrate was concentrated to dryness. The residue was crystallized from hot ethanol to give the title compound (37.5 g, 86.4%) as light yellow solid.

MS m/e: 311 (M−H⁺).

7-Fluoro-2-thioxo-1,2,3,5-tetrahydro-benzo[e][1,4]diazepine-4-carboxylic acid tert-butyl ester The title compound was obtained as light yellow solid in comparable yields according to the procedures described above for the synthesis of 7-chloro-2-thioxo-1,2,3,5-tetrahydro-benzo[e][1,4]diazepine-4-carboxylic acid tert-butyl ester using 5-fluoro-2-nitrobenzyl alcohol instead of 5-chloro-2-nitrobenzyl alcohol in step a). MS m/e: 297 (M−H⁺).

EXAMPLES

General Procedure V: Condensation of Hydrazide and Thiolactam to Triazole

A mixture of a hydrazide derivative of formula (II) (1-1.5 eq) and a thiolactam of formula (III) (1 eq) in n-butanol (0.1-0.2 M) is heated at reflux for 16-72 h. After cooling to room temperature the solvent is evaporated and the residue is purified by flash-chromatography to give a compound of formula (I). When a thiolactam of formula (III-1) (compounds of formula (III) in which $R^2$ is tert-butoxycarbonyl) is used the N-tert-butoxycarbonyl group of the resulting triazole product of formula (I-a) can be partially or completely cleaved thermally, and a secondary amine derivative of formula (I-b) is obtained in addition or as the sole product.

General Procedure VI: Cleavage of N-Tert-Butoxycarbonyl (N—BOC) Group

A solution of an N—BOC derivative of general formula (I-a) (1 eq) in 1.25 M methanolic or 1.5 M ethanolic hydrogen chloride solution (10-20 eq HCl) is heated at 50° C. for 15-60 min. After cooling to room temperature the reaction mixture is concentrated in vacuo to give a secondary amine derivative of general formula (I-b) as hydrochloride salt. Optionally the free base can be obtained by partitioning the hydrochloride salt between 1 M aqueous sodium hydroxide solution and an organic solvent, e.g. ethyl acetate or dichloromethane. The layers are separated and the aqueous layer is extracted with two portions of the organic solvent. The combined organic layers are dried over anhydrous sodium sulfate, filtered and concentrated in vacuo to give the free base of a compound of formula (I-b).

General Procedure VII: Reductive N-Alkylation

A mixture of a compound of formula (I-b) as free base or as hydrochloride salt (1 eq, 0.1-0.2 M), triethylamine (1 eq when the hydrochloride salt of a compound of formula (I-b) is used) and an aldehyde or ketone (8 eq) in methanol is heated at reflux for 2-6 h. After cooling to 0° C. sodium cyanoborohydride (2-3 eq) is added. The reaction mixture is stirred for 3-16 h at room temperature and quenched with 1 M aqueous sodium hydroxide solution. The aqueous layer is extracted with ethyl acetate. The combined organic layers are dried over anhydrous sodium sulfate and concentrated in vacuo. Flash chromatography gives an N-alkyl derivative of formula (I).

Example 1 trans-8-Chloro-1-(4-phenoxy-cyclohexyl)-4H,6H-2,3,5,10b-tetraaza-benzoazulene-5-carboxylic acid tert-butyl ester The title compound was obtained as white foam in 83% yield according to general procedure V. Hydrazide: trans-4-Phenoxy-cyclohexanecarboxylic acid hydrazide Thiolactam: 7-Chloro-2-thioxo-1,2,3,5-tetrahydro-benzo[e][1,4]diazepine-4-carboxylic acid tert-butyl ester MS m/e: 495 (M+H⁺)

Example 2 trans-8-Chloro-1-(4-phenoxy-cyclohexyl)-5,6-dihydro-4H-2,3,5,10b-tetraaza-benzoazulene hydrochloride The title compound was obtained as white solid in 98% yield from trans-8-chloro-1-(4-phenoxy-cyclohexyl)-4H,6H-2,3,5,10b-tetraaza-benzoazulene-5-carboxylic acid tert-butyl ester according to general procedure VI. MS m/e: 395 (M+H⁺)

Example 3 trans-8-Chloro-5-methyl-1-(4-phenoxy-cyclohexyl)-5,6-dihydro-4H-2,3,5,10b-tetraaza-benzo[e]azulene The title compound was obtained as white solid in 64% yield from trans-8-chloro-1-(4-phenoxy-cyclohexyl)-5,6-dihydro-4H-2,3,5,10b-tetraaza-benzoazulene hydrochloride and paraformaldehyde according to general procedure VII. MS m/e: 409 (M+H⁺).

Example 4 trans-1-[8-Chloro-1-(4-phenoxy-cyclohexyl)-4H,6H-2,3,5,10b-tetraaza-benzoazulen-5-yl]-ethanone To a solution of trans-8-chloro-1-(4-phenoxy-cyclohexyl)-5,6-dihydro-4H-2,3,5,10b-tetraaza-benzoazulene hydrochloride (0.071 g, 0.18 mmol) and triethylamine (0.048 ml, 0.35 mmol) in dichloromethane was added acetyl chloride (0.013 ml, 0.18 mmol) at room temperature. Stirring for 18 h was followed by partitioning between 1 M aqueous sodium hydroxide solution (50 ml) and dichloromethane (50 ml). The organic layer was separated. The aqueous layer was extracted with one 50-ml portion of dichloromethane. The combined organic layers were dried over anhydrous sodium sulfate and concentrated in vacuo. Purification by flash-chromatography with n-heptane/ethyl acetate as eluent gave the title compound (0.039 g, 54%) as white solid.

MS m/e: 437 (M+H⁺).

Example 5 trans-8-Chloro-5-methanesulfonyl-1-(4-phenoxy-cyclohexyl)-5,6-dihydro-4H-2,3,5,10b-tetraaza-benzoazulene To a solution of trans-8-chloro-1-(4-phenoxy-cyclohexyl)-5,6-dihydro-4H-2,3,5,10b-tetraaza-benzoazulene hydrochloride (0.065 g, 0.15 mmol) and triethylamine (0.044 ml, 0.32 mmol) in dichloromethane (5 ml) was added methanesulfonyl chloride (0.013 ml, 0.17 mmol) at room temperature. After stirring for 20 h the reaction mixture was transferred directly onto a silica gel chromatography column Elution with n-heptane/ethyl acetate gave the title compound (0.051 g, 72%) as white solid. MS m/e: 473 (M+H⁺).

Example 6 trans-2-[8-Chloro-1-(4-phenoxy-cyclohexyl)-4H,6H-2,3,5,10b-tetraaza-benzoazulen-5-yl]-ethanol The title compound was obtained as white solid in 59% yield from trans-8-chloro-1-(4-phenoxy-cyclohexyl)-5,6-dihydro-4H-2,3,5,10b-tetraaza-benzoazulene hydrochloride and glycolaldehyde according to general procedure VII. MS m/e: 439 (M+H$^+$).

Example 7 trans-8-Chloro-5-isopropyl-1-(4-phenoxy-cyclohexyl)-5,6-dihydro-4H-2,3,5,10b-tetraaza-benzoazulene The title compound was obtained as white solid in 45% yield from trans-8-chloro-1-(4-phenoxy-cyclohexyl)-5,6-dihydro-4H-2,3,5,10b-tetraaza-benzoazulene hydrochloride and acetone according to general procedure VII. MS m/e: 437 (M+H$^+$).

Example 8 trans-8-Chloro-1-(4-phenoxy-cyclohexyl)-4H,6H-2,3,5,10b-tetraaza-benzoazulene-5-sulfonic acid dimethylamide To a solution of trans-8-chloro-1-(4-phenoxy-cyclohexyl)-5,6-dihydro-4H-2,3,5,10b-tetraaza-benzoazulene hydrochloride (0.062 g, 0.14 mmol) and triethylamine (0.030 ml, 0.22 mmol) in dichloromethane (2.5 ml) was added N,N-dimethylsulfamoyl chloride (0.023 ml, 0.22 mmol) at room temperature. After stirring for 72 h the reaction mixture was transferred directly onto a silica gel chromatography column. Elution with n-heptane/ethyl acetate gave the title compound (0.042 g, 58%) as white solid. MS m/e: 502 (M+H$^+$).

Example 9 trans-8-Chloro-1-(4-phenoxy-cyclohexyl)-5-pyridin-2-ylmethyl-5,6-dihydro-4H-2,3,5,10b-tetraaza-benzoazulene To a mixture of trans-8-chloro-1-(4-phenoxy-cyclohexyl)-5,6-dihydro-4H-2,3,5,10b-tetraaza-benzoazulene hydrochloride (0.064 g, 0.15 mmol) and potassium carbonate (0.062 ml, 0.45 mmol) in acetonitrile (1 ml) was added 2-(bromomethyl)pyridine hydrobromide (0.040 ml, 0.16 mmol) at room temperature. Stirring for 72 h at 50° C. was followed by partitioning between 1 M aqueous sodium hydroxide solution (50 ml) and dichloromethane (50 ml). The organic layer was separated. The aqueous layer was extracted with two 50-ml portions of dichloromethane. The combined organic layers were dried over anhydrous sodium sulfate and concentrated in vacuo. Purification by flash-chromatography with n-heptane/ethyl acetate as eluent gave the title compound (0.044 g, 63%) as light brown solid. MS m/e: 486 (M+H$^+$).

Example 10 trans-1-[8-Chloro-1-(4-phenoxy-cyclohexyl)-4H,6H-2,3,5,10b-tetraaza-benzoazulen-5-yl]-2-dimethylamino-ethanone To a mixture of trans-8-chloro-1-(4-phenoxy-cyclohexyl)-5,6-dihydro-4H-2,3,5,10b-tetraaza-benzoazulene hydrochloride (0.179 g, 0.41 mmol) in tetrahydrofuran (2 ml) was added triethylamine (0.058 ml, 0.41 mmol). The suspension was stirred for 10 minutes. The ammonium salts were removed by filtration. The filtrate was concentrated in vacuo. The residue was redissolved in tetrahydrofuran (3 ml) followed by consecutive addition of N,N-dimethylglycine (0.056 g, 0.54 mmol) and N-(3-dimethylaminopropyl)-N'-ethylcarbodiimide hydrochloride (0.104 g, 0.54 mmol Stirring for 18 h at 50° C. was followed by partitioning between water (50 ml) and dichloromethane (50 ml). The organic layer was separated. The aqueous layer was extracted with one 50-ml portion of dichloromethane. The combined organic layers were dried over anhydrous sodium sulfate and concentrated in vacuo. Purification by flash-chromatography with n-heptane/ethyl acetate as eluent gave the title compound (0.057 g, 28%) as white solid.
MS m/e: 480 (M+H$^+$).

Example 11 trans-8-Fluoro-1-(4-phenoxy-cyclohexyl)-4H,6H-2,3,5,10b-tetraaza-benzo[e]azulene-5-carboxylic acid tert-butyl ester The title compound was obtained as white solid in 54% yield according to general procedure V. Hydrazide: trans-4-Phenoxy-cyclohexanecarboxylic acid hydrazide
Thiolactam: 7-Fluoro-2-thioxo-1,2,3,5-tetrahydro-benzo[e][1,4]diazepine-4-carboxylic acid tert-butyl ester
MS m/e: 479 (M+H$^+$)

Example 12 trans-8-Fluoro-1-(4-phenoxy-cyclohexyl)-5,6-dihydro-4H-2,3,5,10b-tetraaza-benzo[e]azulene hydrochloride The title compound was obtained as light yellow solid in quantitative yield from trans-8-fluoro-1-(4-phenoxy-cyclohexyl)-4H,6H-2,3,5,10b-tetraaza-benzoazulene-5-carboxylic acid tert-butyl ester according to general procedure VI. MS m/e: 379 (M+H$^+$)

Example 13 trans-8-Fluoro-5-methyl-1-(4-phenoxy-cyclohexyl)-5,6-dihydro-4H-2,3,5,10b-tetraaza-benzoazulene The title compound was obtained as white solid in 63% yield from trans-8-fluoro-1-(4-phenoxy-cyclohexyl)-5,6-dihydro-4H-2,3,5,10b-tetraaza-benzoazulene hydrochloride and paraformaldehyde according to general procedure VII. MS m/e: 393 (M+H$^+$).

Example 14 cis-8-Chloro-1-(4-phenoxy-cyclohexyl)-4H,6H-2,3,5,10b-tetraaza-benzoazulene-5-carboxylic acid tert-butyl ester The title compound was obtained as white solid in 69% yield according to general procedure V. Hydrazide: cis-4-Phenoxy-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester
MS m/e: 495 (M+H$^+$)

Example 15 cis-8-Chloro-1-(4-phenoxy-cyclohexyl)-5,6-dihydro-4H-2,3,5,10b-tetraaza-benzoazulene hydrochloride The title compound was obtained as white solid in quantitative yield from cis-8-chloro-1-(4-phenoxy-cyclohexyl)-

4H,6H-2,3,5,10b-tetraaza-benzoazulene-5-carboxylic acid tert-butyl ester according to general procedure VI. MS m/e: 395 (M+H$^+$)

Example 16 cis-8-Chloro-5-methyl-1-(4-phenoxy-cyclohexyl)-5,6-dihydro-4H-2,3,5,10b-tetraaza-benzoazulene The title compound was obtained as white solid in 73% yield from cis-8-chloro-1-(4-phenoxy-cyclohexyl)-5,6-dihydro-4H-2,3,5,10b-tetraaza-benzoazulene hydrochloride and paraformaldehyde according to general procedure VII. MS m/e: 409 (M+H$^+$)

Example 17 trans-8-Chloro-1-[4-(4-fluoro-phenoxy)-cyclohexyl]-4H,6H-2,3,5,10b-tetraaza-benzoazulene-5-carboxylic acid tert-butyl ester The title compound was obtained as white solid in 66% yield according to general procedure V. Hydrazide: trans-4-(4-Fluoro-phenoxy)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester
MS m/e: 513 (M+H$^+$)

Example 18 trans-8-Chloro-1-[4-(4-fluoro-phenoxy)-cyclohexyl]-5,6-dihydro-4H-2,3,5,10b-tetraaza-benzo[e]azulene hydrochloride The title compound was obtained as white solid in quantitative yield from trans-8-chloro-1-[4-(4-fluoro-phenoxy)-cyclohexyl]-4H,6H-2,3,5,10b-tetraaza-benzoazulene-5-carboxylic acid tert-butyl ester according to general procedure VI. MS m/e: 413 (M+H$^+$)

Example 19 trans-8-Chloro-1-[4-(4-fluoro-phenoxy)-cyclohexyl]-5-methyl-5,6-dihydro-4H-2,3,5,10b-tetraaza-benzoazulene The title compound was obtained as white solid in 70% yield from trans-8-chloro-1-[4-(4-fluoro-phenoxy)-cyclohexyl]-5,6-dihydro-4H-2,3,5,10b-tetraaza-benzo[e]azulene hydrochloride and paraformaldehyde according to general procedure VII. MS m/e: 427 (M+H$^+$)

Example 20 trans-8-Chloro-1-[4-(4-cyano-phenoxy)-cyclohexyl]-4H,6H-2,3,5,10b-tetraaza-benzo[e]azulene-5-carboxylic acid tert-butyl ester The title compound was obtained according to general procedure V.
Hydrazide: trans-4-(4-Cyano-phenoxy)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester.
MS m/e: 520 (M+H$^+$)

Example 21 trans-4-[4-(8-Chloro-5,6-dihydro-4H-2,3,5,10b-tetraaza-benzo[e]azulen-1-yl)-cyclohexyloxy]-benzonitrile hydrochloride The title compound was obtained from trans-8-chloro-1-[4-(4-cyano-phenoxy)-cyclohexyl]-4H,6H-2,3,5,10b-tetraaza-benzo[e]azulene-5-carboxylic acid tert-butyl ester according to general procedure VI. MS m/e: 420 (M+H$^+$)

Example 22 trans-4-[4-(8-Chloro-5-methyl-5,6-dihydro-4H-2,3,5,10b-tetraaza-benzo[e]azulen-1-yl)-cyclohexyloxy]-benzonitrile The title compound was obtained from trans-4-[4-(8-chloro-5,6-dihydro-4H-2,3,5,10b-tetraaza-benzo[e]azulen-1-yl)-cyclohexyloxy]-benzonitrile hydrochloride and paraformaldehyde according to general procedure VII. MS m/e: 434 (M+H$^+$)

Example 23 trans-8-Chloro-1-[4-(4-trifluoromethyl-phenoxy)-cyclohexyl]-4H,6H-2,3,5,10b-tetraaza-benzo[e]azulene-5-carboxylic acid tert-butyl ester The title compound was obtained according to general procedure V.
Hydrazide: trans-4-(4-Trifluoromethyl-phenoxy)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester
MS m/e: 563 (M+H$^+$)

Example 24 trans-8-Chloro-1-[4-(4-trifluoromethyl-phenoxy)-cyclohexyl]-5,6-dihydro-4H-2,3,5,10b-tetraaza-benzo[e]azulene hydrochloride The title compound was obtained from trans-8-chloro-1-[4-(4-trifluoromethyl-phenoxy)-cyclohexyl]-4H,6H-2,3,5,10b-tetraaza-benzo[e]azulene-5-carboxylic acid tert-butyl ester according to general procedure VI. MS m/e: 463 (M+H$^+$)

Example 25 trans-8-Chloro-5-methyl-1-[4-(4-trifluoromethyl-phenoxy)-cyclohexyl]-5,6-dihydro-4H-2,3,5,10b-tetraaza-benzo[e]azulene The title compound was obtained from trans-8-chloro-1-[4-(4-trifluoromethyl-phenoxy)-cyclohexyl]-5,6-dihydro-4H-2,3,5,10b-tetraaza-benzo[e]azulene hydrochloride and paraformaldehyde according to general procedure VII. MS m/e: 477 (M+H$^+$)

Example 26 trans-8-Chloro-1-[4-(3-chloro-phenoxy)-cyclohexyl]-4H,6H-2,3,5,10b-tetraaza-benzoazulene-5-carboxylic acid tert-butyl ester The title compound was obtained as white solid in 74% yield according to general procedure V. Hydrazide: trans-4-

(3-Chloro-phenoxy)-cyclohexanecarboxylic acid hydrazide Thiolactam: 7-Chloro-2-thioxo-1,2,3,5-tetrahydro-benzo[e][1,4]diazepine-4-carboxylic acid tert-butyl ester
MS m/e: 529 (M+H$^+$)

Example 27 trans-8-Chloro-1-[4-(3-chloro-phenoxy)-cyclohexyl]-5,6-dihydro-4H-2,3,5,10b-tetraaza-benzoazulene hydrochloride The title compound was obtained in quantitative yield from trans-8-chloro-1-[4-(3-chloro-phenoxy)-cyclohexyl]-4H,6H-2,3,5,10b-tetraaza-benzoazulene-5-carboxylic acid tert-butyl ester according to general procedure VI. MS m/e: 429 (M+H$^+$)

Example 28 trans-8-Chloro-1-[4-(3-chloro-phenoxy)-cyclohexyl]-5-methyl-5,6-dihydro-4H-2,3,5,10b-tetraaza-benzoazulene The title compound was obtained as colorless oil in 83% yield from trans-8-chloro-1-[4-(3-chloro-phenoxy)-cyclohexyl]-5,6-dihydro-4H-2,3,5,10b-tetraaza-benzo azulene hydrochloride and paraformaldehyde according to general procedure VII. MS m/e: 443 (M+H$^+$)

Example 29 trans-8-Chloro-1-[4-(3-methoxy-phenoxy)-cyclohexyl]-4H,6H-2,3,5,10b-tetraaza-benzoazulene-5-carboxylic acid tert-butyl ester The title compound was obtained as white foam in 75% yield according to general procedure V. Hydrazide: trans-4-(3-Methoxy-phenoxy)-cyclohexanecarboxylic acid hydrazide Thiolactam: 7-Chloro-2-thioxo-1,2,3,5-tetrahydro-benzo[e][1,4]diazepine-4-carboxylic acid tert-butyl ester
MS m/e: 525.5 (M+H$^+$)

Example 30 trans-8-Chloro-1-[4-(3-methoxy-phenoxy)-cyclohexyl]-5,6-dihydro-4H-2,3,5,10b-tetraaza-benzo[e]azulene hydrochloride The title compound was obtained as white solid in quantitative yield from trans-8-chloro-1-[4-(3-methoxy-phenoxy)-cyclohexyl]-4H,6H-2,3,5,10b-tetraaza-benzoazulene-5-carboxylic acid tert-butyl ester according to general procedure VI. MS m/e: 425 (M+H$^+$)

Example 31 trans-8-Chloro-1-[4-(3-methoxy-phenoxy)-cyclohexyl]-5-methyl-5,6-dihydro-4H-2,3,5,10b-tetraaza-benzoazulene The title compound was obtained as white solid in 43% yield from trans-8-chloro-1-[4-(3-methoxy-phenoxy)-cyclohexyl]-5,6-dihydro-4H-2,3,5,10b-tetraaza-benzo[e]azulene hydrochloride and paraformaldehyde according to general procedure VII. MS m/e: 439 (M+H$^+$)

Example 32 trans-8-Chloro-1-[4-(3-cyano-phenoxy)-cyclohexyl]-4H,6H-2,3,5,10b-tetraaza-benzoazulene-5-carboxylic acid tert-butyl ester The title compound was obtained as brown solid in 18% yield with a purity of approximately 80% by LC-MS according to general procedure V. Hydrazide trans-4-(3-Cyano-phenoxy)-cyclohexanecarboxylic acid hydrazide. Thiolactam: 7-Chloro-2-thioxo-1,2,3,5-tetrahydro-benzo[e][1,4]diazepine-4-carboxylic acid tert-butyl ester
MS m/e: 520 (M+H$^+$)

Example 33 trans-3-[4-(8-Chloro-5,6-dihydro-4H-2,3,5,10b-tetraaza-benzoazulen-1-yl)-cyclohexyloxy]-benzonitrile hydrochloride The title compound was obtained as brown solid in 95% yield from trans-8-chloro-1-[4-(3-cyano-phenoxy)-cyclohexyl]-4H,6H-2,3,5,10b-tetraaza-benzoazulene-5-carboxylic acid tert-butyl ester according to general procedure VI. MS m/e: 420 (M+H$^+$)

Example 34 trans-3-[4-(8-Chloro-5-methyl-5,6-dihydro-4H-2,3,5,10b-tetraaza-benzoazulen-1-yl)-cyclohexyloxy]-benzo nitrile The title compound was obtained as yellow solid in 43% yield from trans-3-[4-(8-chloro-5,6-dihydro-4H-2,3,5,10b-tetraaza-benzo azulen-1-yl)-cyclohexyloxy]-benzo nitrile hydrochloride and paraformaldehyde according to general procedure VII. MS m/e: 434 (M+H$^+$)

Example 35 trans-8-Chloro-1-(4-m-tolyloxy-cyclohexyl)-4H,6H-2,3,5,10b-tetraaza-benzo[e]azulene-5-carboxylic acid tert-butyl ester The title compound was obtained according to general procedure V.
Hydrazide: trans-4-m-Tolyloxy-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester
MS m/e: 509 (M+H$^+$)

Example 36 trans-8-Chloro-1-(4-m-tolyloxy-cyclohexyl)-5,6-dihydro-4H-2,3,5,10b-tetraaza-benzo[e]azulene hydrochloride The title compound was obtained trans-8-chloro-1-(4-m-tolyloxy-cyclohexyl)-4H,6H-2,3,5,10b-tetraaza-benzo[e]azulene-5-carboxylic acid tert-butyl ester according to general procedure VI.
MS m/e: 409 (M+H$^+$)

Example 37 trans-8-Chloro-5-methyl-1-(4-m-tolyloxy-cyclohexyl)-5,6-dihydro-4H-2,3,5,10b-tetraaza-benzo[e]azulene The title compound was obtained from trans-8-chloro-1-(4-m-tolyloxy-cyclohexyl)-5,6-dihydro-4H-2,3,5,10b-tetraaza-benzo[e]azulene hydrochloride and paraformaldehyde according to general procedure VII. MS m/e: 423.5 (M+H$^+$)

Example 38 trans-1-[4-(3-tert-Butyl-phenoxy)-cyclohexyl]-8-chloro-4H,6H-2,3,5,10b-tetraaza-benzo[e]azulene-5-carboxylic acid tert-butyl ester The title compound was obtained according to general procedure V.
Hydrazide: trans-4-(3-tert-Butyl-phenoxy)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 551.5 (M+H$^+$)

Example 39 trans-1-[4-(3-tert-Butyl-phenoxy)-cyclohexyl]-8-chloro-5,6-dihydro-4H-2,3,5,10b-tetraaza-benzo[e]azulene hydrochloride The title compound was obtained trans-1-[4-(3-tert-butyl-phenoxy)-cyclohexyl]-8-chloro-4H,6H-2,3,5,10b-tetraaza-benzo[e]azulene-5-carboxylic acid tert-butyl ester according to general procedure VI. MS m/e: 451 (M+H$^+$)

Example 40 trans-1-[4-(3-tert-Butyl-phenoxy)-cyclohexyl]-8-chloro-5-methyl-5,6-dihydro-4H-2,3,5,10b-tetraaza-benzo[e]azulene The title compound was obtained from trans-1-[4-(3-tert-butyl-phenoxy)-cyclohexyl]-8-chloro-5,6-dihydro-4H-2,3,5,10b-tetraaza-benzo[e]azulene hydrochloride and paraformaldehyde according to general procedure VII. MS m/e: 465 (M+H$^+$)

Example 41 trans-8-Chloro-1-[4-(3-trifluoromethyl-phenoxy)-cyclohexyl]-4H,6H-2,3,5,10b-tetraaza-benzo[e]azulene-5-carboxylic acid tert-butyl ester The title compound was obtained according to general procedure V.
Hydrazide: trans-4-(3-Trifluoromethyl-phenoxy)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester
MS m/e: 563 (M+H$^+$)

Example 42 trans-8-Chloro-1-[4-(3-trifluoromethyl-phenoxy)-cyclohexyl]-5,6-dihydro-4H-2,3,5,10b-tetraaza-benzo[e]azulene hydrochloride The title compound was obtained from trans-8-chloro-1-[4-(3-trifluoromethyl-phenoxy)-cyclohexyl]-4H,6H-2,3,5,10b-tetraaza-benzo[e]azulene-5-carboxylic acid tert-butyl ester according to general procedure VI. MS m/e: 463 (M+H$^+$)

Example 43 trans-8-Chloro-1-[4-(2-fluoro-phenoxy)-cyclohexyl]-4H,6H-2,3,5,10b-tetraaza-benzo[e]azulene-5-carboxylic acid tert-butyl ester The title compound was obtained according to general procedure V.
Hydrazide: trans-4-(2-Fluoro-phenoxy)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester
MS m/e: 513 (M+H$^+$)

Example 44 trans-8-Chloro-1-[4-(2-fluoro-phenoxy)-cyclohexyl]-5,6-dihydro-4H-2,3,5,10b-tetraaza-benzo[e]azulene hydrochloride The title compound was obtained from trans-8-chloro-1-[4-(2-fluoro-phenoxy)-cyclohexyl]-4H,6H-2,3,5,10b-tetraaza-benzo[e]azulene-5-carboxylic acid tert-butyl ester according to general procedure VI. MS m/e: 413 (M+H$^+$)

Example 45 trans-8-Chloro-1-[4-(2-fluoro-phenoxy)-cyclohexyl]-5-methyl-5,6-dihydro-4H-2,3,5,10b-tetraaza-benzo[e]azulene The title compound was obtained from trans-8-chloro-1-[4-(2-fluoro-phenoxy)-cyclohexyl]-5,6-dihydro-4H-2,3,5,10b-tetraaza-benzo[e]azulene hydrochloride and paraformaldehyde according to general procedure VII. MS m/e: 427.5 (M+H$^+$)

Example 46 trans-8-Chloro-1-[4-(2-cyano-phenoxy)-cyclohexyl]-4H,6H-2,3,5,10b-tetraaza-benzoazulene-5-carboxylic acid tert-butyl ester The title compound was obtained as white foam in 52% yield according to general procedure V. Hydrazide: trans-4-(2-Cyano-phenoxy)-cyclohexanecarboxylic acid hydrazide Thiolactam: 7-Chloro-2-thioxo-1,2,3,5-tetrahydro-benzo[e][1,4]diazepine-4-carboxylic acid tert-butyl ester
MS m/e: 520 (M+H$^+$)

Example 47 trans-2-[4-(8-Chloro-5,6-dihydro-4H-2,3,5,10b-tetraaza-benzo[e]azulen-1-yl)-cyclohexyloxy]-benzonitrile hydrochloride The title compound was obtained as white solid in 99% yield from trans-8-chloro-1-[4-(2-cyano-phenoxy)-cyclohexyl]-4H,6H-2,3,5,10b-tetraaza-benzoazulene-5-carboxylic acid tert-butyl ester according to general procedure VI. MS m/e: 420 (M+H$^+$)

Example 48 trans-2-[4-(8-Chloro-5-methyl-5,6-dihydro-4H-2,3,5,10b-tetraaza-benzoazulen-1-yl)-cyclohexyloxy]-benzonitrile The title compound was obtained as white solid in 50% yield from trans-2-[4-(8-chloro-5,6-dihydro-4H-2,3,5,10b-tetraaza-benzo[e]azulen-1-yl)-cyclohexyloxy]-benzonitrile hydrochloride and paraformaldehyde according to general procedure VII. MS m/e: 434 (M+H$^+$)

Example 49 trans-8-Chloro-1-(4-o-tolyloxy-cyclohexyl)-4H,6H-2,3,5,10b-tetraaza-benzoazulene-5-carboxylic acid tert-butyl ester The title compound was obtained as yellow solid in 52% yield according to general procedure V. Hydrazide: trans-4-o-Tolyloxy-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester
MS m/e: 509 (M+H$^+$)

Example 50 trans-8-Chloro-1-(4-o-tolyloxy-cyclohexyl)-5,6-dihydro-4H-2,3,5,10b-tetraaza-benzoazulene hydrochloride The title compound was obtained as light yellow solid in quantitative yield from trans-8-chloro-1-(4-o-tolyloxy-cyclohexyl)-4H,6H-2,3,5,10b-tetraaza-benzoazulene-5-carboxylic acid tert-butyl ester according to general procedure VI. MS m/e: 409 (M+H$^+$)

Example 51 trans-8-Chloro-5-methyl-1-(4-o-tolyloxy-cyclohexyl)-5,6-dihydro-4H-2,3,5,10b-tetraaza-benzoazulene The title compound was obtained as light yellow solid in 72% yield from trans-8-chloro-1-(4-o-tolyloxy-cyclohexyl)-5,6-dihydro-4H-2,3,5,10b-tetraaza-benzoazulene hydrochloride and paraformaldehyde according to general procedure VII. MS m/e: 423 (M+H$^+$)

Example 52 trans-8-Chloro-1-[4-(3,5-difluoro-phenoxy)-cyclohexyl]-4H,6H-2,3,5,10b-tetraaza-benzoazulene-5-carboxylic acid tert-butyl ester The title compound was obtained as light yellow solid in 58% yield according to general procedure V. Hydrazide: trans-4-(3,5-Difluoro-phenoxy)-cyclohexanecarboxylic acid hydrazide Thiolactam: 7-Chloro-2-thioxo-1,2,3,5-tetrahydro-benzo[e][1,4]diazepine-4-carboxylic acid tert-butyl ester

Example 53 trans-8-Chloro-1-[4-(3,5-difluoro-phenoxy)-cyclohexyl]-5,6-dihydro-4H-2,3,5,10b-tetraaza-benzoazulene hydrochloride The title compound was obtained as white solid in quantitative yield from trans-8-chloro-1-[4-(3,5-difluoro-phenoxy)-cyclohexyl]-4H,6H-2,3,5,10b-tetraaza-benzoazulene-5-carboxylic acid tert-butyl ester according to general procedure VI. MS m/e: 431 (M+H$^+$)

Example 54 trans-8-Chloro-1-[4-(3,5-difluoro-phenoxy)-cyclohexyl]-5-methyl-5,6-dihydro-4H-2,3,5,10b-tetraaza-benzoazulene The title compound was obtained as white solid in 39% yield from trans-8-chloro-1-[4-(3,5-difluoro-phenoxy)-cyclohexyl]-5,6-dihydro-4H-2,3,5,10b-tetraaza-benzoazulene hydrochloride and paraformaldehyde according to general procedure VII. MS m/e: 445 (M+H$^+$)

Example 55 trans-8-Chloro-1-[4-(naphthalen-2-yloxy)-cyclohexyl]-4H,6H-2,3,5,10b-tetraaza-benzoazulene-5-carboxylic acid tert-butyl ester The title compound was obtained as yellow solid in 78% yield according to general procedure V. Hydrazide: trans-4-(Naphthalen-2-yloxy)-cyclohexanecarboxylic acid hydrazide Thiolactam: 7-Chloro-2-thioxo-1,2,3,5-tetrahydro-benzo[e][1,4]diazepine-4-carboxylic acid tert-butyl ester
MS m/e: 545 (M+H$^+$)

Example 56 trans-8-Chloro-1-[4-(naphthalen-2-yloxy)-cyclohexyl]-5,6-dihydro-4H-2,3,5,10b-tetraaza-benzoazulene hydrochloride The title compound was obtained as white solid in quantitative yield from trans-8-chloro-1-[4-(naphthalen-2-yloxy)-cyclohexyl]-4H,6H-2,3,5,10b-tetraaza-benzoazulene-5-carboxylic acid tert-butyl ester according to general procedure VI. MS m/e: 445 (M+H$^+$)

Example 57 trans-8-Chloro-5-methyl-1-[4-(naphthalen-2-yloxy)-cyclohexyl]-5,6-dihydro-4H-2,3,5,10b-tetraaza-benzoazulene The title compound was obtained as white foam in 60% yield from trans-8-chloro-1-[4-(naphthalen-2-yloxy)-cyclohexyl]-5,6-dihydro-4H-2,3,5,10b-tetraaza-benzoazulene hydrochloride and paraformaldehyde according to general procedure VII. MS m/e: 459 (M+H$^+$)

Example 58 trans-8-Chloro-1-[4-(naphthalen-1-yloxy)-cyclohexyl]-4H,6H-2,3,5,10b-tetraaza-benzoazulene-5-carboxylic acid tert-butyl ester The title compound was obtained as yellow solid in 73% yield according to general procedure V. Hydrazide: trans-4-(Naphthalen-1-yloxy)-cyclohexanecarboxylic acid hydrazide Thiolactam: 7-Chloro-2-thioxo-1,2,3,5-tetrahydro-benzo[e][1,4]diazepine-4-carboxylic acid tert-butyl ester
MS m/e: 545 (M+H$^+$)

Example 59 trans-8-Chloro-1-[4-(naphthalen-1-yloxy)-cyclohexyl]-5,6-dihydro-4H-2,3,5,10b-tetraaza-benzoazulene The title compound was obtained as white solid in 97% yield from trans-8-chloro-1-[4-(naphthalen-1-yloxy)-cyclohexyl]-4H,6H-2,3,5,10b-tetraaza-benzoazulene-5-carboxylic acid tert-butyl ester according to general procedure VI. MS m/e: 445 (M+H$^+$)

Example 60 trans-8-Chloro-5-methyl-1-[4-(naphthalen-1-yloxy)-cyclohexyl]-5,6-dihydro-4H-2,3,5,10b-tetraaza-benzoazulene The title compound was obtained as white foam in 73% yield from trans-8-chloro-1-[4-(naphthalen-1-yloxy)-cyclohexyl]-5,6-dihydro-4H-2,3,5,10b-tetraaza-benzoazulene hydrochloride and paraformaldehyde according to general procedure VII. MS m/e: 459 (M+H$^+$)

Example 61 trans-8-Chloro-1-[4-(pyridin-3-yloxy)-cyclohexyl]-4H,6H-2,3,5,10b-tetraaza-benzoazulene-5-carboxylic acid tert-butyl ester The title compound was obtained as white foam in 51% yield according to general procedure V. Hydrazide: trans-4-(Pyridin-3-yloxy)-cyclohexanecarboxylic acid hydrazide Thiolactam: 7-Chloro-2-thioxo-1,2,3,5-tetrahydro-benzo[e][1,4]diazepine-4-carboxylic acid tert-butyl ester. MS m/e: 496 (M+H$^+$)

Example 62 trans-8-Chloro-1-[4-(pyridin-3-yloxy)-cyclohexyl]-5,6-dihydro-4H-2,3,5,10b-tetraaza-benzo[e]azulene dihydrochloride The title compound was obtained as white solid in quantitative yield from trans-8-chloro-1-[4-(pyridin-3-yloxy)-cyclohexyl]-4H,6H-2,3,5,10b-tetraaza-benzoazulene-5-carboxylic acid tert-butyl ester according to general procedure VI. MS m/e: 396 (M+H$^+$)

Example 63 trans-8-Chloro-5-methyl-1-[4-(pyridin-3-yloxy)-cyclohexyl]-5,6-dihydro-4H-2,3,5,10b-tetraaza-benzoazulene The title compound was obtained as white solid in 41% yield from trans-8-chloro-1-[4-(pyridin-3-yloxy)-cyclohexyl]-5,6-dihydro-4H-2,3,5,10b-tetraaza-benzo[e]azulene dihydrochloride and paraformaldehyde according to general procedure VII. MS m/e: 410 (M+H$^+$)

Example 64 trans-8-Chloro-1-[4-(5-chloro-pyridin-3-yloxy)-cyclohexyl]-4H,6H-2,3,5,10b-tetraaza-benzoazulene-5-carboxylic acid tert-butyl ester The title compound was obtained as white foam in 71% yield according to general procedure V. Hydrazide: trans-4-(5-Chloro-pyridin-3-yloxy)-cyclohexanecarboxylic acid hydrazide. Thiolactam: 7-Chloro-2-thioxo-1,2,3,5-tetrahydro-benzo[e][1,4]diazepine-4-carboxylic acid tert-butyl ester. MS m/e: 530 (M+H$^+$)

Example 65 trans-8-Chloro-1-[4-(5-chloro-pyridin-3-yloxy)-cyclohexyl]-5,6-dihydro-4H-2,3,5,10b-tetraaza-benzoazulene hydrochloride The title compound was obtained as white solid in quantitative yield from trans-8-chloro-1-[4-(5-chloro-pyridin-3-yloxy)-cyclohexyl]-4H,6H-2,3,5,10b-tetraaza-benzoazulene-5-carboxylic acid tert-butyl ester according to general procedure VI. MS m/e: 430 (M+H$^+$)

Example 66 trans-8-Chloro-1-[4-(5-chloro-pyridin-3-yloxy)-cyclohexyl]-5-methyl-5,6-dihydro-4H-2,3,5,10b-tetraaza-benzoazulene The title compound was obtained as white solid in 65% yield from trans-8-chloro-1-[4-(5-chloro-pyridin-3-yloxy)-cyclohexyl]-5,6-dihydro-4H-2,3,5,10b-tetraaza-benzo azulene hydrochloride and paraformaldehyde according to general procedure VI. MS m/e: 444 (M+H$^+$)

Example 67 trans-8-Chloro-1-[4-(pyridin-2-yloxy)-cyclohexyl]-4H,6H-2,3,5,10b-tetraaza-benzoazulene-5-carboxylic acid tert-butyl ester The title compound was obtained as white foam in 77% yield according to general procedure V. Hydrazide: trans-4-(Pyridin-2-yloxy)-cyclohexanecarboxylic acid hydrazide Thiolactam: 7-Chloro-2-thioxo-1,2,3,5-tetrahydro-benzo[e][1,4]diazepine-4-carboxylic acid tert-butyl ester. MS m/e: 496 (M+H$^+$)

Example 68 trans-8-Chloro-1-[4-(pyridin-2-yloxy)-cyclohexyl]-5,6-dihydro-4H-2,3,5,10b-tetraaza-benzoazulene hydrochloride The title compound was obtained as white solid in quantitative yield from trans-8-chloro-1-[4-(pyridin-2-yloxy)-cyclohexyl]-4H,6H-2,3,5,10b-tetraaza-benzoazulene-5-carboxylic acid tert-butyl ester according to general procedure VI. MS m/e: 396 (M+H$^+$)

Example 69 trans-8-Chloro-5-methyl-1-[4-(pyridin-2-yloxy)-cyclohexyl]-5,6-dihydro-4H-2,3,5,10b-tetraaza-benzoazulene The title compound was obtained as white solid in 41% yield from trans-8-chloro-1-[4-(pyridin-2-yloxy)-cyclohexyl]-5,6-dihydro-4H-2,3,5,10b-tetraaza-benzo azulene hydrochloride and paraformaldehyde according to general procedure VII. MS m/e: 410 (M+H$^+$)

Example 70 trans-8-Chloro-1-[4-(6-chloro-pyridin-2-yloxy)-cyclohexyl]-4H,6H-2,3,5,10b-tetraaza-benzo[e]azulene-5-carboxylic acid tert-butyl ester The title compound was obtained according to general procedure V.
Hydrazide: trans-4-(6-Chloro-pyridin-2-yloxy)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 530 (M+H$^+$)

Example 71 trans-8-Chloro-1-[4-(6-chloro-pyridin-2-yloxy)-cyclohexyl]-5,6-dihydro-4H-2,3,5,10b-tetraaza-benzo[e]azulene hydrochloride The title compound was from trans-8-chloro-1-[4-(6-chloro-pyridin-2-yloxy)-cyclohexyl]-4H,6H-2,3,5,10b-tetraaza-benzo[e]azulene-5-carboxylic acid tert-butyl ester according to general procedure VI. MS m/e: 430 (M+H$^+$)

Example 72 trans-8-Chloro-1-[4-(6-chloro-pyridin-2-yloxy)-cyclohexyl]-5-methyl-5,6-dihydro-4H-2,3,5,10b-tetraaza-benzo[e]azulene The title compound was obtained from trans-8-chloro-1-[4-(6-chloro-pyridin-2-yloxy)-cyclohexyl]-5,6-dihydro-4H-2,3,5,10b-tetraaza-benzo[e]azulene hydrochloride and paraformaldehyde according to general procedure VII. MS m/e: 444 (M+H$^+$)

Example 73 trans-8-Chloro-1-[4-(5-chloro-pyridin-2-yloxy)-cyclohexyl]-4H,6H-2,3,5,10b-tetraaza-benzo[e]azulene-5-carboxylic acid tert-butyl ester The title compound was obtained according to general procedure V.
Hydrazide: trans-4-(5-Chloro-pyridin-2-yloxy)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester MS m/e: 530 (M+H$^+$)

Example 74 trans-8-Chloro-1-[4-(5-chloro-pyridin-2-yloxy)-cyclohexyl]-5,6-dihydro-4H-2,3,5,10b-tetraaza-benzo[e]azulene hydrochloride The title compound was obtained from trans-8-chloro-1-[4-(5-chloro-pyridin-2-yloxy)-cyclohexyl]-4H,6H-2,3,5,10b-tetraaza-benzo[e]azulene-5-carboxylic acid tert-butyl ester according to general procedure VI. MS m/e: 430 (M+H$^+$)

Example 75 trans-8-Chloro-1-[4-(5-chloro-pyridin-2-yloxy)-cyclohexyl]-5-methyl-5,6-dihydro-4H-2,3,5,10b-tetraaza-benzo[e]azulene The title compound was obtained from trans-8-chloro-1-[4-(5-chloro-pyridin-2-yloxy)-cyclohexyl]-5,6-dihydro-4H-2,3,5,10b-tetraaza-benzo[e]azulene hydrochloride and paraformaldehyde according to general procedure VII. MS m/e: 444 (M+H$^+$)

Example 76 trans-8-Chloro-1-[4-(2,6-dimethyl-pyrimidin-4-yloxy)-cyclohexyl]-4H,6H-2,3,5,10b-tetraaza-benzoazulene-5-carboxylic acid tert-butyl ester The title compound was obtained as white foam in 64% yield according to general procedure V. Hydrazide: trans-4-(2,6-Dimethyl-pyrimidin-4-yloxy)-cyclohexanecarboxylic acid hydrazide. Thiolactam: 7-Chloro-2-thioxo-1,2,3,5-tetrahydro-benzo[e][1,4]diazepine-4-carboxylic acid tert-butyl ester MS m/e: 525.5 MS (M+H$^+$)

Example 77 trans-8-Chloro-1-[4-(2,6-dimethyl-pyrimidin-4-yloxy)-cyclohexyl]-5,6-dihydro-4H-2,3,5,10b-tetraaza-benzoazulene hydrochloride The title compound was obtained as white solid in quantitative yield from trans-8-chloro-1-[4-(2,6-dimethyl-pyrimidin-4-yloxy)-cyclohexyl]-4H,6H-2,3,5,10b-tetraaza-benzoazulene-5-carboxylic acid tert-butyl ester according to general procedure VI. MS m/e: 425 (M+H$^+$)

Example 78 trans-8-Chloro-1-[4-(2,6-dimethyl-pyrimidin-4-yloxy)-cyclohexyl]-5-methyl-5,6-dihydro-4H-2,3,5,10b-tetraaza-benzoazulene The title compound was obtained as white solid in 15% yield from trans-8-chloro-1-[4-(2,6-dimethyl-pyrimidin-4-yloxy)-cyclohexyl]-5,6-dihydro-4H-2,3,5,10b-tetraaza-benzoazulene hydrochloride and paraformaldehyde according to general procedure VII. MS m/e: 439 (M+H$^+$)

Example 79 trans-8-Chloro-1-[4-(pyrimidin-2-yloxy)-cyclohexyl]-4H,6H-2,3,5,10b-tetraaza-benzo[e]azulene-5-carboxylic acid tert-butyl ester and

Example 80 cis-8-Chloro-1-[4-(pyrimidin-2-yloxy)-cyclohexyl]-4H,6H-2,3,5,10b-tetraaza-benzo[e]azulene-5-carboxylic acid tert-butyl ester trans-8-Chloro-1-[4-(pyrimidin-2-yloxy)-cyclohexyl]-4H,6H-2,3,5,10b-tetraaza-benzo[e]azulene-5-carboxylic acid tert-butyl ester and cis-8-chloro-1-[4-(pyrimidin-2-yloxy)-cyclohexyl]-4H,6H-2,3,5,10b-tetraaza-benzo[e]azulene-5-carboxylic acid tert-butyl ester were obtained after separation by flash-column chromatography according to general procedure V. Hydrazide: cis/trans-4-(Pyrimidin-2-yloxy)-cyclohexanecarboxylic acid hydrazide (1:2) Thiolactam: 7-Chloro-2-thioxo-1,2,3,5-tetrahydro-benzo[e][1,4]diazepine-4-carboxylic acid tert-butyl ester trans-8-Chloro-1-[4-(pyrimidin-2-yloxy)-cyclohexyl]-4H,6H-2,3,5,10b-tetraaza-benzo[e]azulene-5-carboxylic acid tert-butyl ester was obtained as off-white solid in 38% yield.

MS m/e: 497 (M+H$^+$)

cis-8-Chloro-1-[4-(pyrimidin-2-yloxy)-cyclohexyl]-4H,6H-2,3,5,10b-tetraaza-benzo[e]azulene-5-carboxylic acid tert-butyl ester was obtained as off-white solid in 8% yield.

MS m/e: 497 (M+H$^+$)

Example 81 trans-8-Chloro-1-[4-(pyrimidin-2-yloxy)-cyclohexyl]-5,6-dihydro-4H-2,3,5,10b-tetraaza-benzo[e]azulene The title compound was obtained as yellow solid in 73% yield from trans-8-chloro-1-[4-(pyrimidin-2-yloxy)-cyclohexyl]-4H,6H-2,3,5,10b-tetraaza-benzo[e]azulene-5-carboxyli c acid tert-butyl ester according to general procedure VI. MS m/e: 397 (M+H$^+$)

Example 82 trans-8-Chloro-5-methyl-1-[4-(pyrimidin-2-yloxy)-cyclohexyl]-5,6-dihydro-4H-2,3,5,10b-tetraaza-benzo[e]azulene The title compound was obtained as white solid in 34% yield from trans-8-chloro-1-[4-(pyrimidin-2-yloxy)-cyclohexyl]-5,6-dihydro-4H-2,3,5,10b-tetraaza-benzo[e]azulene and paraformaldehyde according to general procedure VII. MS m/e: 411 (M+H$^+$)

Example 83 trans-8-Chloro-1-[4-(pyrazin-2-yloxy)-cyclohexyl]-4H,6H-2,3,5,10b-tetraaza-benzo[e]azulene-5-carboxylic acid tert-butyl ester The title compound was obtained as white solid in 70% yield according to general procedure V. Hydrazide: trans-4-(Pyrazin-2-yloxy)-cyclohexanecarboxylic acid hydrazide Thiolactam: 7-Chloro-2-thioxo-1,2,3,5-tetrahydro-benzo[e][1,4]diazepine-4-carboxylic acid tert-butyl ester MS m/e: 497 (M+H$^+$)

Example 84 trans-8-Chloro-1-[4-(pyrazin-2-yloxy)-cyclohexyl]-5,6-dihydro-4H-2,3,5,10b-tetraaza-benzo[e]azulene The title compound was obtained as yellow solid in 84% yield from trans-8-chloro-1-[4-(pyrazin-2-yloxy)-cyclohexyl]-4H,6H-2,3,5,10b-tetraaza-benzo[e]azulene-5-carboxylic acid tert-butyl ester according to general procedure VI. MS m/e: 397 (M+H$^+$)

Example 85 trans-8-Chloro-5-methyl-1-[4-(pyrazin-2-yloxy)-cyclohexyl]-5,6-dihydro-4H-2,3,5,10b-tetraaza-benzo[e]azulene The title compound was obtained as white solid in 45% yield from trans 8-chloro-1-[4-(pyrazin-2-yloxy)-cyclohexyl]-5,6-dihydro-4H-2,3,5,10b-tetraaza-benzo[e]azulene and paraformaldehyde according to general procedure VII. MS m/e: 411 (M+H$^+$)

Example 86 trans-8-Chloro-1-[4-(pyrimidin-4-yloxy)-cyclohexyl]-4H,6H-2,3,5,10b-tetraaza-benzo[e]azulene-5-carboxylic acid tert-butyl ester and Example 87 cis-8-Chloro-1-[4-(pyrimidin-4-yloxy)-cyclohexyl]-4H,6H-2,3,5,10b-tetraaza-benzo[e]azulene-5-carboxylic acid tert-butyl ester trans-8-Chloro-1-[4-(pyrimidin-4-yloxy)-cyclohexyl]-4H,6H-2,3,5,10b-tetraaza-benzo[e]azulene-5-carboxylic acid tert-butyl ester and cis-8-chloro-1-[4-(pyrimidin-4-yloxy)-cyclohexyl]-4H,6H-2,3,5,10b-tetraaza-benzo[e]azulene-5-carboxylic acid tert-butyl ester were obtained after separation by flash-column chromatography according to general procedure V. Hydrazide: cis/trans-4-(Pyrimidin-4-yloxy)-cyclohexanecarboxylic acid hydrazide (1:1) Thiolactam: 7-Chloro-2-thioxo-1,2,3,5-tetrahydro-benzo[e][1,4]diazepine-4-carboxylic acid tert-butyl ester trans-8-Chloro-1-[4-(pyrimidin-4-yloxy)-cyclohexyl]-4H,6H-2,3,5,10b-tetraaza-benzo[e]azulene-5-carboxylic acid tert-butyl ester was obtained as white solid in 24% yield.

MS m/e: 497 (M+H$^+$)

cis-8-Chloro-1-[4-(pyrimidin-4-yloxy)-cyclohexyl]-4H,6H-2,3,5,10b-tetraaza-benzo[e]azulene-5-carboxylic acid tert-butyl ester was obtained as white solid in 23% yield according to general procedure V.

MS m/e: 497 (M+H$^+$)

Example 88 trans-8-Chloro-1-[4-(pyrimidin-4-yloxy)-cyclohexyl]-5,6-dihydro-4H-2,3,5,10b-tetraaza-benzo[e]azulene hydrochloride The title compound was obtained as off-white solid in quantitative yield from trans-8-chloro-1-[4-(pyrimidin-4-yloxy)-cyclohexyl]-4H,6H-2,3,5,10b-tetraaza-benzo[e]azulene-5-carboxylic acid tert-butyl ester according to general procedure VI. MS m/e: 397 (M+H$^+$)

Example 89 trans-8-Chloro-5-methyl-1-[4-(pyrimidin-4-yloxy)-cyclohexyl]-5,6-dihydro-4H-2,3,5,10b-tetraaza-benzo[e]azulene The title compound was obtained as white solid in 29% yield from trans-8-chloro-1-[4-(pyrimidin-4-yloxy)-cyclohexyl]-5,6-dihydro-4H-2,3,5,10b-tetraaza-benzo[e]azulene hydrochloride and paraformaldehyde according to general procedure VII. MS m/e: 411 (M+H$^+$)

Example 90 cis-8-Chloro-1-[4-(pyrimidin-4-yloxy)-cyclohexyl]-5,6-dihydro-4H-2,3,5,10b-tetraaza-benzo[e]azulene hydrochloride The title compound was obtained as white solid in quantitative yield from cis-8-chloro-1-[4-(pyrimidin-4-yloxy)-cyclohexyl]-4H,6H-2,3,5,10b-tetraaza-benzo[e]azulene-5-carboxylic acid tert-butyl ester according to general procedure VI. MS m/e: 397 (M+H$^+$)

Example 91 cis-8-Chloro-5-methyl-1-[4-(pyrimidin-4-yloxy)-cyclohexyl]-5,6-dihydro-4H-2,3,5,10b-tetraaza-benzo[e]azulene The title compound was obtained as white solid in 28% yield from cis-8-chloro-1-[4-(pyrimidin-4-yloxy)-cyclohexyl]-5,6-dihydro-4H-2,3,5,10b-tetraaza-benzo[e]azulene hydrochloride and paraformaldehyde according to general procedure VII. MS m/e: 411 (M+H$^+$)

Example 92 trans-8-Chloro-1-[4-(pyridazin-3-yloxy)-cyclohexyl]-4H,6H-2,3,5,10b-tetraaza-benzo[e]azulene-5-carboxylic acid tert-butyl ester and

Example 93 cis-8-Chloro-1-[4-(pyridazin-3-yloxy)-cyclohexyl]-4H,6H-2,3,5,10b-tetraaza-benzo[e]azulene-5-carboxylic acid tert-butyl ester trans-8-Chloro-1-[4-(pyridazin-3-yloxy)-cyclohexyl]-4H,6H-2,3,5,10b-tetraaza-benzo[e]azulene-5-carboxylic acid tert-butyl ester and cis-8-chloro-1-[4-(pyridazin-3-yloxy)-cyclohexyl]-4H,6H-2,3,5,10b-tetraaza-benzo[e]azulene-5-carboxylic acid tert-butyl ester were obtained after separation by flash-column chromatography according to general procedure V. Hydrazide: cis/trans-4-(Pyridazin-3-yloxy)-cyclohexanecarboxylic acid hydrazide (1:1) Thiolactam: 7-Chloro-2-thioxo-1,2,3,5-tetrahydro-benzo[e][1,4]diazepine-4-carboxylic acid tert-butyl ester trans-8-Chloro-1-[4-(pyridazin-3-yloxy)-cyclohexyl]-4H,6H-2,3,5,10b-tetraaza-benzo[e]azulene-5-carboxylic acid tert-butyl ester was obtained as white solid in 19% yield.
MS m/e: 497 (M+H$^+$)
cis-8-Chloro-1-[4-(pyridazin-3-yloxy)-cyclohexyl]-4H,6H-2,3,5,10b-tetraaza-benzo[e]azulene-5-carboxylic acid tert-butyl ester was obtained as white solid in 23% yield.
MS m/e: 497 (M+H$^+$)

Example 94 trans-8-Chloro-1-[4-(pyridazin-3-yloxy)-cyclohexyl]-5,6-dihydro-4H-2,3,5,10b-tetraaza-benzo[e]azulene hydrochloride The title compound was obtained as off-white solid in quantitative yield from trans-8-chloro-1-[4-(pyridazin-3-yloxy)-cyclohexyl]-4H,6H-2,3,5,10b-tetraaza-benzo[e]azulene-5-carboxylic acid tert-butyl ester according to general procedure VI. MS m/e: 397 (M+H$^+$)

Example 95 trans-8-Chloro-5-methyl-1-[4-(pyridazin-3-yloxy)-cyclohexyl]-5,6-dihydro-4H-2,3,5,10b-tetraaza-benzo[e]azulene The title compound was obtained as white solid in 11% yield from trans-8-chloro-1-[4-(pyridazin-3-yloxy)-cyclohexyl]-5,6-dihydro-4H-2,3,5,10b-tetraaza-benzo[e]azulene hydrochloride and paraformaldehyde according to general procedure VII. MS m/e: 411 (M+H$^+$)

Example 96 cis-8-Chloro-1-[4-(pyridazin-3-yloxy)-cyclohexyl]-5,6-dihydro-4H-2,3,5,10b-tetraaza-benzo[e]azulene hydrochloride The title compound was obtained as off-white solid in quantitative yield from cis-8-chloro-1-[4-(pyridazin-3-yloxy)-cyclohexyl]-4H,6H-2,3,5,10b-tetraaza-benzo[e]azulene-5-carboxylic acid tert-butyl ester according to general procedure VI. MS m/e: 397 (M+H$^+$)

Example 97 cis-8-Chloro-5-methyl-1-[4-(pyridazin-3-yloxy)-cyclohexyl]-5,6-dihydro-4H-2,3,5,10b-tetraaza-benzo[e]azulene The title compound was obtained as white solid in 3% yield from cis-8-chloro-1-[4-(pyridazin-3-yloxy)-cyclohexyl]-5,6-dihydro-4H-2,3,5,10b-tetraaza-benzo[e]azulene hydrochloride and paraformaldehyde according to general procedure VII. MS m/e: 411 (M+H$^+$)

Example 98 trans-8-Chloro-1-[4-(3-fluoro-pyridin-2-yloxy)-cyclohexyl]-5,6-dihydro-4H-2,3,5,10b-tetraaza-benzo[e]azulene The title compound was obtained as white solid in 78% yield over two steps according to general procedure V followed by treatment of the crude product under the conditions of general procedure VI. Hydrazide: trans-4-(3-Fluoro-pyridin-2-yloxy)-cyclohexanecarboxylic acid hydrazide. Thiolactam: 7-Chloro-2-thioxo-1,2,3,5-tetrahydro-benzo[e][1,4]diazepine-4-carboxylic acid tert-butyl ester
MS m/e: 414 (M+H$^+$)

Example 99 trans-8-Chloro-1-[4-(3-fluoro-pyridin-2-yloxy)-cyclohexyl]-5-methyl-5,6-dihydro-4H-2,3,5,10b-tetraaza-benzo[e]azulene The title compound was obtained as white solid in 69% yield from trans-8-chloro-1-[4-(3-fluoro-pyridin-2-yloxy)-cyclohexyl]-5,6-dihydro-4H-2,3,5,10b-tetraaza-benzo[e]azulene and paraformaldehyde according to general procedure VII. MS m/e: 428 (M+H$^+$)

Example 100 trans-8-Chloro-5-ethyl-1-[4-(3-fluoro-pyridin-2-yloxy)-cyclohexyl]-5,6-dihydro-4H-2,3,5,10b-tetraaza-benzo[e]azulene The title compound was obtained as white solid in 36% yield from trans-8-chloro-1-[4-(3-fluoro-pyridin-2-yloxy)-cyclohexyl]-5,6-dihydro-4H-2,3,5,10b-tetraaza-benzo[e]azulene and acetaldehyde according to general procedure VII. MS m/e: 442 (M+H$^+$)

Example 101 trans-8-Chloro-1-[4-(5-fluoro-pyridin-2-yloxy)-cyclohexyl]-5,6-dihydro-4H-2,3,5,10b-tetraaza-benzo[e]azulene The title compound was obtained as white solid in 73% yield over two steps according to general procedure V followed by treatment of the crude product under the conditions of general procedure VI. Hydrazide: trans-4-(5-Fluoro-pyridin-2-yloxy)-cyclohexanecarboxylic acid hydrazide. Thiolactam: 7-Chloro-2-thioxo-1,2,3,5-tetrahydro-benzo[e][1,4]diazepine-4-carboxylic acid tert-butyl ester
MS m/e: 414 (M+H$^+$)

Example 102 trans-8-Chloro-1-[4-(5-fluoro-pyridin-2-yloxy)-cyclohexyl]-5-methyl-5,6-dihydro-4H-2,3,5,10b-tetraaza-benzo[e]azulene The title compound was obtained as white solid in 61% yield from trans-8-chloro-1-[4-(5-fluoro-pyridin-2-yloxy)-cyclohexyl]-5,6-dihydro-4H-2,3,5,10b-tetraaza-benzo[e]azulene and paraformaldehyde according to general procedure VII. MS m/e: 428 (M+H$^+$)

Example 103 trans-8-Chloro-5-ethyl-1-[4-(5-fluoro-pyridin-2-yloxy)-cyclohexyl]-5,6-dihydro-4H-2,3,5,10b-tetraaza-benzo[e]azulene The title compound was obtained as colorless waxy solid in 76% yield from trans-8-chloro-1-[4-(5-fluoro-pyridin-2-yloxy)-cyclohexyl]-5,6-dihydro-4H-2,3,5,10b-tetraaza-benzo[e]azulene and acetaldehyde according to general procedure VII. MS m/e: 442 (M+H$^+$)

Example 104 trans-8-Chloro-5-(2-fluoro-ethyl)-1-[4-(5-fluoro-pyridin-2-yloxy)-cyclohexyl]-5,6-dihydro-4H-2,3,5,10b-tetraaza-benzo[e]azulene A mixture of trans-8-chloro-1-[4-(5-fluoro-pyridin-2-yloxy)-cyclohexyl]-5,6-dihydro-4H-2,3,5,10b-tetraaza-benzo[e]azulene (0.10 g, 0.24 mmol) and potassium carbonate (67 mg, 0.48 mmol) in acetonitrile (1.2 ml) was treated with 1-bromo-2-fluoroethane (37 mg, 0.29 mmol) at 0° C. The cooling bath was removed and the reaction mixture was heated at 70° C. over night. The mixture was filtered and concentrated in vacuo. Purification by flash column chromatography gave the title compound (17 mg, 15%) as white solid. MS m/e: 460 (M+H$^+$)

Example 105 trans-8-Chloro-1-[4-(6-methyl-pyridin-2-yloxy)-cyclohexyl]-5,6-dihydro-4H-2,3,5,10b-tetraaza-benzo[e]azulene The title compound was obtained as white solid in 72% yield over two steps according to general procedure V followed by treatment of the crude product under the conditions of general procedure VI.
Hydrazide: trans-4-(6-Methyl-pyridin-2-yloxy)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 410 (M+H$^+$)

Example 106 trans-8-Chloro-5-methyl-1-[4-(6-methyl-pyridin-2-yloxy)-cyclohexyl]-5,6-dihydro-4H-2,3,5,10b-tetraaza-benzo[e]azulene The title compound was obtained as white solid in 54% yield from trans-8-chloro-1-[4-(6-methyl-pyridin-2-yloxy)-cyclohexyl]-5,6-dihydro-4H-2,3,5,10b-tetraaza-benzo[e]azulene and paraformaldehyde according to general procedure VII. MS m/e: 424 (M+H$^+$)

Example 107 trans-8-Chloro-5-ethyl-1-[4-(6-methyl-pyridin-2-yloxy)-cyclohexyl]-5,6-dihydro-4H-2,3,5,10b-tetraaza-benzo[e]azulene The title compound was obtained as colorless waxy solid in 62% yield from trans-8-chloro-1-[4-(5-fluoro-pyridin-2-yloxy)-cyclohexyl]-5,6-dihydro-4H-2,3,5,10b-tetraaza-benzo[e]azulene and acetaldehyde according to general procedure VII. MS m/e: 438 (M+H$^+$)

Example 108 trans-8-Chloro-5-(2,2-difluoro-ethyl)-1-[4-(6-methyl-pyridin-2-yloxy)-cyclohexyl]-5,6-dihydro-4H-2,3,5,10b-tetraaza-benzo[e]azulene A mixture of trans-8-chloro-1-[4-(6-methyl-pyridin-2-yloxy)-cyclohexyl]-5,6-dihydro-4H-2,3,5,10b-tetraaza-benzo[e]azulene (0.10 g, 0.24 mmol) and N,N-diisopropyl-ethylamine (0.080 ml, 0.49 mmol) in dichloromethan (1 ml) was treated with trifluoro-methanesulfonic acid 2,2-difluoro-ethyl ester (63 mg, 0.29 mmol) at 0° C. The cooling bath was removed after 30 min. and the reaction mixture was stirred at room temperature over night. The mixture was partitioned between aqueous saturated ammonium chloride solution (50 ml) and ethyl acetate (50 ml). The aqueous layer was extracted with one 50-ml portion of ethyl acetate. The combined organic layers were washed with two 50-ml portions of a 1 M aqueous solution of sodium carbonate. The aqueous layers were each extracted with one 50-ml portion of ethyl acetate. The organic layers were dried over anhydrous sodium sulfate and concenrated in vacuo. Purification by flash column chromatography gave the title compound (98 mg, 85%) as white solid.
MS m/e: 474 (M+H$^+$)

Example 109 cis-8-Chloro-1-[4-(pyridin-2-yloxy)-cyclohexyl]-4H,6H-2,3,5,10b-tetraaza-benzo[e]azulene-5-carboxylic acid tert-butyl ester The title compound was obtained as light yellow solid in 79% yield according to general procedure V.
Hydrazide: cis-4-(Pyridin-2-yloxy)-cyclohexanecarboxylic acid hydrazide Thiolactam: 7-Chloro-2-thioxo-1,2,3,5-tetrahydro-benzo[e][1,4]diazepine-4-carboxylic acid tert-butyl ester. MS m/e: 496 (M+H$^+$)

Example 110 cis-8-Chloro-1-[4-(pyridin-2-yloxy)-cyclohexyl]-5,6-dihydro-4H-2,3,5,10b-tetraaza-benzo[e]azulene The title compound was obtained as light yellow solid in 81% yield from cis-8-chloro-1-[4-(pyridin-2-yloxy)-cyclohexyl]-4H,6H-2,3,5,10b-tetraaza-benzo[e]azulene-5-carboxylic acid tert-butyl ester hydrochloride and paraformaldehyde according to general procedure VI.

MS m/e: 396 (M+H$^+$)

Example 111 cis-8-Chloro-5-methyl-1-[4-(pyridin-2-yloxy)-cyclohexyl]-5,6-dihydro-4H-2,3,5,10b-tetraaza-benzo[e]azulene The title compound was obtained as white solid in 51% yield from cis-8-chloro-1-[4-(pyridin-2-yloxy)-cyclohexyl]-5,6-dihydro-4H-2,3,5,10b-tetraaza-benzo[e]azulene and paraformaldehyde according to general procedure VII. MS m/e: 410 (M+H$^+$)

The invention claimed is:

1. A method for the treatment of a disorder selected from the group consisting of dysmenorrhea, male or female sexual dysfunction, hypertension, chronic heart failure, inappropriate secretion of vasopressin, liver cirrhosis, nephotic syndrome, anxiety, depressive disorders, obsessive compulsive disorder, autistic spectrum disorders, schizophrenia, and aggressive behavior comprising administering a therapeutically effective amount of a compound of formula I

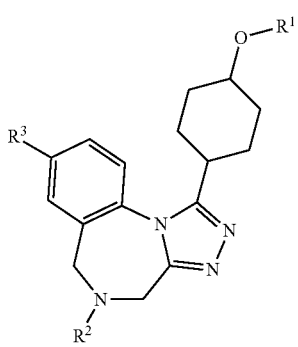

wherein
R$^1$ is aryl or heteroaryl, each of which is unsubstituted or substituted with one or more substituents independently selected from A,
R$^2$ is H,
C$_{1-12}$-alkyl, unsubstituted or substituted with one or more OH, halo, cyano or C$_{1-12}$-alkoxy,
—(CH$_2$)$_q$—R$^a$, wherein R$^a$ is phenyl or 5- or 6-membered heteroaryl, each of which is unsubstituted or substituted with one or more substituents independently selected from A,
—(CH$_2$)$_r$NR$^i$R$^{ii}$,
—C(O)—C$_{1-12}$-alkyl, wherein C$_{1-12}$-alkyl is unsubstituted or substituted with one or more OH, halo, cyano or C$_{1-12}$-alkoxy,
—C(O)(CH$_2$)$_q$OC(O)—C$_{1-12}$-alkyl,
—C(O)(CH$_2$)$_q$NR$^i$R$^{ii}$,
—C(O)O—C$_{1-12}$-alkyl, wherein alkyl is unsubstituted or substituted with one or more OH, halo, cyano or C$_{1-12}$-alkoxy,
—S(O)$_2$—C$_{1-12}$-alkyl, or
—S(O)$_2$NR$^i$R$^{ii}$,
R$^i$ and R$^{ii}$ are each independently H, C$_{1-12}$-alkyl, or together with the nitrogen to which they are bound form a 3- to 7-membered heterocycloalkyl containing one or two heteroatoms selected from N, O and S, which heterocycloalkyl is unsubstituted or substituted by one or more substituents independently selected from B,
q is 1, 2, 3 or 4,
r is 2, 3 or 4,
A is halo, cyano, OH, C$_{1-7}$-alkyl, halo-C$_{1-7}$alkyl, C$_{1-7}$-alkoxy, halo-C$_{1-7}$-alkoxy, or hydroxy-C$_{1-7}$-alkyl,
B is oxo, halo, OH, C$_{1-7}$-alkyl or C$_{1-7}$-alkoxy, and
R$^3$ is Cl or F,
or a pharmaceutically acceptable salt thereof.

2. A method for the treatment of a disorder selected from the group consisting of dysmenorrhea, male or female sexual dysfunction, hypertension, chronic heart failure, inappropriate secretion of vasopressin, liver cirrhosis, nephotic syndrome, anxiety, depressive disorders, obsessive compulsive disorder, autistic spectrum disorders, schizophrenia, and aggressive behavior comprising administering a therapeutically effective amount of a compound of formula I

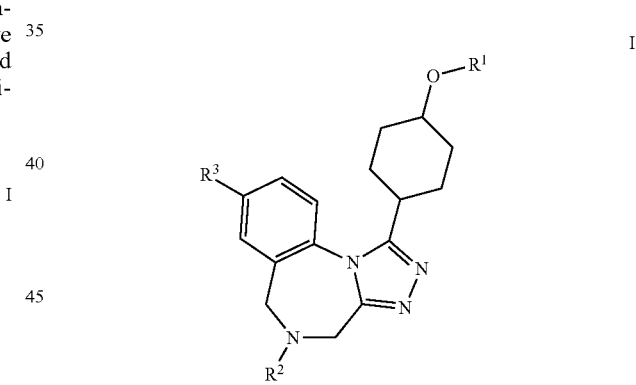

wherein
R$^1$ is a monovalent cyclic aromatic hydrocarbon moiety consisting of a mono- or bicyclic aromatic ring,
a monovalent 5- or 6-membered aromatic monocyclic or 9- or 10-membered aromatic bicyclic ring containing from one to four ring heteroatoms selected from N, O, or S, the remaining ring atoms being C,
each unsubstituted or substituted with one or more substituents independently selected from A;
R$^2$ is H,
C$_{1-12}$-alkyl, unsubstituted or substituted with one or more OH, halo, cyano or C$_{1-12}$-alkoxy,
—(CH$_2$)$_q$—R$^a$, wherein R$^a$ is phenyl or 5- or 6-membered heteroaryl, each of which is unsubstituted or substituted with one or more substituents independently selected from A,
—(CH$_2$)$_r$NR$^i$R$^{ii}$, —C(O)—C$_{1-12}$-alkyl, wherein C$_{1-12}$-alkyl is unsubstituted or substituted with one or more OH, halo, cyano or C$_{1-12}$-alkoxy, —C(O)(CH$_2$)$_q$OC(O)—C$_{1-12}$-alkyl, —C(O)(CH$_2$)$_q$NR$^i$R$^{ii}$, —C(O)O—C$_{1-12}$-alkyl, wherein alkyl is unsubstituted or substituted with one or more OH, halo, cyano or C$_{1-12}$-alkoxy, —S(O)$_2$—C$_{1-12}$-alkyl, or —S(O)$_2$NR$^i$R$^{ii}$, R$^i$ and R$^{ii}$ are each independently H, C$_{1-12}$-alkyl, or together with the nitrogen to which they are bound form a 3- to 7-membered heterocycloalkyl containing one or two heteroatoms selected from N, O and S, which heterocycloalkyl is unsubstituted or substituted by one or more substituents independently selected from B, q is 1, 2, 3 or 4, r is 2, 3 or 4, A is halo, cyano, OH, C$_{1-7}$-alkyl, C$_{1-7}$-alkoxy, halo-C$_{1-7}$-alkoxy, or hydroxy-C$_{1-7}$-alkyl;

B is oxo, halo, OH, C$_{1-7}$-alkyl or C$_{1-7}$-alkoxy, and

R$^3$ is Cl or F, or a pharmaceutically acceptable salt thereof.

3. The method of claim 2, wherein R$^1$ is a monovalent cyclic aromatic hydrocarbon moiety consisting of a monoaromatic ring.

4. The method of claim 1, wherein R$^1$ is naphthyl, phenyl, pyrazinyl, pyridazinyl, pyridinyl or pyrimidinyl.

5. The method of claim 1, wherein R$^1$ is phenyl, 4-fluoro-phenyl, 4-cyanophenyl, 4-trifluoromethyl-phenyl, 3-chloro-phenyl, 3-methoxy-phenyl, 3-cyano-phenyl, 3-methyl-phenyl, 3-t-butyl-phenyl, 3-trifluoromethyl-phenyl, 2-fluoro-phenyl, 2-cyano-phenyl, 2-methyl-phenyl, 3,5-di-fluoro-phenyl, naphth-2-yl, naphth-1-yl, pyridin-3-yl, 5-chloro-pyridin-3-yl, pyridin-2-yl, 6-chloro-pyridin-2-yl, 3-fluoro-pyridin-2-yl, 5-fluoro-pyridin-2-yl, 6-methyl-pyridin-2-yl, 2,6-di-methyl-pyrimidin-4-yl, pyrimidin-2-yl, pyrazin-2-yl, pyridin-4-yl or pyridazin-3-yl.

6. The method of claim 4, wherein R$^1$ is phenyl or pyridinyl.

7. The method of claim 1, wherein

R$^2$ is H,

C$_{1-12}$-alkyl, unsubstituted or substituted with one or more OH or F,

—(CH$_2$)$_q$—R$^a$, wherein R$^a$ is phenyl or 5- or 6-membered heteroaryl and q is 1, 2, 3 or 4, —C(O)—C$_{1-12}$-alkyl, —C(O)(CH$_2$)$_q$NR$^i$R$^{ii}$, wherein R$^i$ and R$^{ii}$ are each independently H or C$_{1-12}$-alkyl, —C(O)O—C$_{1-12}$-alkyl, —S(O)$_2$—C$_{1-12}$-alkyl, or —S(O)$_2$NR$^i$R$^{ii}$, wherein R$^i$ and R$^{ii}$ are each independently H or C$_{1-12}$-alkyl.

8. The method of claim 7, wherein

R$^2$ is H,

C$_{1-12}$-alkyl, unsubstituted or substituted with one or more OH,

—(CH$_2$)$_q$—R$^a$, wherein R$^a$ is phenyl or 5- or 6-membered heteroaryl and q is 1, 2, 3 or 4, —C(O)—C$_{1-12}$-alkyl, —C(O)(CH$_2$)$_q$NR$^i$R$^{ii}$, wherein R$^i$ and R$^{ii}$ are each independently H or C$_{1-12}$-alkyl, —C(O)O—C$_{1-12}$-alkyl, —S(O)$_2$—C$_{1-12}$-alkyl, or —S(O)$_2$NR$^i$R$^{ii}$, wherein R$^i$ and R$^{ii}$ are each independently H or C$_{1-12}$-alkyl.

9. The method of claim 8, wherein R$^2$ is C$_{1-12}$-alkyl.

10. The method of claim 1, wherein R$^2$ is 2-hydroxy-ethyl, 2-fluoro-ethyl, 2,2-difluoro-ethyl, —C(O)CH$_2$N(Me)$_2$, —C(O)methyl, —CH$_2$-pyridin-2-yl, —COO-t-butyl, H, i-propyl, methyl, —S(O)$_2$-methyl or —S(O)$_2$N(methyl)$_2$.

11. The method of claim 10, wherein R$^2$ is 2-hydroxy-ethyl, —C(O)CH$_2$N(Me)$_2$, —C(O)methyl, —CH$_2$-pyridin-2-yl, —COO-t-butyl, H, i-propyl, methyl, —S(O)$_2$-methyl or —S(O)$_2$N(methyl)$_2$.

12. The method of claim 1, wherein R$^2$ is methyl.

13. The method of claim 1, wherein R$^3$ is Cl.

14. The method of claim 1, wherein the compound administered is selected from trans-8-Chloro-1-(4-phenoxy-cyclohexyl)-4H,6H-2,3,5,10b-tetraaza-benzoazulene-5-carboxylic acid tert-butyl ester, trans-8-Chloro-1-(4-phenoxy-cyclohexyl)-5,6-dihydro-4H-2,3,5,10b-tetraaza-benzoazulene hydrochloride, trans-8-Chloro-5-methyl-1-(4-phenoxy-cyclohexyl)-5,6-dihydro-4H-2,3,5,10b-tetraaza-benzo[e]azulene, trans-1-[8-Chloro-1-(4-phenoxy-cyclohexyl)-4H,6H-2,3,5,10b-tetraaza-benzoazulen-5-yl]-ethanone, trans-8-Chloro-5-methanesulfonyl-1-(4-phenoxy-cyclohexyl)-5,6-dihydro-4H-2,3,5,10b-tetraaza-benzoazulene, trans-2-[8-Chloro-1-(4-phenoxy-cyclohexyl)-4H,6H-2,3,5,10b-tetraaza-benzoazulen-5-yl]-ethanol, trans-8-Chloro-5-isopropyl-1-(4-phenoxy-cyclohexyl)-5,6-dihydro-4H-2,3,5,10b-tetraaza-benzoazulene, trans-8-Chloro-1-(4-phenoxy-cyclohexyl)-4H,6H-2,3,5,10b-tetraaza-benzoazulene-5-sulfonic acid dimethylamide, trans-8-Chloro-1-(4-phenoxy-cyclohexyl)-5-pyridin-2-ylmethyl-5,6-dihydro-4H-2,3,5,10b-tetraaza-benzoazulene, trans-1-[8-Chloro-1-(4-phenoxy-cyclohexyl)-4H,6H-2,3,5,10b-tetraaza-benzoazulen-5-yl]-2-dimethylamino-ethanone, and trans-8-Fluoro-1-(4-phenoxy-cyclohexyl)-4H,6H-2,3,5,10b-tetraaza-benzo[e]azulene-5-carboxylic acid tert-butyl ester.

15. The method of claim 1, wherein the compound administered is selected from trans-8-Fluoro-5-methyl-1-(4-phenoxy-cyclohexyl)-5,6-dihydro-4H-2,3,5,10b-tetraaza-benzoazulene, cis-8-Chloro-1-(4-phenoxy-cyclohexyl)-4H,6H-2,3,5,10b-tetraaza-benzoazulene-5-carboxylic acid tert-butyl ester, cis-8-Chloro-5-methyl-1-(4-phenoxy-cyclohexyl)-5,6-dihydro-4H-2,3,5,10b-tetraaza-benzoazulene, trans-8-Chloro-1-[4-(4-fluoro-phenoxy)-cyclohexyl]-4H,6H-2,3,5,10b-tetraaza-benzoazulene-5-carboxylic acid tert-butyl ester, trans-8-Chloro-1-[4-(4-fluoro-phenoxy)-cyclohexyl]-5,6-dihydro-4H-2,3,5,10b-tetraaza-benzo[e]azulene hydrochloride, trans-8-Chloro-1-[4-(4-fluoro-phenoxy)-cyclohexyl]-5-methyl-5,6-dihydro-4H-2,3,5,10b-tetraaza-benzoazulene, trans-8-Chloro-1-[4-(4-cyano-phenoxy)-cyclohexyl]-4H,6H-2,3,5,10b-tetraaza-benzo[e]azulene-5-carboxylic acid tert-butyl ester, trans-4-[4-(8-Chloro-5-methyl-5,6-dihydro-4H-2,3,5,10b-tetraaza-benzo[e]azulen-1-yl)-cyclohexyloxy]-benzonitrile, trans-8-Chloro-1-[4-(4-trifluoromethyl-phenoxy)-cyclohexyl]-4H,6H-2,3,5,10b-tetraaza-benzo[e]azulene-5-carboxylic acid tert-butyl ester, trans-8-Chloro-1-[4-(3-chloro-phenoxy)-cyclohexyl]-4H,6H-2,3,5,10b-tetraaza-benzoazulene-5-carboxylic acid tert-butyl ester, and trans-8-Chloro-1-[4-(3-chloro-phenoxy)-cyclohexyl]-5-methyl-5,6-dihydro-4H-2,3,5,10b-tetraaza-benzoazulene.

16. The method of claim 1, wherein the compound administered is selected from trans-8-Chloro-1-[4-(3-methoxy-phenoxy)-cyclohexyl]-4H,6H-2,3,5,10b-tetraaza-benzoazulene-5-carboxylic acid tert-butyl ester, trans-8-Chloro-1-[4-(3-methoxy-phenoxy)-cyclohexyl]-5,6-dihydro-4H-2,3,5,10b-tetraaza-benzo[e]azulene hydrochloride, trans-8-Chloro-1-[4-(3-methoxy-phenoxy)-cyclohexyl]-5-methyl-5,6-dihydro-4H-2,3,5,10b-tetraaza-benzoazulene, trans-3-[4-(8-Chloro-5-methyl-5,6-dihydro-4H-2,3,5,10b-tetraaza-benzoazulen-1-yl)-cyclohexyloxy]-benzonitrile, trans-8-Chloro-1-(4-m-tolyloxy-cyclohexyl)-4H,6H-2,3,5,10b-tetraaza-benzo[e]azulene-5-carboxylic acid tert-butyl ester, trans-8-Chloro-1-(4-m-tolyloxy-cyclohexyl)-5,6-dihydro-4H-2,3,5,10b-tetraaza-benzo[e]azulene hydrochloride, trans-8-Chloro-5-methyl-1-(4-m-tolyloxy-cyclohexyl)-5,6-dihydro-4H-2,3,5,10b-tetraaza-benzo[e]azulene, trans-1-[4-(3-tert-Butyl-phenoxy)-cyclohexyl]-8-chloro-4H,6H-2,3,5,10b-tetraaza-benzo[e]azulene-5-carboxylic acid tert-butyl ester, trans-8-Chloro-1-[4-(2-fluoro-phenoxy)-cyclohexyl]-4H,6H-2,3,5,10b-tetraaza-benzo[e]azulene-5-carboxylic acid tert-butyl ester, trans-8-Chloro-1-[4-(2-fluoro-phenoxy)-cyclohexyl]-5,6-dihydro-4H-2,3,5,10b-tetraaza-benzo[e]azulene hydrochloride, and trans-8-Chloro-1-[4-(2-fluoro-phenoxy)-cyclohexyl]-5-methyl-5,6-dihydro-4H-2,3,5,10b-tetraaza-benzo[e]azulene.

17. The method of claim 1, wherein the compound administered is selected from trans-8-Chloro-1-[4-(2-cyano-phenoxy)-cyclohexyl]-4H,6H-2,3,5,10b-tetraaza-benzoazulene-5-carboxylic acid tert-butyl ester, trans-2-[4-(8-Chloro-5,6-dihydro-4H-2,3,5,10b-tetraaza-benzo[e]azulen-1-yl)-cyclohexyloxy]-benzonitrile hydrochloride, trans-2-[4-(8-Chloro-5-methyl-5,6-dihydro-4H-2,3,5,10b-tetraaza-benzoazulen-1-yl)-cyclohexyloxy]-benzonitrile, trans-8-Chloro-1-(4-o-tolyloxy-cyclohexyl)-4H,6H-2,3,5,10b-tetraaza-benzoazulene-5-carboxylic acid tert-butyl ester, trans-8-Chloro-5-methyl-1-(4-o-tolyloxy-cyclohexyl)-5,6-dihydro-4H-2,3,5,10b-tetraaza-benzoazulene, trans-8-Chloro-1-[4-(3,5-difluoro-phenoxy)-cyclohexyl]-4H,6H-2,3,5,10b-tetraaza-benzoazulene-5-carboxylic acid tert-butyl ester, trans-8-Chloro-1-[4-(3,5-difluoro-phenoxy)-cyclohexyl]-5-methyl-5,6-dihydro-4H-2,3,5,10b-tetraaza-benzoazulene, trans-8-Chloro-1-[4-(naphthalen-2-yloxy)-cyclohexyl]-4H,6H-2,3,5,10b-tetraaza-benzoazulene-5-carboxylic acid tert-butyl ester, trans-8-Chloro-5-methyl-1-[4-(naphthalen-2-yloxy)-cyclohexyl]-5,6-dihydro-4H-2,3,5,10b-tetraaza-benzoazulene, trans-8-Chloro-1-[4-(pyridin-3-yloxy)-cyclohexyl]-4H,6H-2,3,5,10b-tetraaza-benzoazulene-5-carboxylic acid tert-butyl ester, and trans-8-Chloro-5-methyl-1-[4-(pyridin-3-yloxy)-cyclohexyl]-5,6-dihydro-4H-2,3,5,10b-tetraaza-benzoazulene.

18. The method of claim 1, wherein the compound administered is selected from trans-8-Chloro-1-[4-(5-chloro-pyridin-3-yloxy)-cyclohexyl]-4H,6H-2,3,5,10b-tetraaza-benzoazulene-5-carboxylic acid tert-butyl ester, trans-8-Chloro-1-[4-(5-chloro-pyridin-3-yloxy)-cyclohexyl]-5-methyl-5,6-dihydro-4H-2,3,5,10b-tetraaza-benzoazulene, trans-8-Chloro-1-[4-(pyridin-2-yloxy)-cyclohexyl]-4H,6H-2,3,5,10b-tetraaza-benzoazulene-5-carboxylic acid tert-butyl ester, trans-8-Chloro-1-[4-(pyridin-2-yloxy)-cyclohexyl]-5,6-dihydro-4H-2,3,5,10b-tetraaza-benzoazulene hydrochloride, trans-8-Chloro-5-methyl-1-[4-(pyridin-2-yloxy)-cyclohexyl]-5,6-dihydro-4H-2,3,5,10b-tetraaza-benzoazulene, trans-8-Chloro-1-[4-(6-chloro-pyridin-2-yloxy)-cyclohexyl]-4H,6H-2,3,5,10b-tetraaza-benzo[e]azulene-5-carboxylic acid tert-butyl ester, trans-8-Chloro-1-[4-(6-chloro-pyridin-2-yloxy)-cyclohexyl]-5-methyl-5,6-dihydro-4H-2,3,5,10b-tetraaza-benzo[e]azulene, trans-8-Chloro-1-[4-(5-chloro-pyridin-2-yloxy)-cyclohexyl]-5-methyl-5,6-dihydro-4H-2,3,5,10b-tetraaza-benzo[e]azulene hydrochloride, trans-8-Chloro-1-[4-(5-chloro-pyridin-2-yloxy)-cyclohexyl]-5-methyl-5,6-dihydro-4H-2,3,5,10b-tetraaza-benzo[e]azulene, trans-8-Chloro-1-[4-(pyrimidin-2-yloxy)-cyclohexyl]-4H,6H-2,3,5,10b-tetraaza-benzo[e]azulene-5-carboxylic acid tert-butyl ester, and cis-8-Chloro-1-[4-(pyrimidin-2-yloxy)-cyclohexyl]-4H,6H-2,3,5,10b-tetraaza-benzo[e]azulene-5-carboxylic acid tert-butyl ester.

19. The method of claim 1, wherein the compound administered is selected from trans-8-Chloro-5-methyl-1-[4-(pyrimidin-2-yloxy)-cyclohexyl]-5,6-dihydro-4H-2,3,5,10b-tetraaza-benzo[e]azulene, trans-8-Chloro-1-[4-(pyrazin-2-yloxy)-cyclohexyl]-4H,6H-2,3,5,10b-tetraaza-benzo[e]azulene-5-carboxylic acid tert-butyl ester, trans-8-Chloro-5-methyl-1-[4-(pyrazin-2-yloxy)-cyclohexyl]-5,6-dihydro-4H-2,3,5,10b-tetraaza-benzo[e]azulene, trans-8-Chloro-1-[4-(pyrimidin-4-yloxy)-cyclohexyl]-4H,6H-2,3,5,10b-tetraaza-benzo[e]azulene-5-carboxylic acid tert-butyl ester, trans-8-Chloro-5-methyl-1-[4-(pyrimidin-4-yloxy)-cyclohexyl]-5,6-dihydro-4H-2,3,5,10b-tetraaza-benzo[e]azulene, trans-8-Chloro-1-[4-(pyridazin-3-yloxy)-cyclohexyl]-4H,6H-2,3,5,10b-tetraaza-benzo[e]azulene-5-carboxylic acid tert-butyl ester, cis-8-Chloro-1-[4-(pyridazin-3-yloxy)-cyclohexyl]-4H,6H-2,3,5,10b-tetraaza-benzo[e]azulene-5-carboxylic acid tert-butyl ester, trans-8-Chloro-5-methyl-1-[4-(pyridazin-3-yloxy)-cyclohexyl]-5,6-dihydro-4H-2,3,5,10b-tetraaza-benzo[e]azulene, cis-8-Chloro-1-[4-(pyridin-2-yloxy)-cyclohexyl]-4H,6H-2,3,5,10b-tetraaza-benzo[e]azulene-5-carboxylic acid tert-butyl ester,
cis-8-Chloro-1-[4-(pyridin-2-yloxy)-cyclohexyl]-5,6-dihydro-4H-2,3,5,10b-tetraaza-benzo[e]azulene, and
cis-8-Chloro-5-methyl-1-[4-(pyridin-2-yloxy)-cyclohexyl]-5,6-dihydro-4H-2,3,5,10b-tetraaza-benzo[e]azulene.

20. The method of claim 1, wherein the compound administered is selected from
trans-8-Chloro-1-[4-(3-fluoro-pyridin-2-yloxy)-cyclohexyl]-5,6-dihydro-4H-2,3,5,10b-tetraaza-benzo[e]azulene,
trans-8-Chloro-1-[4-(3-fluoro-pyridin-2-yloxy)-cyclohexyl]-5-methyl-5,6-dihydro-4H-2,3,5,10b-tetraaza-benzo[e]azulene,
trans-8-Chloro-1-[4-(5-fluoro-pyridin-2-yloxy)-cyclohexyl]-5,6-dihydro-4H-2,3,5,10b-tetraaza-benzo[e]azulene,
trans-8-Chloro-1-[4-(5-fluoro-pyridin-2-yloxy)-cyclohexyl]-5-methyl-5,6-dihydro-4H-2,3,5,10b-tetraaza-benzo[e]azulene,
trans-8-Chloro-1-[4-(6-methyl-pyridin-2-yloxy)-cyclohexyl]-5,6-dihydro-4H-2,3,5,10b-tetraaza-benzo[e]azulene,
trans-8-Chloro-5-(2,2-difluoro-ethyl)-1-[4-(6-methyl-pyridin-2-yloxy)-cyclohexyl]-5,6-dihydro-4H-2,3,5,10b-tetraaza-benzo[e]azulene,
trans-8-Chloro-5-(2-fluoro-ethyl)-1-[4-(5-fluoro-pyridin-2-yloxy)-cyclohexyl]-5,6-dihydro-4H-2,3,5,10b-tetraaza-benzo[e]azulene,
trans-8-Chloro-5-ethyl-1-[4-(3-fluoro-pyridin-2-yloxy)-cyclohexyl]-5,6-dihydro-4H-2,3,5,10b-tetraaza-benzo[e]azulene,
trans-8-Chloro-5-ethyl-1-[4-(5-fluoro-pyridin-2-yloxy)-cyclohexyl]-5,6-dihydro-4H-2,3,5,10b-tetraaza-benzo[e]azulene,
trans-8-Chloro-5-ethyl-1-[4-(6-methyl-pyridin-2-yloxy)-cyclohexyl]-5,6-dihydro-4H-2,3,5,10b-tetraaza-benzo[e]azulene, and
trans-8-Chloro-5-methyl-1-[4-(6-methyl-pyridin-2-yloxy)-cyclohexyl]-5,6-dihydro-4H-2,3,5,10b-tetraaza-benzo[e]azulene.

21. The method of claim 1, wherein the compound administered is selected from
trans-8-Chloro-5-methyl-1-(4-phenoxy-cyclohexyl)-5,6-dihydro-4H-2,3,5,10b-tetraaza-benzo[e]azulene and
trans-8-Chloro-5-methyl-1-[4-(pyridin-2-yloxy)-cyclohexyl]-5,6-dihydro-4H-2,3,5,10b-tetraaza-benzoazulene.

22. The method of claim 1, wherein the compound administered is trans-8-Chloro-5-methyl-1-[4-(pyridin-2-yloxy)-cyclohexyl]-5,6-dihydro-4H-2,3,5,10b-tetraaza-benzoazulene.

* * * * *